(12) United States Patent
Sennett et al.

(10) Patent No.: US 10,588,646 B2
(45) Date of Patent: Mar. 17, 2020

(54) DEVICES AND METHODS FOR FRACTURE REDUCTION

(71) Applicant: GLOBUS MEDICAL, INC., Audubon, PA (US)

(72) Inventors: Andrew R. Sennett, Hanover, MA (US); Randall J. Beyreis, Corcoran, MN (US); Brett A. Williams, Lino Lakes, MN (US)

(73) Assignee: Globus Medical, Inc., Audubon, PA (US)

(*) Notice: Subject to any disclaimer, the term of this patent is extended or adjusted under 35 U.S.C. 154(b) by 337 days.

(21) Appl. No.: 15/589,287

(22) Filed: May 8, 2017

(65) Prior Publication Data

US 2017/0238943 A1 Aug. 24, 2017

Related U.S. Application Data

(60) Continuation of application No. 14/881,252, filed on Oct. 13, 2015, now Pat. No. 9,687,255, which is a (Continued)

(51) Int. Cl.
*A61B 17/16* (2006.01)
*A61B 17/88* (2006.01)

(52) U.S. Cl.
CPC ...... *A61B 17/1671* (2013.01); *A61B 17/1617* (2013.01); *A61B 17/1631* (2013.01); *A61B 17/1642* (2013.01); *A61B 17/8855* (2013.01)

(58) Field of Classification Search
CPC ............ A61B 17/1631; A61B 17/1642; A61B 17/1671; A61B 17/8855
See application file for complete search history.

(56) References Cited

U.S. PATENT DOCUMENTS 1,353,833 A * 9/1920 Haley .................... F16L 41/06
                                                        74/841
1,406,187 A * 2/1922 Herdlitchka ............ E21B 7/021
                                                        173/145
(Continued)

FOREIGN PATENT DOCUMENTS

DE        10154163 A1    5/2003
EP         1073371 B1    2/2001
(Continued)

OTHER PUBLICATIONS

Lam et al. (2005) "A Novel Percutaneous System for Bone Graft Delivery and Containment for Elevation and Stabilization of Vertebral Compression Fractures", Neurosug Focus, 18(3), 1-7.
(Continued)

*Primary Examiner* — Zade Coley

(57) ABSTRACT

Methods of creating a curvilinear cavity within a vertebral body or other bony structure and devices that may be used to perform the steps to create the curvilinear cavity. In one embodiment, a method of forming a curvilinear void in bony structure may include the steps of accessing a bony structure with a cannula, inserting a distal end of a drill device through the cannula and into the bony structure, manipulating the distal end of the drill device to create a curvilinear void in the bony structure, enlarging the void by expansion of a balloon element mounted to the drill device, and deflating the balloon element and removing the drill device from the cannula.

20 Claims, 47 Drawing Sheets

Related U.S. Application Data division of application No. 12/486,439, filed on Jun. 17, 2009, now Pat. No. 9,192,397.

(60) Provisional application No. 61/073,184, filed on Jun. 17, 2008.

(56) References Cited

U.S. PATENT DOCUMENTS

| | | | |
|---|---|---|---|
| 1,630,239 A * | 5/1927 | Binkley | A61B 17/1642 606/180 |
| 1,705,232 A * | 3/1929 | Brantingson | B23Q 5/32 173/141 |
| 1,768,318 A * | 6/1930 | Harasimiak | E21C 1/10 173/33 |
| 2,090,330 A * | 8/1937 | Jones | E21C 1/10 173/146 |
| 2,106,173 A * | 1/1938 | Hawker | B23C 3/05 408/111 |
| 2,143,975 A * | 1/1939 | Crofton | E21B 19/081 173/145 |
| 2,214,753 A * | 9/1940 | Sinclair | E21B 19/081 173/143 |
| 2,507,155 A * | 5/1950 | Gruen | B23B 23/00 408/137 |
| 2,601,434 A * | 6/1952 | Du Bois | F16L 41/04 137/318 |
| 3,176,395 A | 4/1965 | Warner et al. | |
| 3,804,544 A * | 4/1974 | Adams | A61B 17/16 173/146 |
| 3,875,595 A | 4/1975 | Froning | |
| 4,065,817 A | 1/1978 | Branemark et al. | |
| 4,313,434 A | 2/1982 | Segal | |
| 4,488,549 A | 12/1984 | Lee et al. | |
| 4,535,764 A | 8/1985 | Ebert | |
| 4,541,423 A | 9/1985 | Barber | |
| 4,627,434 A | 12/1986 | Murray | |
| 4,643,190 A | 2/1987 | Heimberger et al. | |
| 4,653,487 A | 3/1987 | Maale | |
| 4,653,489 A | 3/1987 | Tronzo | |
| 4,693,721 A | 9/1987 | Ducheyne | |
| 4,755,184 A | 7/1988 | Silverberg | |
| 4,772,264 A | 9/1988 | Cragg | |
| 4,820,349 A | 4/1989 | Saab | |
| 4,969,888 A | 11/1990 | Scholten et al. | |
| 5,002,543 A | 3/1991 | Bradshaw et al. | |
| 5,009,661 A | 4/1991 | Michelson | |
| 5,015,255 A | 5/1991 | Kuslich | |
| 5,030,233 A | 7/1991 | Ducheyne | |
| 5,047,055 A | 9/1991 | Bao et al. | |
| 5,059,193 A | 10/1991 | Kuslich | |
| 5,062,845 A | 11/1991 | Kuslich et al. | |
| 5,085,635 A | 2/1992 | Cragg | |
| 5,100,423 A | 3/1992 | Fearnot | |
| 5,108,404 A | 4/1992 | Scholten et al. | |
| 5,192,326 A | 3/1993 | Bao et al. | |
| 5,257,994 A | 11/1993 | Lin | |
| 5,269,785 A | 12/1993 | Bonutti | |
| 5,290,312 A | 3/1994 | Kojimoto et al. | |
| 5,322,505 A | 6/1994 | Krause et al. | |
| 5,332,402 A | 7/1994 | Teitelbaum | |
| 5,342,371 A | 8/1994 | Welter et al. | |
| 5,370,653 A | 12/1994 | Cragg | |
| 5,397,310 A | 3/1995 | Chu et al. | |
| 5,405,377 A | 4/1995 | Cragg | |
| 5,419,774 A * | 5/1995 | Willard | A61B 17/3207 604/22 |
| 5,437,665 A | 8/1995 | Munro | |
| 5,445,639 A | 8/1995 | Kuslich et al. | |
| 5,489,274 A | 2/1996 | Chu et al. | |
| 5,489,308 A | 2/1996 | Kuslich et al. | |
| 5,499,981 A | 3/1996 | Kordis | |
| 5,540,693 A | 7/1996 | Fisher | |
| 5,549,637 A | 8/1996 | Crainich | |
| 5,549,679 A | 8/1996 | Kuslich | |
| 5,554,114 A | 9/1996 | Wallace et al. | |
| 5,571,189 A | 11/1996 | Kuslich | |
| 5,628,788 A | 5/1997 | Pinchuk | |
| 5,630,840 A | 5/1997 | Mayor | |
| 5,645,545 A | 7/1997 | Bryant | |
| 5,645,566 A | 7/1997 | Brenneman et al. | |
| 5,649,941 A * | 7/1997 | Lary | A61B 17/3207 604/22 |
| 5,665,115 A | 9/1997 | Cragg | |
| 5,683,448 A | 11/1997 | Cragg | |
| 5,695,513 A | 12/1997 | Johnson et al. | |
| 5,716,365 A | 2/1998 | Goicoechea et al. | |
| 5,752,969 A | 5/1998 | Cunci et al. | |
| 5,759,191 A | 6/1998 | Barbere | |
| 5,766,237 A | 6/1998 | Cragg | |
| 5,776,180 A | 7/1998 | Goicoechea et al. | |
| 5,782,861 A | 7/1998 | Cragg et al. | |
| 5,795,331 A | 8/1998 | Cragg et al. | |
| 5,807,330 A | 9/1998 | Teitelbaum | |
| 5,810,717 A * | 9/1998 | Maeda | A61B 1/00193 600/143 |
| 5,810,828 A | 9/1998 | Lightman et al. | |
| 5,814,044 A | 9/1998 | Hooven | |
| 5,827,289 A | 10/1998 | Reiley et al. | |
| 5,833,692 A | 11/1998 | Cesarini et al. | |
| 5,851,208 A | 12/1998 | Trott | |
| 5,868,762 A | 2/1999 | Cragg et al. | |
| 5,916,263 A | 6/1999 | Goicoechea et al. | |
| 5,928,239 A | 7/1999 | Mirza | |
| 5,957,884 A | 9/1999 | Hooven | |
| 5,957,974 A | 9/1999 | Thompson et al. | |
| 5,972,015 A | 10/1999 | Scribner et al. | |
| 5,984,950 A | 11/1999 | Cragg et al. | |
| 5,989,223 A | 11/1999 | Chu et al. | |
| 5,989,256 A | 11/1999 | Kuslich et al. | |
| 6,019,786 A | 1/2000 | Ohkoshi et al. | |
| 6,051,020 A | 4/2000 | Goicoechea et al. | |
| 6,053,922 A | 4/2000 | Krause et al. | |
| 6,056,749 A | 5/2000 | Kuslich | |
| 6,063,069 A | 5/2000 | Cragg et al. | |
| 6,071,300 A | 6/2000 | Brenneman et al. | |
| 6,071,301 A | 6/2000 | Cragg et al. | |
| 6,086,589 A | 7/2000 | Kuslich et al. | |
| 6,086,607 A | 7/2000 | Cragg et al. | |
| 6,096,021 A | 8/2000 | Helm et al. | |
| 6,096,038 A | 8/2000 | Michelson | |
| 6,096,054 A * | 8/2000 | Wyzgala | A61B 17/32072 606/170 |
| 6,113,604 A | 9/2000 | Whittaker et al. | |
| 6,117,167 A | 9/2000 | Goicoechea et al. | |
| 6,127,597 A | 10/2000 | Beyar et al. | |
| 6,146,373 A | 11/2000 | Cragg et al. | |
| 6,146,422 A | 11/2000 | Lawson | |
| 6,149,654 A | 11/2000 | Johnson | |
| 6,162,192 A | 12/2000 | Cragg et al. | |
| 6,174,328 B1 | 1/2001 | Cragg | |
| 6,179,856 B1 | 1/2001 | Barbere | |
| 6,199,551 B1 | 3/2001 | Kuslich | |
| 6,200,328 B1 | 3/2001 | Cragg et al. | |
| 6,203,779 B1 | 3/2001 | Ricci et al. | |
| 6,228,120 B1 | 5/2001 | Leonard et al. | |
| 6,235,043 B1 | 5/2001 | Reiley et al. | |
| 6,241,734 B1 | 6/2001 | Scribner et al. | |
| 6,245,107 B1 | 6/2001 | Ferree | |
| 6,248,110 B1 | 6/2001 | Reiley et al. | |
| 6,248,131 B1 | 6/2001 | Felt et al. | |
| 6,258,089 B1 | 7/2001 | Campbell et al. | |
| 6,261,293 B1 | 7/2001 | Nicholson et al. | |
| 6,280,456 B1 | 8/2001 | Scribner et al. | |
| 6,302,906 B1 | 10/2001 | Goicoechea et al. | |
| 6,303,100 B1 | 10/2001 | Ricci et al. | |
| 6,306,177 B1 | 10/2001 | Felt et al. | |
| 6,309,395 B1 | 10/2001 | Ritland | |
| 6,315,753 B1 | 11/2001 | Cragg et al. | |
| 6,315,789 B1 | 11/2001 | Cragg | |
| 6,319,255 B1 | 11/2001 | Grundei et al. | |
| RE37,479 E | 12/2001 | Kuslich | |
| 6,332,881 B1 * | 12/2001 | Carner | A61B 18/1402 606/41 |

(56) References Cited

U.S. PATENT DOCUMENTS

| | | | |
|---|---|---|---|
| 6,337,142 B2 | 1/2002 | Harder et al. |
| 6,342,068 B1 | 1/2002 | Thompson |
| 6,346,117 B1 | 2/2002 | Greenhalgh |
| 6,348,066 B1 | 2/2002 | Pinchuk et al. |
| 6,364,895 B1 | 4/2002 | Greenhalgh |
| 6,371,974 B1 | 4/2002 | Brenneman et al. |
| 6,375,670 B1 | 4/2002 | Greenhalgh |
| 6,383,188 B2 | 5/2002 | Kuslich et al. |
| 6,387,122 B1 | 5/2002 | Cragg |
| 6,391,037 B1 | 5/2002 | Greenhalgh |
| 6,395,032 B1 | 5/2002 | Gauchet et al. |
| 6,402,784 B1 | 6/2002 | Wardiaw et al. |
| 6,423,083 B2 | 7/2002 | Reiley et al. |
| 6,440,138 B1 | 8/2002 | Reiley et al. |
| 6,440,151 B1 | 8/2002 | Cragg et al. |
| 6,440,153 B2 | 8/2002 | Cragg et al. |
| 6,447,534 B2 | 9/2002 | Cragg et al. |
| 6,458,127 B1 | 10/2002 | Truckai et al. |
| 6,475,466 B1 | 11/2002 | Ricci et al. |
| 6,488,710 B2 | 12/2002 | Besselink et al. |
| 6,508,839 B1 | 1/2003 | Lambrecht et al. |
| 6,511,468 B1 | 1/2003 | Cragg et al. |
| 6,514,258 B1 | 2/2003 | Brown et al. |
| 6,527,734 B2 | 3/2003 | Cragg et al. |
| 6,533,751 B2 | 3/2003 | Cragg et al. |
| 6,533,817 B1 | 3/2003 | Norton et al. |
| 6,540,739 B2 | 4/2003 | Lechot et al. |
| 6,544,236 B1 | 4/2003 | Cragg et al. |
| 6,558,367 B1 | 5/2003 | Cragg et al. |
| 6,558,386 B1 | 5/2003 | Cragg |
| 6,558,390 B2 | 5/2003 | Cragg |
| 6,575,978 B2 | 6/2003 | Peterson et al. |
| 6,575,979 B1 * | 6/2003 | Cragg | A61B 17/1671 |
| | | | 606/279 |
| 6,582,467 B1 | 6/2003 | Teitelbaum et al. |
| 6,592,617 B2 | 7/2003 | Thompson |
| 6,607,544 B1 | 8/2003 | Boucher et al. |
| 6,610,026 B2 | 8/2003 | Cragg et al. |
| 6,620,162 B2 | 9/2003 | Kuslich et al. |
| 6,620,169 B1 | 9/2003 | Peterson et al. |
| 6,626,907 B2 | 9/2003 | Campbell et al. |
| 6,632,235 B2 | 10/2003 | Weikel et al. |
| 6,635,027 B1 | 10/2003 | Cragg et al. |
| 6,641,587 B2 | 11/2003 | Scribner et al. |
| 6,641,607 B1 | 11/2003 | Hossainy et al. |
| 6,656,185 B2 | 12/2003 | Gleason et al. |
| 6,663,647 B2 | 12/2003 | Reiley et al. |
| 6,679,886 B2 | 1/2004 | Weikel et al. |
| 6,689,162 B1 | 2/2004 | Thompson |
| 6,692,459 B2 | 2/2004 | Teitelbaum |
| 6,706,044 B2 | 3/2004 | Kuslich et al. |
| 6,709,435 B2 | 3/2004 | Lin |
| 6,712,819 B2 | 3/2004 | Zucherman et al. |
| 6,712,853 B2 | 3/2004 | Kuslich |
| 6,716,207 B2 * | 4/2004 | Farnholtz | A61M 25/0053 |
| | | | 604/523 |
| 6,716,216 B1 | 4/2004 | Boucher et al. |
| 6,719,773 B1 | 4/2004 | Boucher et al. |
| 6,726,691 B2 | 4/2004 | Osorio et al. |
| 6,740,090 B1 | 5/2004 | Cragg et al. |
| 6,740,093 B2 | 5/2004 | Hochschuler et al. |
| 6,749,614 B2 | 6/2004 | Teitelbaum et al. |
| 6,780,189 B2 | 8/2004 | Tidwell et al. |
| 6,786,903 B2 | 9/2004 | Lin |
| 6,790,210 B1 | 9/2004 | Cragg et al. |
| 6,796,988 B2 | 9/2004 | Melkent et al. |
| 6,805,697 B1 | 10/2004 | Helm et al. |
| 6,814,754 B2 | 11/2004 | Greenhalgh |
| 6,821,277 B2 | 11/2004 | Teitelbaum |
| 6,824,087 B2 | 11/2004 | McPherson et al. |
| 6,827,743 B2 | 12/2004 | Eisermann et al. |
| 6,849,086 B2 | 2/2005 | Cragg |
| 6,863,672 B2 | 3/2005 | Reiley et al. |
| 6,869,445 B1 | 3/2005 | Johnson |
| 6,875,212 B2 | 4/2005 | Shaolian et al. |
| 6,875,219 B2 | 4/2005 | Arramon et al. |
| 6,896,677 B1 | 5/2005 | Lin et al. |
| 6,899,713 B2 | 5/2005 | Shaolian et al. |
| 6,899,716 B2 | 5/2005 | Cragg |
| 6,899,719 B2 | 5/2005 | Reiley et al. |
| 6,921,403 B2 | 7/2005 | Cragg et al. |
| 6,923,811 B1 | 8/2005 | Carl et al. |
| 6,923,813 B2 | 8/2005 | Phillips et al. |
| 6,929,659 B2 | 8/2005 | Pinchuk |
| 6,951,562 B2 | 10/2005 | Zwirnmann |
| 6,958,061 B2 | 10/2005 | Truckai et al. |
| 6,960,215 B2 | 11/2005 | Olson, Jr. et al. |
| 6,964,657 B2 | 11/2005 | Cragg et al. |
| 6,964,667 B2 | 11/2005 | Shaolian et al. |
| 6,979,341 B2 | 12/2005 | Scribner et al. |
| 6,981,981 B2 | 1/2006 | Reiley et al. |
| 6,984,219 B2 | 1/2006 | Ashby et al. |
| 6,997,929 B2 | 2/2006 | Manzi et al. |
| 7,008,424 B2 | 3/2006 | Teitelbaum |
| 7,011,661 B2 | 3/2006 | Riedel et al. |
| 7,014,633 B2 | 3/2006 | Cragg |
| 7,025,771 B2 | 4/2006 | Kuslich et al. |
| 7,037,323 B2 | 5/2006 | Sing et al. |
| 7,044,954 B2 | 5/2006 | Reiley et al. |
| 7,048,710 B1 | 5/2006 | Cragg et al. |
| 7,056,317 B2 | 6/2006 | Lechot et al. |
| 7,056,345 B2 | 6/2006 | Kuslich |
| 7,063,703 B2 | 6/2006 | Reo |
| 7,081,122 B1 | 7/2006 | Reiley et al. |
| 7,083,621 B2 | 8/2006 | Shaolian et al. |
| 7,087,055 B2 | 8/2006 | Lim et al. |
| 7,087,058 B2 | 8/2006 | Cragg |
| 7,114,501 B2 | 10/2006 | Johnson et al. |
| 7,122,043 B2 | 10/2006 | Greenhalgh et al. |
| 7,122,052 B2 | 10/2006 | Greenhalgh |
| 7,131,605 B2 | 11/2006 | McPherson et al. |
| 7,135,021 B2 | 11/2006 | Lin et al. |
| 7,141,074 B2 | 11/2006 | Fanger et al. |
| 7,147,650 B2 | 12/2006 | Lee |
| 7,153,306 B2 | 12/2006 | Ralph et al. |
| 7,153,307 B2 | 12/2006 | Scribner et al. |
| 7,175,627 B2 | 2/2007 | Lin et al. |
| 7,175,628 B2 | 2/2007 | Lin et al. |
| 7,175,629 B2 | 2/2007 | Lin et al. |
| 7,175,646 B2 | 2/2007 | Brenneman et al. |
| 7,179,024 B2 | 2/2007 | Greenhalgh |
| 7,192,436 B2 | 3/2007 | Sing et al. |
| 7,201,725 B1 | 4/2007 | Cragg et al. |
| 7,220,282 B2 | 5/2007 | Kuslich |
| 7,226,481 B2 | 6/2007 | Kuslich |
| 7,234,468 B2 | 6/2007 | Johnson et al. |
| 7,241,297 B2 | 7/2007 | Shaolian et al. |
| 7,309,338 B2 | 12/2007 | Cragg |
| 7,311,713 B2 | 12/2007 | Johnson et al. |
| 7,312,826 B2 | 12/2007 | Ishii |
| RE39,995 E | 1/2008 | Pepper et al. |
| 7,318,826 B2 | 1/2008 | Teitelbaum et al. |
| 7,329,268 B2 | 2/2008 | Cragg |
| 7,338,513 B2 | 3/2008 | Lee et al. |
| 7,364,582 B2 | 4/2008 | Lee |
| D583,051 S | 12/2008 | Lee et al. |
| 7,465,318 B2 | 12/2008 | Sennett et al. |
| 2001/0034509 A1 | 10/2001 | Cragg et al. |
| 2001/0034526 A1 | 10/2001 | Kuslich et al. |
| 2001/0041913 A1 | 11/2001 | Cragg et al. |
| 2001/0044647 A1 | 11/2001 | Pinchuk et al. |
| 2001/0049527 A1 | 12/2001 | Cragg |
| 2001/0049554 A1 | 12/2001 | Ruiz et al. |
| 2001/0056254 A1 | 12/2001 | Cragg et al. |
| 2001/0056299 A1 | 12/2001 | Thompson |
| 2002/0007190 A1 * | 1/2002 | Wulfman | A61B 17/320725 |
| | | | 606/167 |
| 2002/0010442 A1 | 1/2002 | Teitelbaum |
| 2002/0010472 A1 | 1/2002 | Kuslich et al. |
| 2002/0013616 A1 | 1/2002 | Carter et al. |
| 2002/0016583 A1 | 2/2002 | Cragg |
| 2002/0016611 A1 | 2/2002 | Cragg et al. |
| 2002/0019659 A1 | 2/2002 | Golcoechea et al. |
| 2002/0022822 A1 | 2/2002 | Cragg et al. |

(56) References Cited

U.S. PATENT DOCUMENTS

| | | |
|---|---|---|
| 2002/0022856 A1 | 2/2002 | Johnson et al. |
| 2002/0034493 A1 | 3/2002 | Ricci et al. |
| 2002/0058947 A1 | 5/2002 | Hochschuler et al. |
| 2002/0058992 A1 | 5/2002 | Greenhalgh |
| 2002/0062104 A1 | 5/2002 | Ashby et al. |
| 2002/0062106 A1 | 5/2002 | Chu et al. |
| 2002/0066360 A1 | 6/2002 | Greenhalgh et al. |
| 2002/0068974 A1 | 6/2002 | Kuslich et al. |
| 2002/0068975 A1 | 6/2002 | Teitelbaum et al. |
| 2002/0077701 A1 | 6/2002 | Kuslich |
| 2002/0082598 A1 | 6/2002 | Teitelbaum |
| 2002/0082600 A1 | 6/2002 | Shaolian et al. |
| 2002/0091372 A1 | 7/2002 | Cragg et al. |
| 2002/0116013 A1 | 8/2002 | Gleason et al. |
| 2002/0116051 A1 | 8/2002 | Cragg |
| 2002/0123750 A1 | 9/2002 | Eisermann et al. |
| 2002/0156495 A1 | 10/2002 | Brenneman et al. |
| 2002/0169449 A1 | 11/2002 | Kuslich et al. |
| 2002/0173796 A1 | 11/2002 | Cragg |
| 2002/0173813 A1 | 11/2002 | Peterson et al. |
| 2002/0183761 A1 | 12/2002 | Johnson et al. |
| 2002/0188300 A1 | 12/2002 | Arramon et al. |
| 2002/0198526 A1 | 12/2002 | Shaolian et al. |
| 2003/0018292 A1 | 1/2003 | Kuslich et al. |
| 2003/0040733 A1 | 2/2003 | Cragg et al. |
| 2003/0068296 A1 | 4/2003 | Ricci et al. |
| 2003/0074075 A1 | 4/2003 | Thomas et al. |
| 2003/0082169 A1 | 5/2003 | Boyd |
| 2003/0083642 A1 | 5/2003 | Boyd et al. |
| 2003/0083669 A1 | 5/2003 | Gleason |
| 2003/0083746 A1 | 5/2003 | Kuslich |
| 2003/0083749 A1 | 5/2003 | Kuslich et al. |
| 2003/0088249 A1 | 5/2003 | Furderer |
| 2003/0088271 A1 | 5/2003 | Cragg et al. |
| 2003/0105469 A1 | 6/2003 | Karmon |
| 2003/0108589 A1 | 6/2003 | Lacout et al. |
| 2003/0135237 A1 | 7/2003 | Cragg et al. |
| 2003/0149472 A1 | 8/2003 | Pinchuk et al. |
| 2003/0153971 A1 | 8/2003 | Chandrasekaran |
| 2003/0158557 A1 | 8/2003 | Cragg et al. |
| 2003/0181982 A1 | 9/2003 | Kuslich |
| 2003/0187433 A1 | 10/2003 | Lin |
| 2003/0191474 A1 | 10/2003 | Cragg et al. |
| 2003/0195518 A1 | 10/2003 | Cragg |
| 2003/0195611 A1 | 10/2003 | Greenhalgh et al. |
| 2003/0204189 A1 | 10/2003 | Cragg |
| 2003/0208263 A1 | 11/2003 | Burmeister et al. |
| 2003/0211135 A1 | 11/2003 | Greenhalgh et al. |
| 2003/0220649 A1 | 11/2003 | Bao et al. |
| 2003/0225391 A1 | 12/2003 | Cragg et al. |
| 2003/0229353 A1 | 12/2003 | Cragg |
| 2003/0233096 A1 | 12/2003 | Osorio et al. |
| 2004/0006341 A1 | 1/2004 | Shaolian et al. |
| 2004/0006344 A1 | 1/2004 | Nguyen et al. |
| 2004/0006355 A1* | 1/2004 | Vetter ............... A61B 10/0266 606/167 |
| 2004/0019354 A1 | 1/2004 | Johnson et al. |
| 2004/0033364 A1 | 2/2004 | Spiridligliozzi et al. |
| 2004/0051201 A1 | 3/2004 | Greenhalgh et al. |
| 2004/0064144 A1 | 4/2004 | Johnson et al. |
| 2004/0073139 A1 | 4/2004 | Hirsch et al. |
| 2004/0073287 A1 | 4/2004 | Goicoechea et al. |
| 2004/0073293 A1 | 4/2004 | Thompson |
| 2004/0073308 A1 | 4/2004 | Kuslich et al. |
| 2004/0082954 A1 | 4/2004 | Teitelbaum et al. |
| 2004/0082961 A1 | 4/2004 | Teitelbaum |
| 2004/0087950 A1 | 5/2004 | Teitelbaum |
| 2004/0092933 A1 | 5/2004 | Shaolian et al. |
| 2004/0092988 A1 | 5/2004 | Shaolian et al. |
| 2004/0092993 A1* | 5/2004 | Teitelbaum ......... A61B 17/1617 606/180 |
| 2004/0098086 A1 | 5/2004 | Goicoechea et al. |
| 2004/0098115 A1 | 5/2004 | Goicoechea et al. |
| 2004/0102774 A1 | 5/2004 | Trieu |
| 2004/0106940 A1 | 6/2004 | Shaolian et al. |
| 2004/0106979 A1 | 6/2004 | Goicoechea et al. |
| 2004/0106999 A1 | 6/2004 | Mathews |
| 2004/0133220 A1 | 7/2004 | Lashinski et al. |
| 2004/0138707 A1 | 7/2004 | Greenhalgh |
| 2004/0138744 A1 | 7/2004 | Lashinski et al. |
| 2004/0147934 A1 | 7/2004 | Kiester |
| 2004/0153146 A1 | 8/2004 | Lashinski et al. |
| 2004/0158287 A1 | 8/2004 | Cragg et al. |
| 2004/0162559 A1 | 8/2004 | Arramon et al. |
| 2004/0167562 A1 | 8/2004 | Osorlo et al. |
| 2004/0167599 A1 | 8/2004 | Goicoechea et al. |
| 2004/0176723 A1 | 9/2004 | Sing et al. |
| 2004/0176741 A1* | 9/2004 | Famholtz .......... A61M 25/0053 604/527 |
| 2004/0181191 A1 | 9/2004 | Teitelbaum |
| 2004/0186480 A1 | 9/2004 | Lin et al. |
| 2004/0186481 A1 | 9/2004 | Chern Lin et al. |
| 2004/0186576 A1 | 9/2004 | Biscup et al. |
| 2004/0208717 A1 | 10/2004 | Greenhalgh |
| 2004/0210297 A1 | 10/2004 | Lin et al. |
| 2004/0215190 A1 | 10/2004 | Nguyen et al. |
| 2004/0215193 A1 | 10/2004 | Shaolia et al. |
| 2004/0215343 A1 | 10/2004 | Hochschuler et al. |
| 2004/0215344 A1 | 10/2004 | Hochschuler et al. |
| 2004/0220577 A1 | 11/2004 | Cragg et al. |
| 2004/0220580 A1 | 11/2004 | Johnson et al. |
| 2004/0220593 A1 | 11/2004 | Greenhalgh |
| 2004/0220615 A1 | 11/2004 | Lin et al. |
| 2004/0220672 A1 | 11/2004 | Shadduck |
| 2004/0225296 A1 | 11/2004 | Reiss et al. |
| 2004/0230198 A1 | 11/2004 | Manzi et al. |
| 2004/0249382 A1 | 12/2004 | Olson et al. |
| 2005/0010297 A1 | 1/2005 | Watson et al. |
| 2005/0013194 A1 | 1/2005 | Vaage et al. |
| 2005/0033292 A1 | 2/2005 | Teitelbaum et al. |
| 2005/0033360 A1 | 2/2005 | Sing et al. |
| 2005/0038432 A1 | 2/2005 | Shaolian et al. |
| 2005/0038514 A1 | 2/2005 | Helm et al. |
| 2005/0043733 A1 | 2/2005 | Eisermann et al. |
| 2005/0043737 A1 | 2/2005 | Reiley et al. |
| 2005/0049681 A1 | 3/2005 | Greenhalgh et al. |
| 2005/0055047 A1 | 3/2005 | Greenhalgh |
| 2005/0055094 A1 | 3/2005 | Kuslich |
| 2005/0070908 A1 | 3/2005 | Cragg |
| 2005/0085903 A1 | 4/2005 | Lau |
| 2005/0090852 A1 | 4/2005 | Layne et al. |
| 2005/0113843 A1 | 5/2005 | Arramon |
| 2005/0113919 A1 | 5/2005 | Cragg et al. |
| 2005/0113928 A1 | 5/2005 | Cragg et al. |
| 2005/0113929 A1 | 5/2005 | Cragg et al. |
| 2005/0124999 A1 | 6/2005 | Teitelbaum et al. |
| 2005/0130929 A1 | 6/2005 | Boyd |
| 2005/0131417 A1 | 6/2005 | Ahern et al. |
| 2005/0131516 A1 | 6/2005 | Greenhalgh |
| 2005/0131529 A1 | 6/2005 | Cragg |
| 2005/0137601 A1 | 6/2005 | Assell et al. |
| 2005/0137602 A1 | 6/2005 | Assell et al. |
| 2005/0137604 A1 | 6/2005 | Assell et al. |
| 2005/0137605 A1 | 6/2005 | Assell et al. |
| 2005/0137607 A1 | 6/2005 | Assell et al. |
| 2005/0137612 A1 | 6/2005 | Assell et al. |
| 2005/0143737 A1 | 6/2005 | Pafford et al. |
| 2005/0143823 A1 | 6/2005 | Boyd et al. |
| 2005/0143827 A1 | 6/2005 | Globerman et al. |
| 2005/0149022 A1 | 7/2005 | Shaolian et al. |
| 2005/0149034 A1 | 7/2005 | Assell et al. |
| 2005/0149049 A1 | 7/2005 | Assell et al. |
| 2005/0149191 A1 | 7/2005 | Cragg et al. |
| 2005/0165406 A1 | 7/2005 | Assell et al. |
| 2005/0170120 A1 | 8/2005 | Teitelbaum et al. |
| 2005/0171552 A1 | 8/2005 | Johnson et al. |
| 2005/0182414 A1 | 8/2005 | Manzi et al. |
| 2005/0182417 A1 | 8/2005 | Pagano |
| 2005/0182418 A1 | 8/2005 | Boyd et al. |
| 2005/0187558 A1 | 8/2005 | Johnson et al. |
| 2005/0187559 A1 | 8/2005 | Raymond et al. |
| 2005/0187605 A1 | 8/2005 | Greenhalgh et al. |
| 2005/0203527 A1* | 9/2005 | Carrison ............ A61B 17/1604 606/80 |

(56) References Cited

U.S. PATENT DOCUMENTS

| | | |
|---|---|---|
| 2005/0209555 A1 | 9/2005 | Middleton et al. |
| 2005/0209595 A1 | 9/2005 | Karmon |
| 2005/0216018 A1 | 9/2005 | Sennett |
| 2005/0222605 A1 | 10/2005 | Greenhalgh et al. |
| 2005/0226417 A1 | 10/2005 | Teitelbaum et al. |
| 2005/0234453 A1 | 10/2005 | Shaolian et al. |
| 2005/0251140 A1 | 11/2005 | Shaolian et al. |
| 2005/0261684 A1 | 11/2005 | Shaolian et al. |
| 2005/0261689 A1 | 11/2005 | Lin |
| 2005/0261695 A1 | 11/2005 | Cragg et al. |
| 2005/0261781 A1 | 11/2005 | Sennett et al. |
| 2005/0267483 A1 | 12/2005 | Middleton |
| 2005/0277946 A1 | 12/2005 | Greenhalgh |
| 2005/0277978 A1 | 12/2005 | Greenhalgh |
| 2005/0278036 A1 | 12/2005 | Leonard et al. |
| 2005/0283040 A1 | 12/2005 | Greenhalgh |
| 2005/0283166 A1 | 12/2005 | Greenhalgh |
| 2006/0004326 A1 | 1/2006 | Collins et al. |
| 2006/0004455 A1 | 1/2006 | Leonard et al. |
| 2006/0004457 A1 | 1/2006 | Collins et al. |
| 2006/0004458 A1 | 1/2006 | Collins et al. |
| 2006/0009778 A1 | 1/2006 | Collins et al. |
| 2006/0009779 A1 | 1/2006 | Collins et al. |
| 2006/0009799 A1 | 1/2006 | Kleshinski et al. |
| 2006/0009851 A1 | 1/2006 | Collins et al. |
| 2006/0020287 A1 | 1/2006 | Lee et al. |
| 2006/0028986 A1 | 2/2006 | Kwon et al. |
| 2006/0036276 A1 | 2/2006 | Nguyen et al. |
| 2006/0052800 A1 | 3/2006 | Greenhalgh |
| 2006/0058800 A1 | 3/2006 | Ainsworth et al. |
| 2006/0058807 A1 | 3/2006 | Landry et al. |
| 2006/0058880 A1 | 3/2006 | Wysocki et al. |
| 2006/0064101 A1 | 3/2006 | Arramon |
| 2006/0064164 A1* | 3/2006 | Thelen ................ A61B 17/164 623/16.11 |
| 2006/0089715 A1 | 4/2006 | Truckai et al. |
| 2006/0095074 A1 | 5/2006 | Lee et al. |
| 2006/0095138 A1 | 5/2006 | Truckai et al. |
| 2006/0100706 A1 | 5/2006 | Shadduck et al. |
| 2006/0106305 A1 | 5/2006 | Lau |
| 2006/0106403 A1 | 5/2006 | Schaller |
| 2006/0106459 A1 | 5/2006 | Truckai et al. |
| 2006/0116690 A1 | 6/2006 | Pagano |
| 2006/0116757 A1 | 6/2006 | Lashinski et al. |
| 2006/0122622 A1 | 6/2006 | Truckai et al. |
| 2006/0122623 A1 | 6/2006 | Truckai et al. |
| 2006/0133193 A1 | 6/2006 | Arramon |
| 2006/0142779 A1 | 6/2006 | Arramon et al. |
| 2006/0142795 A1 | 6/2006 | Nguyen et al. |
| 2006/0149268 A1 | 7/2006 | Truckai et al. |
| 2006/0149379 A1 | 7/2006 | Kuslich et al. |
| 2006/0161166 A1 | 7/2006 | Johnson et al. |
| 2006/0164913 A1 | 7/2006 | Arramon |
| 2006/0178694 A1 | 8/2006 | Greenhalgh et al. |
| 2006/0178743 A1 | 8/2006 | Carter |
| 2006/0184188 A1 | 8/2006 | Li et al. |
| 2006/0184192 A1 | 8/2006 | Markworth et al. |
| 2006/0195091 A1* | 8/2006 | McGraw ................ A61B 17/70 606/86 A |
| 2006/0206209 A1 | 9/2006 | Cragg et al. |
| 2006/0229625 A1* | 10/2006 | Truckai .............. A61B 17/1615 606/79 |
| 2006/0229628 A1 | 10/2006 | Truckai et al. |
| 2006/0229629 A1 | 10/2006 | Manzi et al. |
| 2006/0230986 A1 | 10/2006 | Hoffis |
| 2006/0235425 A1 | 10/2006 | Lin et al. |
| 2006/0241644 A1 | 10/2006 | Osorio et al. |
| 2006/0241671 A1 | 10/2006 | Greenhalgh |
| 2006/0264957 A1 | 11/2006 | Cragg et al. |
| 2006/0264965 A1 | 11/2006 | Shadduck et al. |
| 2006/0293663 A1 | 12/2006 | Walkenhorst et al. |
| 2006/0293748 A1 | 12/2006 | Alexander et al. |
| 2007/0010717 A1 | 1/2007 | Cragg |
| 2007/0010844 A1 | 1/2007 | Gong et al. |
| 2007/0010845 A1 | 1/2007 | Gong et al. |
| 2007/0016194 A1 | 1/2007 | Shaolian et al. |
| 2007/0016283 A1 | 1/2007 | Greenhalgh et al. |
| 2007/0021737 A1 | 1/2007 | Lee |
| 2007/0032791 A1 | 2/2007 | Greenhalgh |
| 2007/0055260 A1 | 3/2007 | Cragg |
| 2007/0055261 A1 | 3/2007 | Reiley et al. |
| 2007/0055266 A1 | 3/2007 | Osorio et al. |
| 2007/0055275 A1 | 3/2007 | Schaller |
| 2007/0055285 A1 | 3/2007 | Osorio et al. |
| 2007/0066977 A1 | 3/2007 | Assell et al. |
| 2007/0067034 A1 | 3/2007 | Chirico et al. |
| 2007/0100367 A1 | 5/2007 | Quijano et al. |
| 2007/0100368 A1 | 5/2007 | Quijano et al. |
| 2007/0100369 A1 | 5/2007 | Cragg et al. |
| 2007/0100452 A1 | 5/2007 | Prosser |
| 2007/0112427 A1 | 5/2007 | Christy et al. |
| 2007/0123877 A1 | 5/2007 | Goldin et al. |
| 2007/0123936 A1 | 5/2007 | Goldin et al. |
| 2007/0129669 A1 | 6/2007 | Lin et al. |
| 2007/0129670 A1 | 6/2007 | Lin et al. |
| 2007/0142765 A1 | 6/2007 | Lin et al. |
| 2007/0149994 A1 | 6/2007 | Sosnowski et al. |
| 2007/0185231 A1 | 8/2007 | Liu et al. |
| 2007/0197861 A1 | 8/2007 | Reiley et al. |
| 2007/0198020 A1 | 8/2007 | Reiley et al. |
| 2007/0213827 A1 | 9/2007 | Arramon |
| 2007/0219634 A1 | 9/2007 | Greenhalgh et al. |
| 2007/0233099 A1 | 10/2007 | Cragg |
| 2007/0233260 A1 | 10/2007 | Cragg |
| 2007/0244358 A1 | 10/2007 | Lee |
| 2007/0260270 A1 | 11/2007 | Assell et al. |
| 2007/0265697 A1 | 11/2007 | Goicoechea et al. |
| 2007/0276430 A1 | 11/2007 | Lee et al. |
| 2007/0282371 A1 | 12/2007 | Lee et al. |
| 2007/0282373 A1 | 12/2007 | Ashby et al. |
| 2008/0004647 A1* | 1/2008 | To ........................ A61B 17/22 606/159 |
| 2008/0004707 A1 | 1/2008 | Cragg et al. |
| 2008/0015631 A1 | 1/2008 | Lee et al. |
| 2008/0015639 A1 | 1/2008 | Bjork et al. |
| 2008/0027456 A1 | 1/2008 | Truckai et al. |
| 2008/0027542 A1 | 1/2008 | McQuillan et al. |
| 2008/0045881 A1 | 2/2008 | Teitelbaum et al. |
| 2008/0045922 A1 | 2/2008 | Cragg et al. |
| 2008/0046000 A1 | 2/2008 | Lee et al. |
| 2008/0065076 A1 | 3/2008 | Cragg et al. |
| 2008/0065083 A1 | 3/2008 | Assell et al. |
| 2008/0065092 A1 | 3/2008 | Assell et al. |
| 2008/0065093 A1 | 3/2008 | Assell et al. |
| 2008/0065094 A1 | 3/2008 | Assell et al. |
| 2008/0065116 A1 | 3/2008 | Lee et al. |
| 2008/0065190 A1 | 3/2008 | Osorio et al. |
| 2008/0071278 A1 | 3/2008 | Assell et al. |
| 2008/0071281 A1 | 3/2008 | Wilson et al. |
| 2008/0071282 A1 | 3/2008 | Assell et al. |
| 2008/0071283 A1 | 3/2008 | Osorio et al. |
| 2008/0071356 A1 | 3/2008 | Greenhalgh et al. |
| 2008/0086133 A1 | 4/2008 | Kuslich et al. |
| 2008/0097332 A1 | 4/2008 | Greenhalgh et al. |
| 2008/0097511 A1 | 4/2008 | Yuan et al. |
| 2008/0113008 A1 | 5/2008 | Roche |
| 2008/0114364 A1 | 5/2008 | Goldin et al. |
| 2008/0119858 A1 | 5/2008 | Potash |
| 2008/0119886 A1 | 5/2008 | Greenhalgh et al. |
| 2008/0132899 A1 | 6/2008 | Shadduck et al. |
| 2008/0154304 A1 | 6/2008 | Crawford et al. |
| 2008/0161825 A1 | 7/2008 | Greenhalgh et al. |
| 2008/0161854 A1 | 7/2008 | Bae et al. |
| 2008/0167657 A1 | 7/2008 | Greenhalgh |
| 2008/0172060 A1 | 7/2008 | Collins et al. |
| 2008/0183105 A1 | 7/2008 | Greenhalgh et al. |
| 2008/0183204 A1 | 7/2008 | Greenhalgh et al. |
| 2008/0195112 A1 | 8/2008 | Liu et al. |
| 2008/0200915 A1* | 8/2008 | Globerman ........ A61B 17/1637 606/80 |
| 2008/0249481 A1* | 10/2008 | Crainich ............ A61B 17/1617 604/264 |
| 2008/0255420 A1 | 10/2008 | Lee et al. |
| 2008/0262492 A1 | 10/2008 | Lee |

(56) References Cited

U.S. PATENT DOCUMENTS

| | | |
|---|---|---|
| 2008/0262537 A1 | 10/2008 | Lee et al. |
| 2008/0269727 A1 | 10/2008 | Lee |
| 2008/0269761 A1 | 10/2008 | Truckai et al. |
| 2008/0269766 A1 | 10/2008 | Justis |
| 2008/0281346 A1 | 11/2008 | Greenhalgh et al. |
| 2008/0281364 A1 | 11/2008 | Chirico et al. |
| 2008/0294191 A1 | 11/2008 | Lee |
| 2008/0294204 A1 | 11/2008 | Chirico et al. |
| 2009/0005782 A1 | 1/2009 | Chirico et al. |
| 2009/0005821 A1 | 1/2009 | Chirico et al. |
| 2009/0012564 A1 | 1/2009 | Chirico et al. |
| 2009/0023995 A1 | 1/2009 | Lee |
| 2009/0069842 A1 | 3/2009 | Lee et al. |
| 2009/0171147 A1 | 7/2009 | Lee et al. |
| 2009/0177206 A1* | 7/2009 | Lozier .............. A61B 17/1617 606/93 |
| 2009/0216250 A1 | 8/2009 | Souza et al. |
| 2009/0234398 A1 | 9/2009 | Chirico et al. |

FOREIGN PATENT DOCUMENTS

| | | |
|---|---|---|
| EP | 1308134 B1 | 5/2003 |
| EP | 1463464 B1 | 10/2004 |
| EP | 1498079 A1 | 1/2005 |
| JP | 2003180700 A | 7/2003 |
| NE | 9001858 | 3/1992 |
| NE | 1009471 | 3/2000 |
| WO | 9304634 | 3/1993 |
| WO | 9826725 | 6/1998 |
| WO | 9962416 | 12/1999 |
| WO | 0100408 A1 | 1/2001 |
| WO | 0160270 A1 | 8/2001 |
| WO | 0226170 A2 | 4/2002 |
| WO | 0300951 A1 | 1/2003 |
| WO | 03057088 A1 | 7/2003 |
| WO | 03101308 A1 | 12/2003 |
| WO | 2004043302 A1 | 5/2004 |
| WO | 200502224 A2 | 11/2005 |
| WO | 2006028986 A2 | 3/2006 |
| WO | 2006060420 A1 | 6/2006 |
| WO | 2008076357 A1 | 6/2008 |

OTHER PUBLICATIONS

Cavity Creation Curette Set, Website of AO Foundation (http://www.aofoundation.org) printed Feb. 13, 2005.

Verdult, "Drilling Back Design and Development of a Directional Drilling Device/New Spinal Anchoring Technique" Dissertation, Delft University of Technology, The Netherlands, Dec. 1998.

Optimesh 500 E—Extrapedicular Surgical Technique for Vertebral Stabilization, Spineology Inc., Jun. 24, 2003, p. 1-23.

Vallejo et al. (2005) "Percutaneous Cement Injection into a Created Cavity for the Treatment of Vertebral Body Fracture", Clin. J. Pain, 22:182-89.

Chiu et al., (2005)"Percutaneous Vertebral Augumentation and Reconstruction with an Intravertebral Mesh and Morcelized Bond Graft" The Internet Journal of Spine Surgery (website:http://www.ispub.com/ostia/Index.php?xmlFilePath=journals/ljss/vol2n1/spine.xml) printed Oct. 4, 2007.

Optimesh Surgical Mesh System, Technical Monograph, 2003 Spineology Inc. p. 1-10.

Furderer et al. "Vertebral Body Stenting ( A method for repositioning and augmenting vertebral body compression fractures)" Der Orthopaedic Apr. 2002, 356-361.

Chapter 5,"The Circular Trajectory Drill", Chapter Survey, pp. 163-279.

* cited by examiner

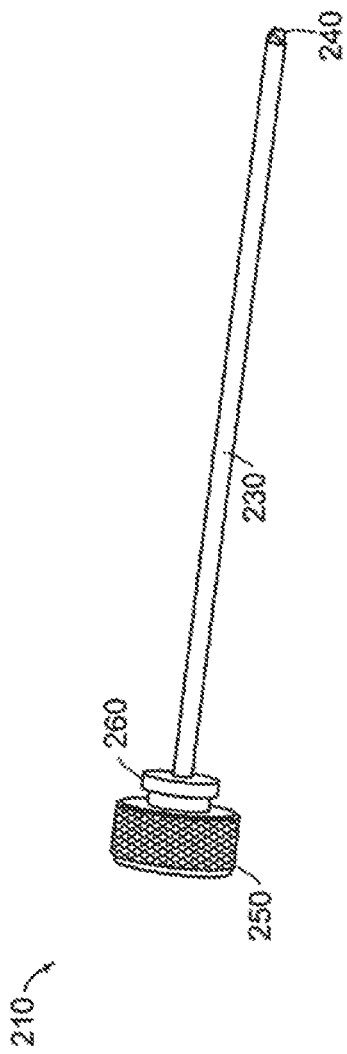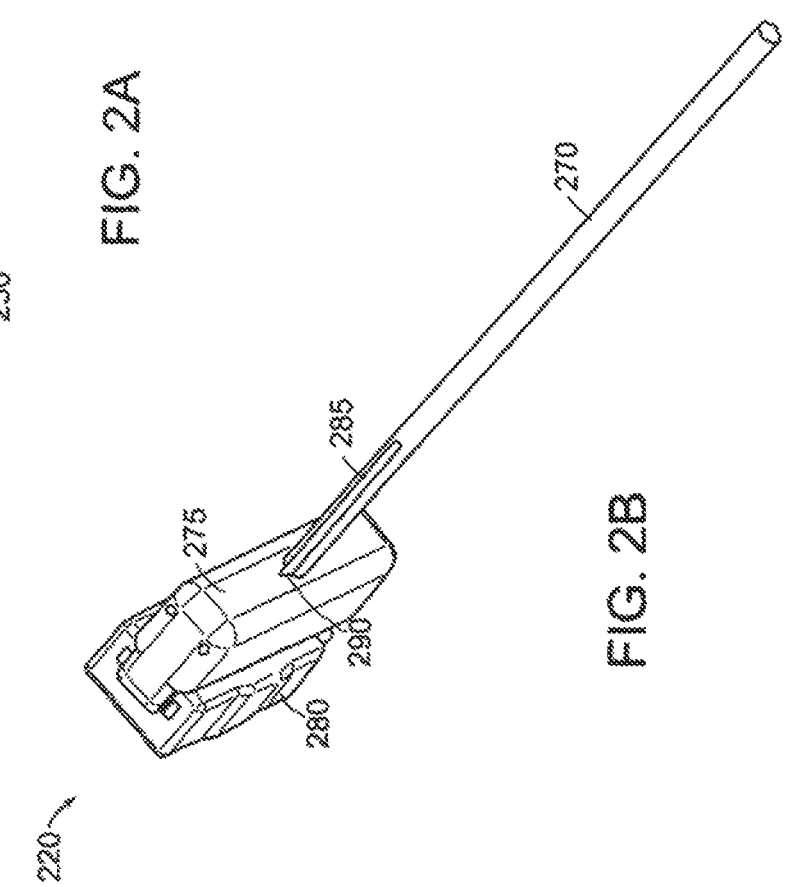
FIG. 2A
FIG. 2B

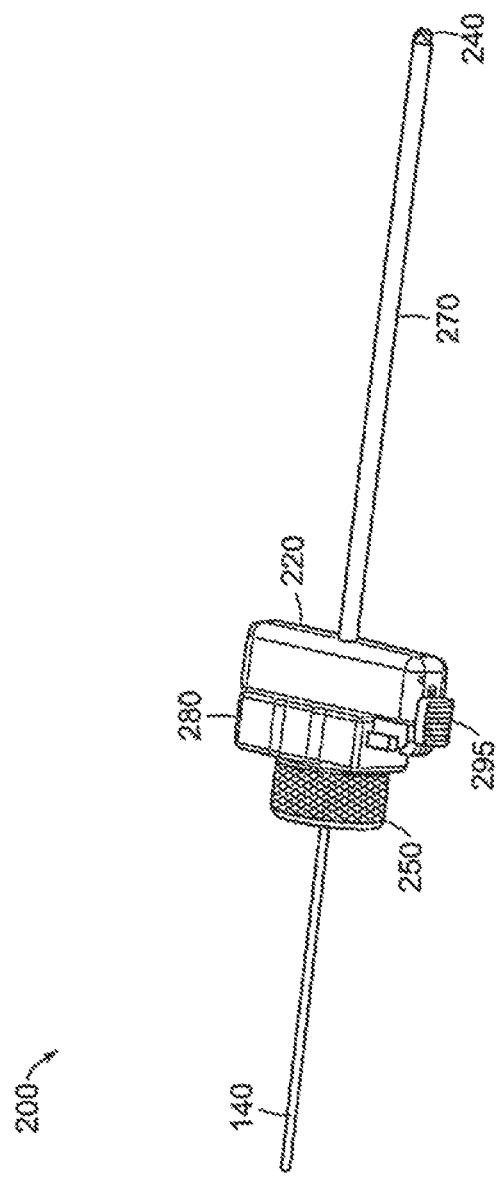

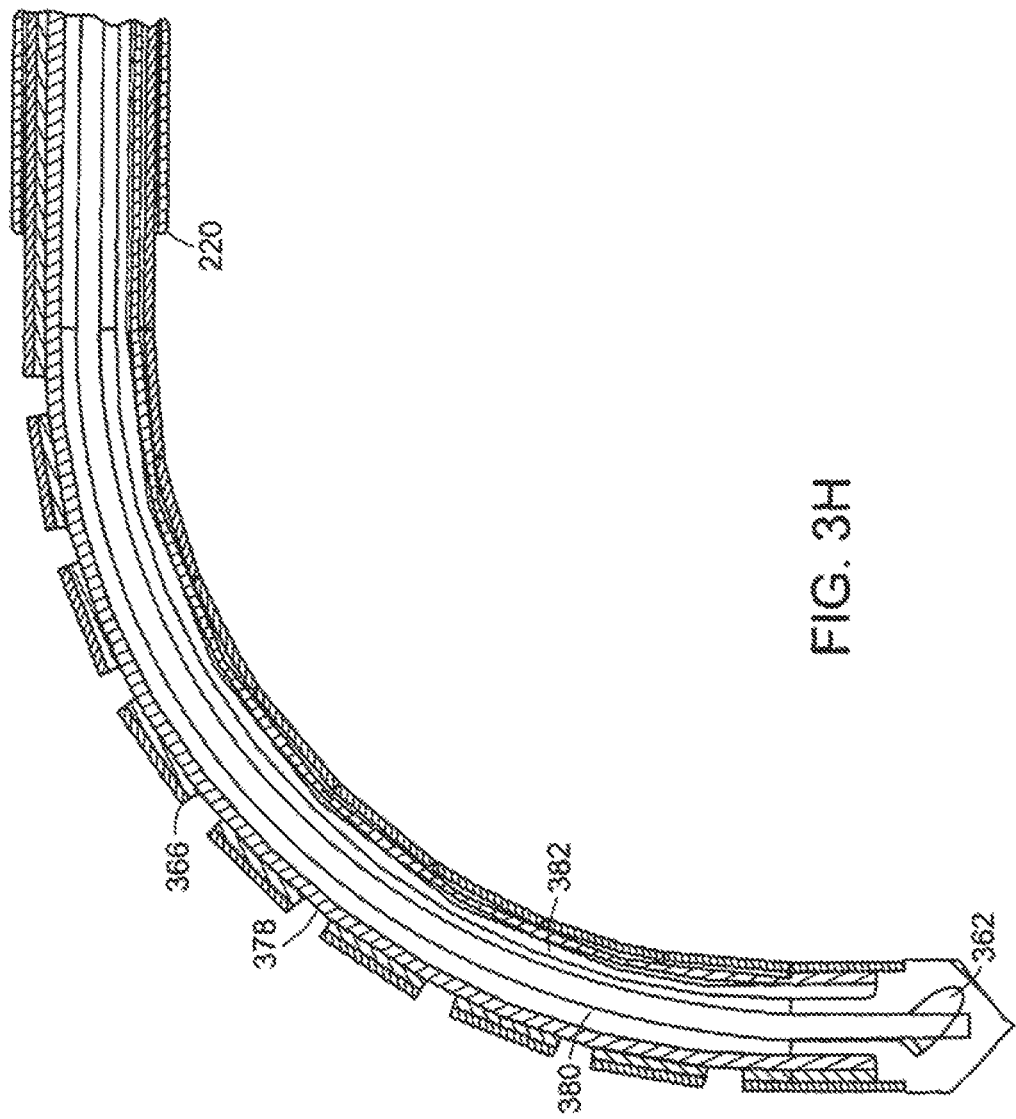

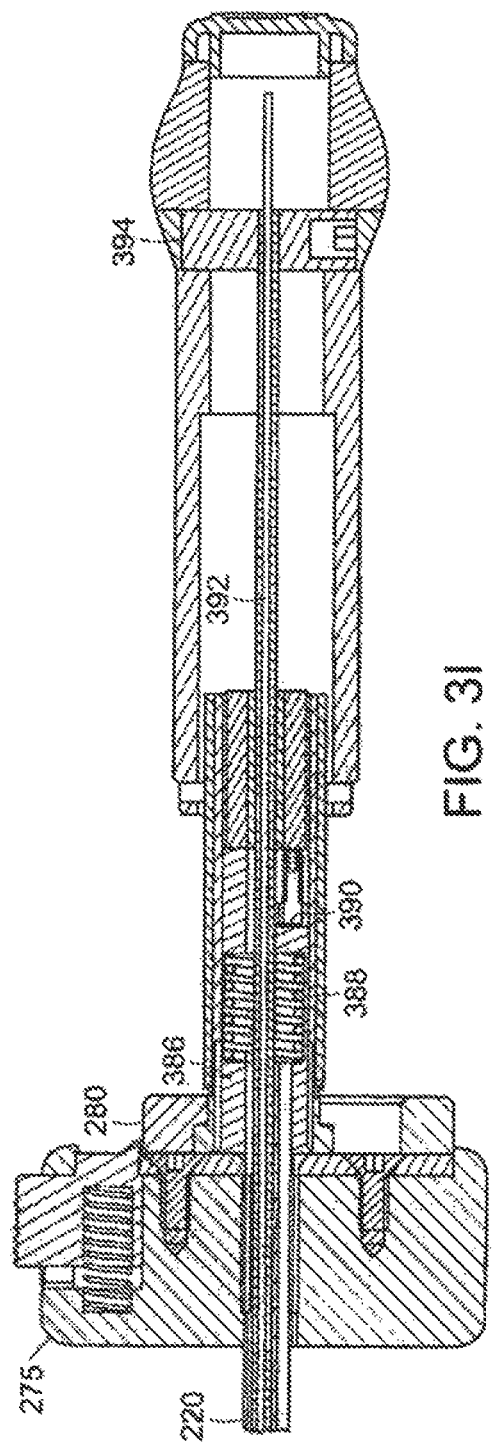

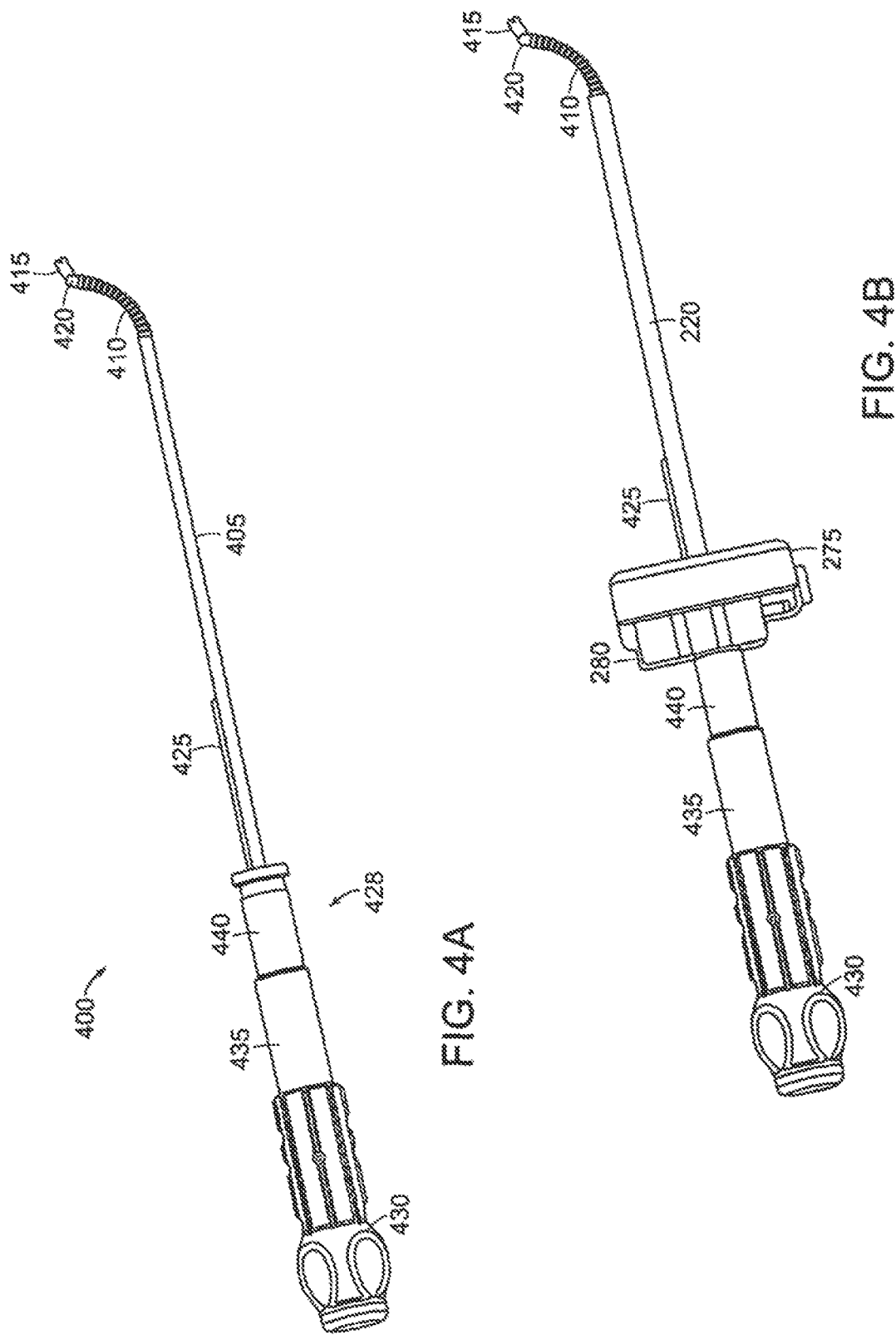

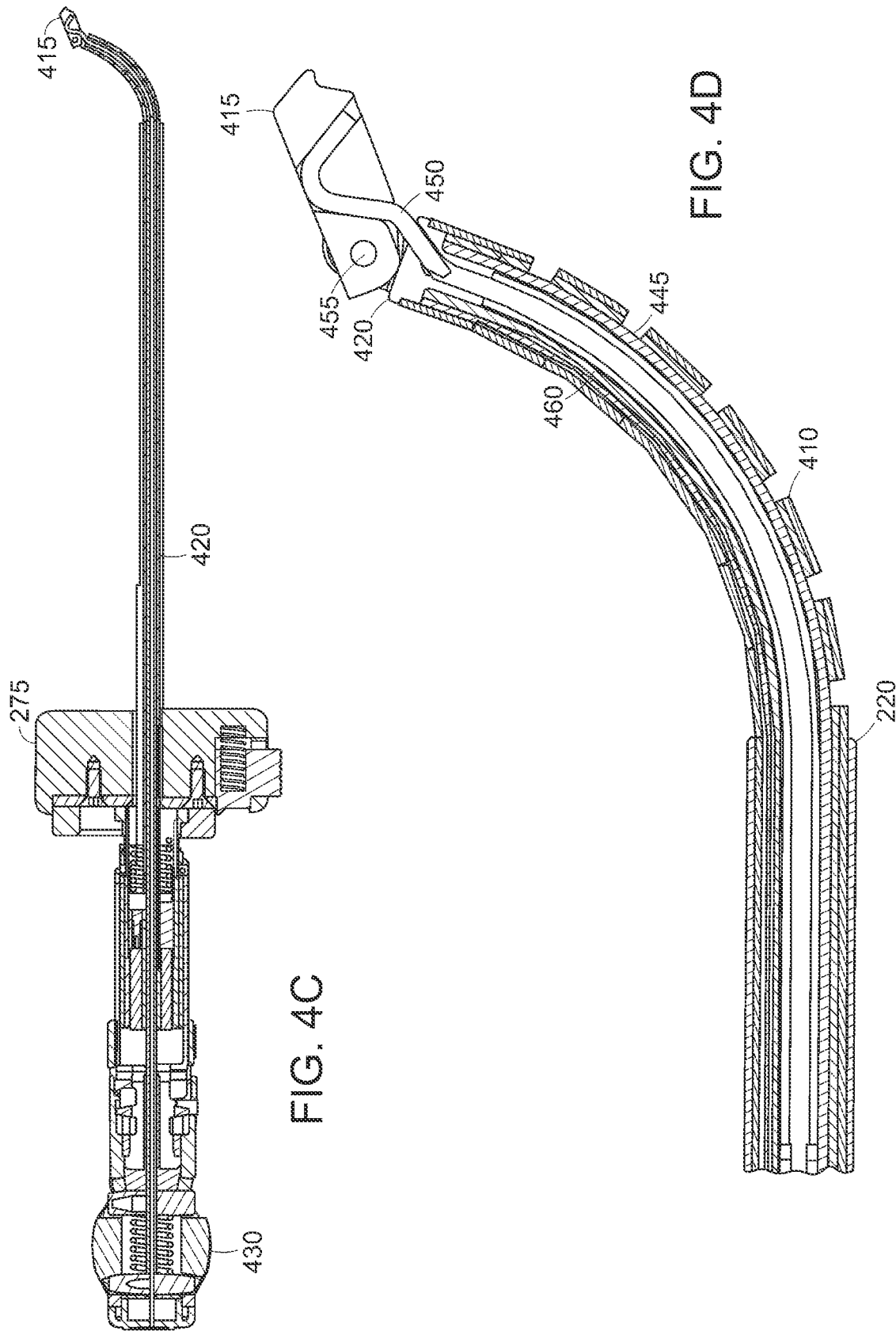

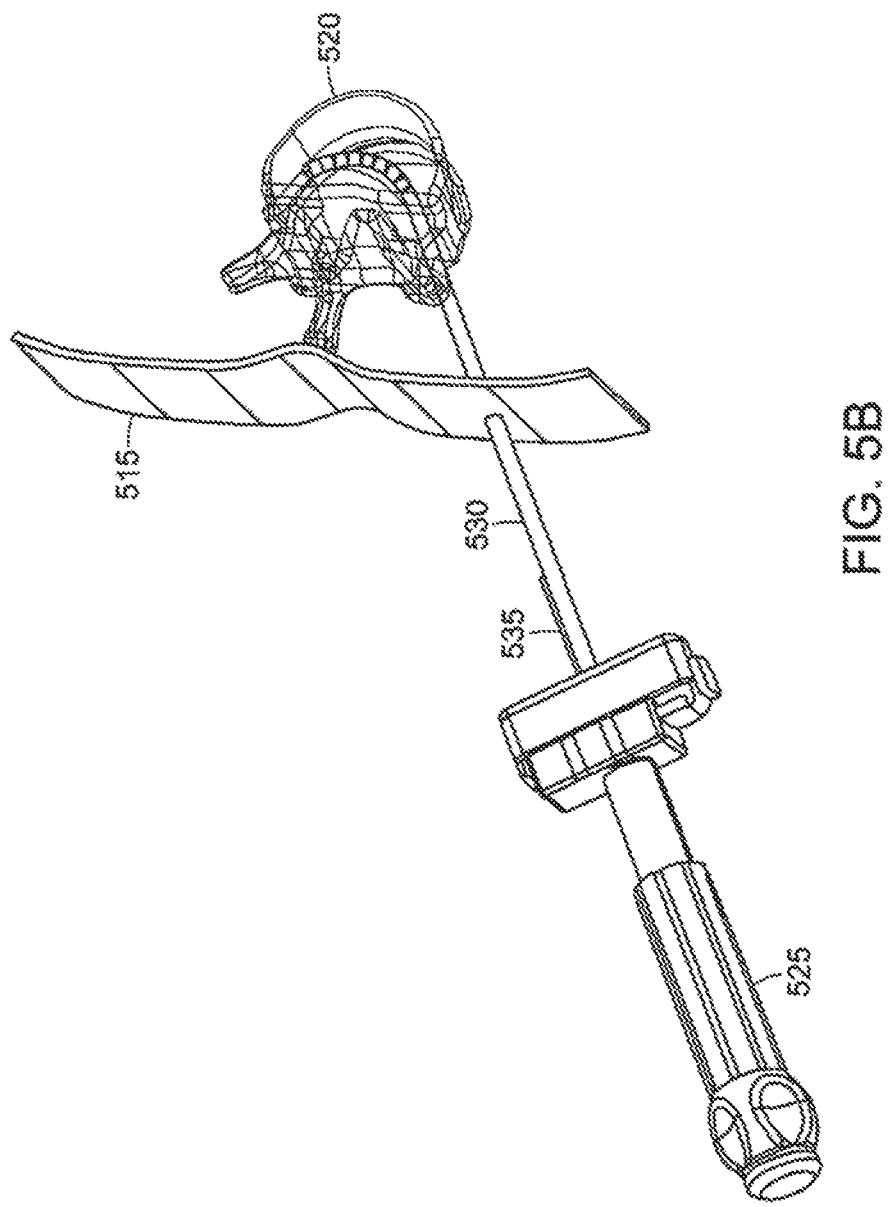

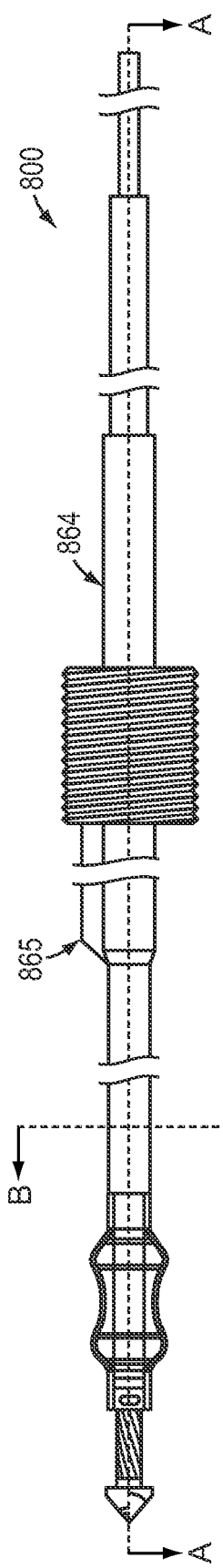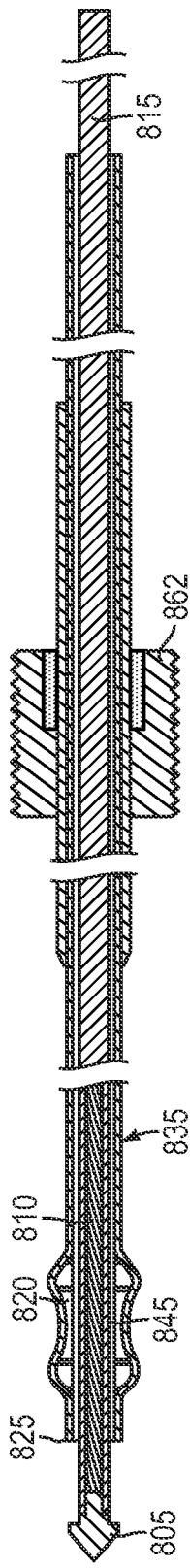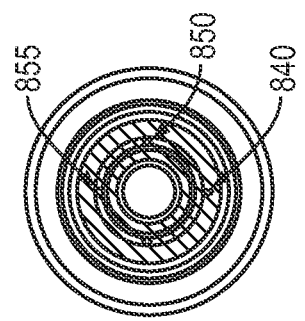
FIG. 8A
FIG. 8B
FIG. 8C

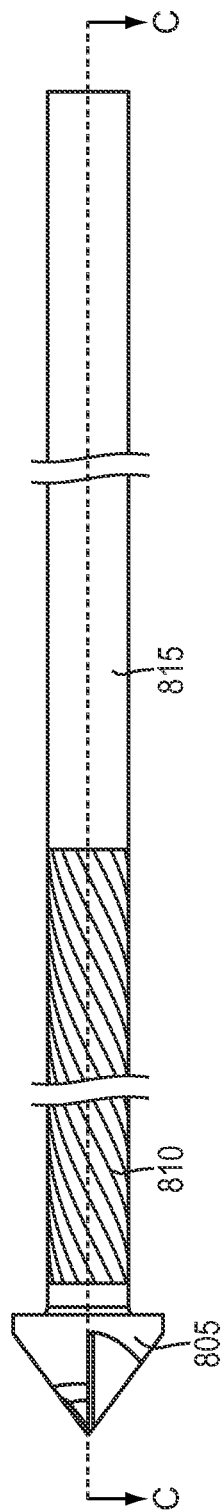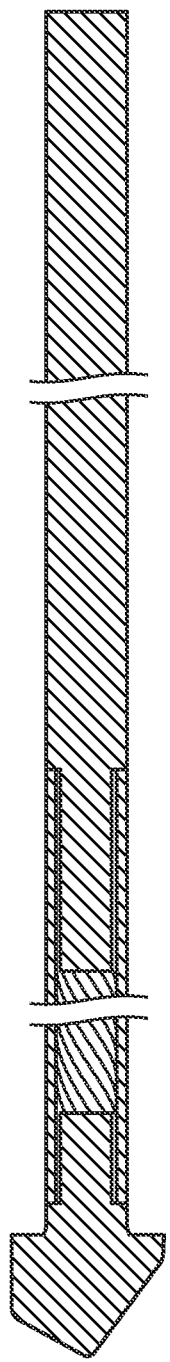
FIG. 8D
FIG. 8E

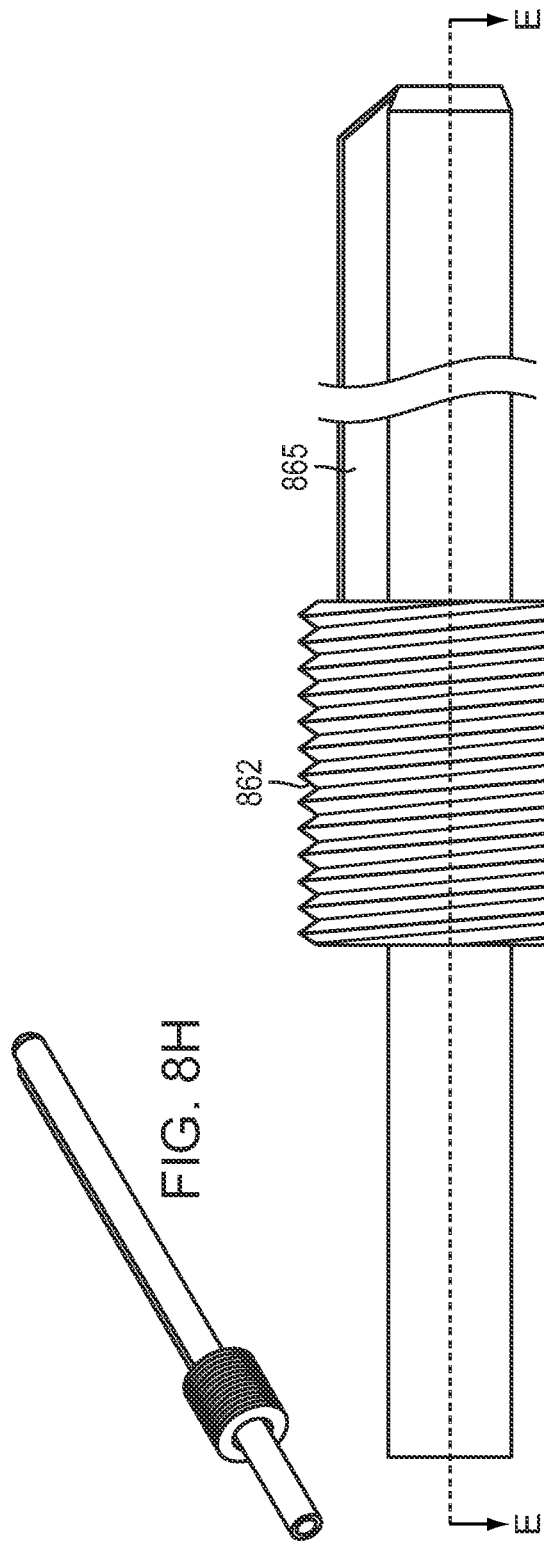
FIG. 8H
FIG. 8I
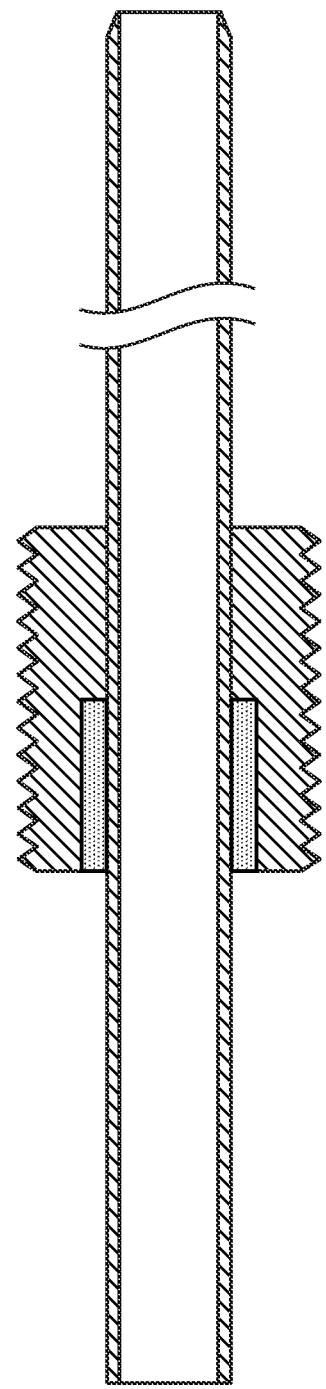
FIG. 8J

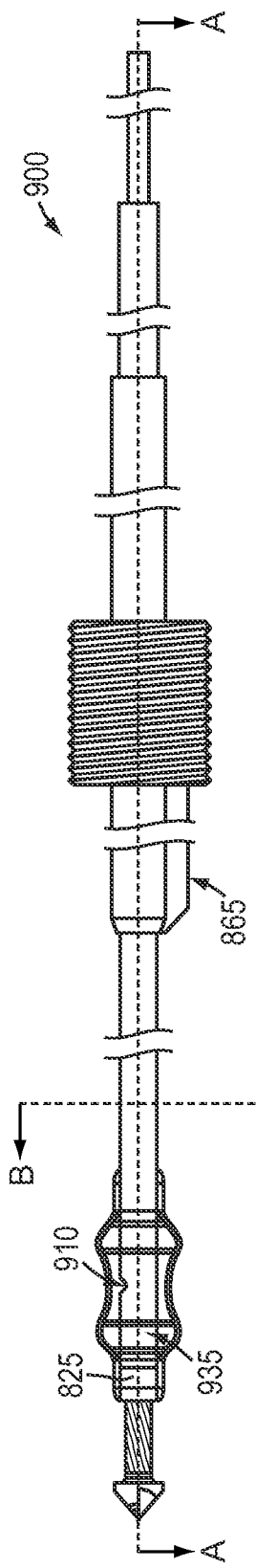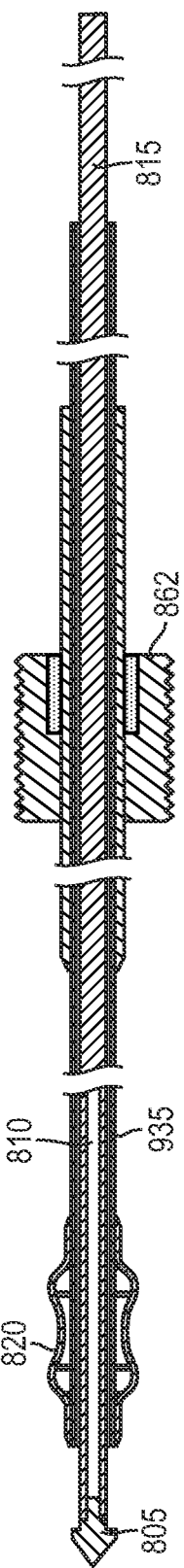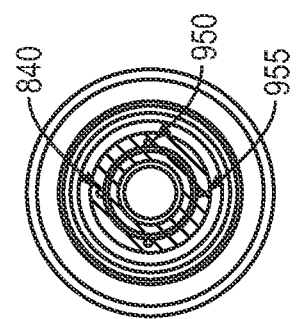
FIG. 9A
FIG. 9B
FIG. 9C

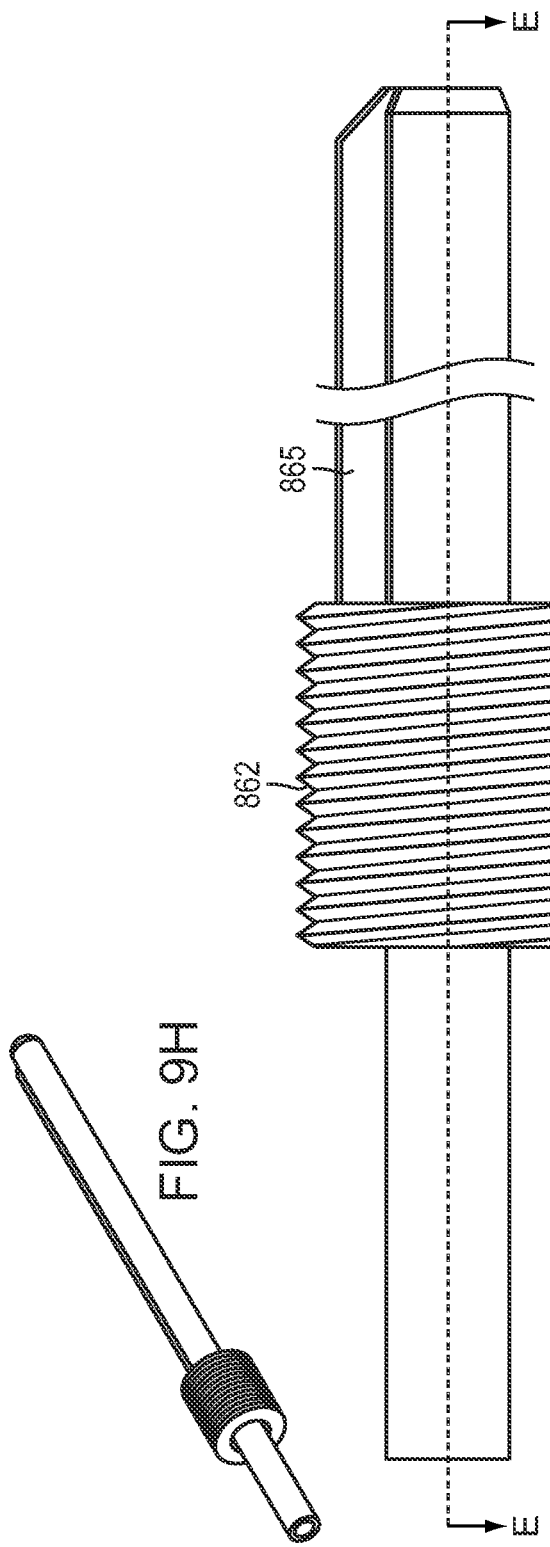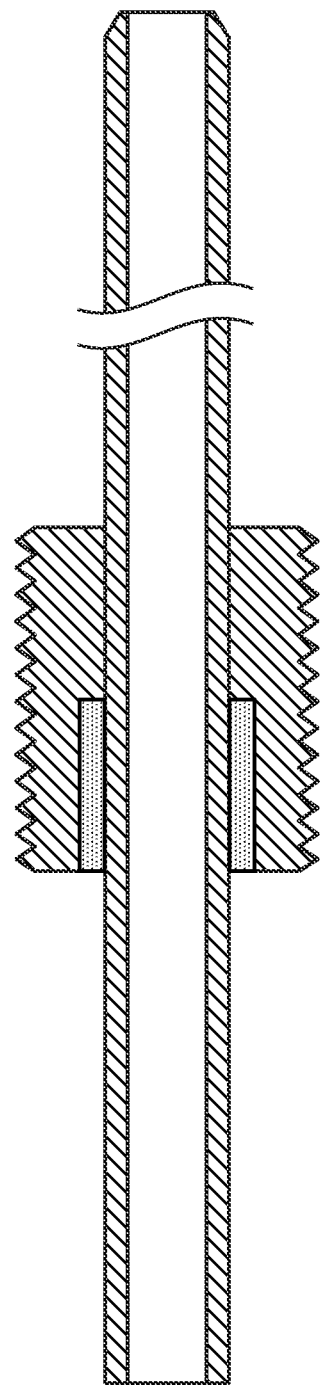

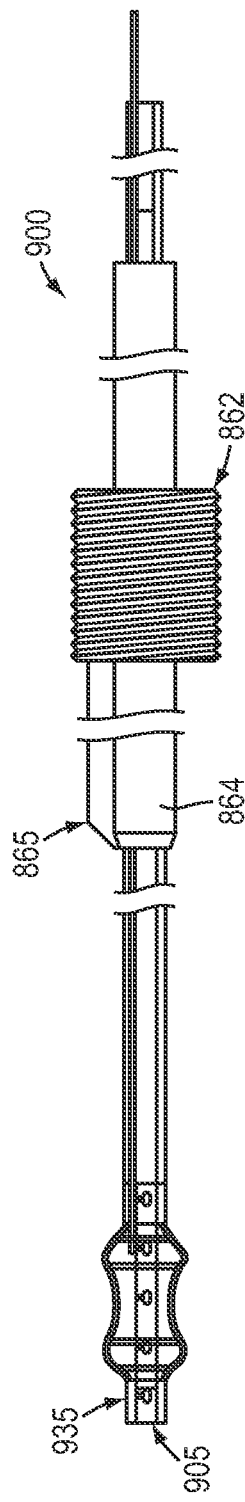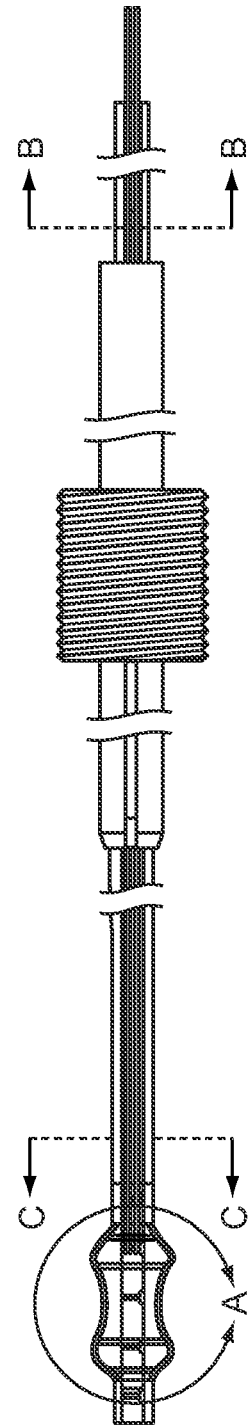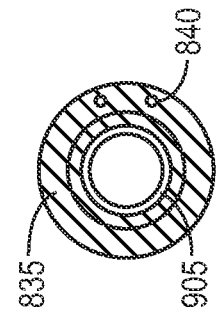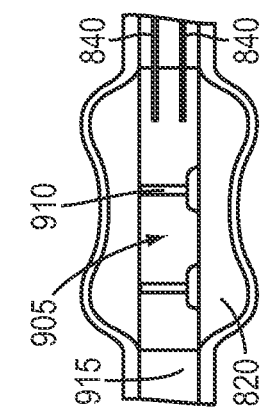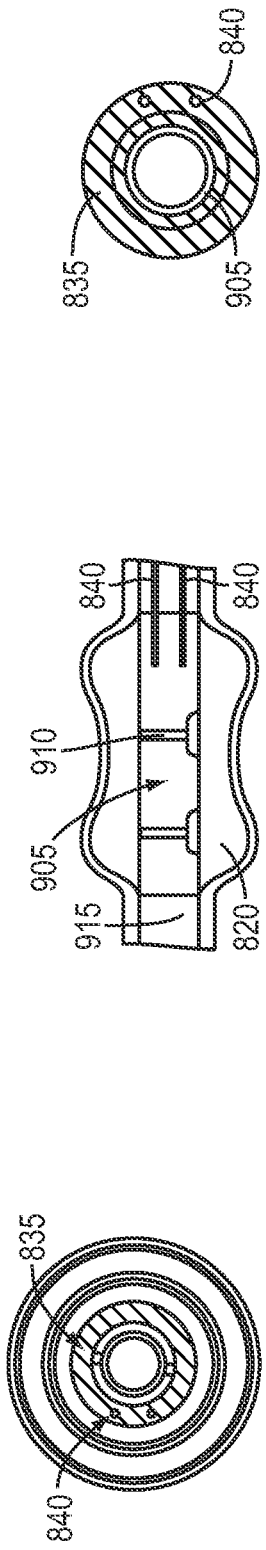

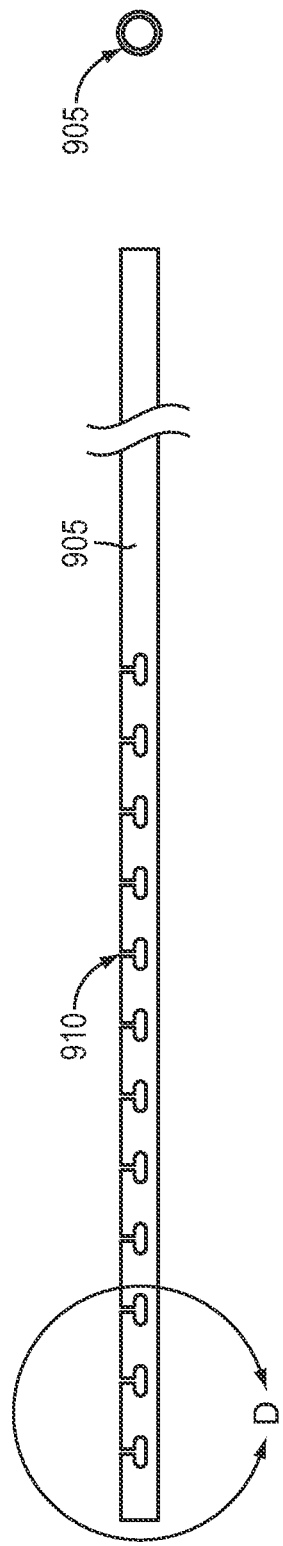
FIG. 10F
FIG. 10G
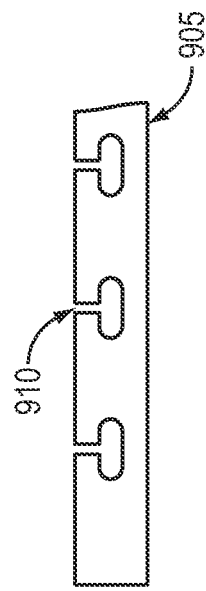
FIG. 10H

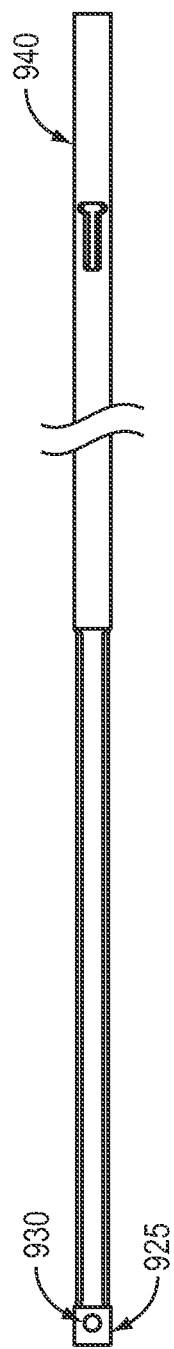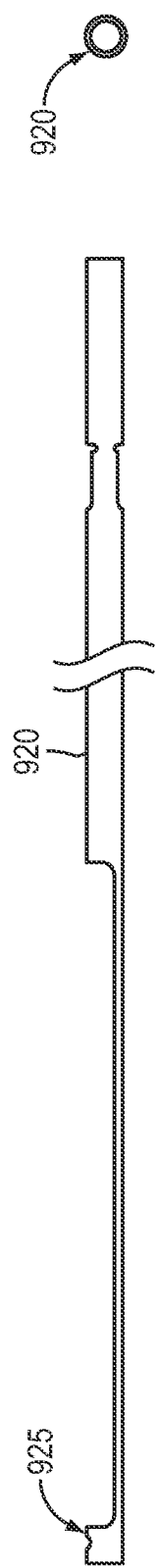
FIG. 10I
FIG. 10J
FIG. 10K

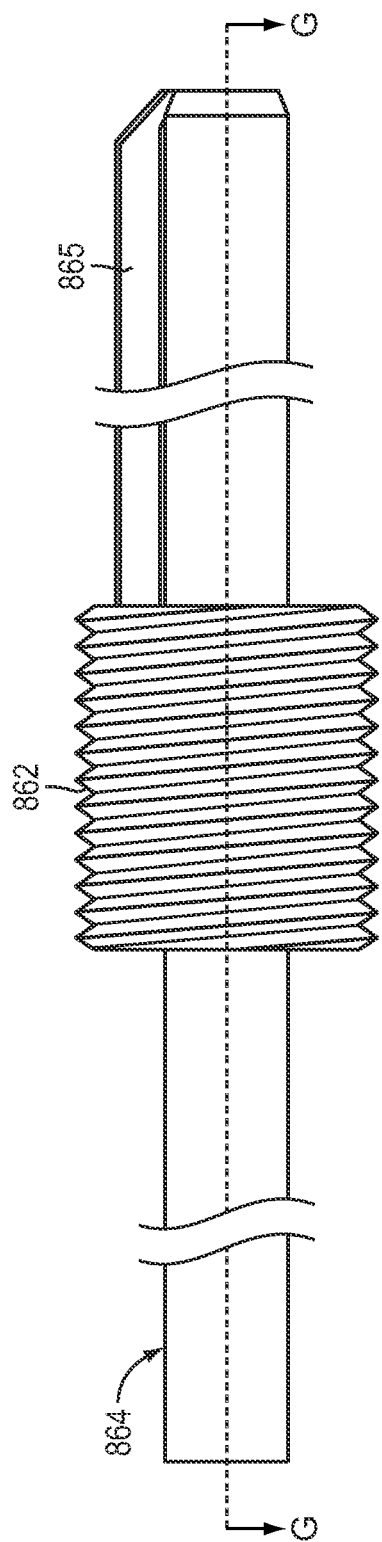
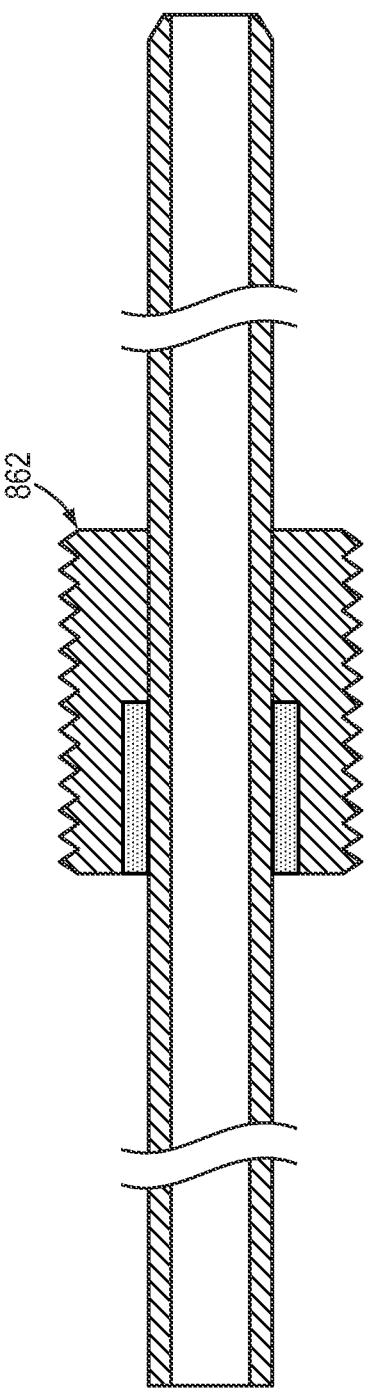

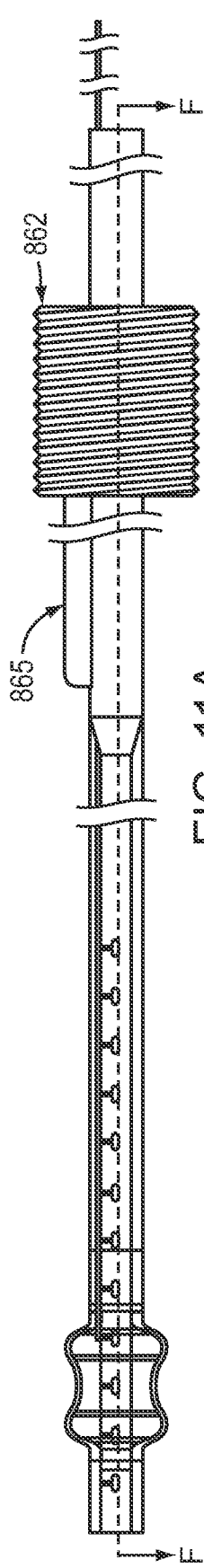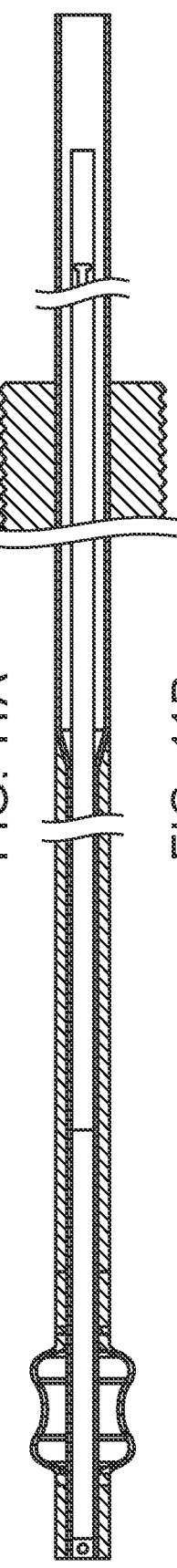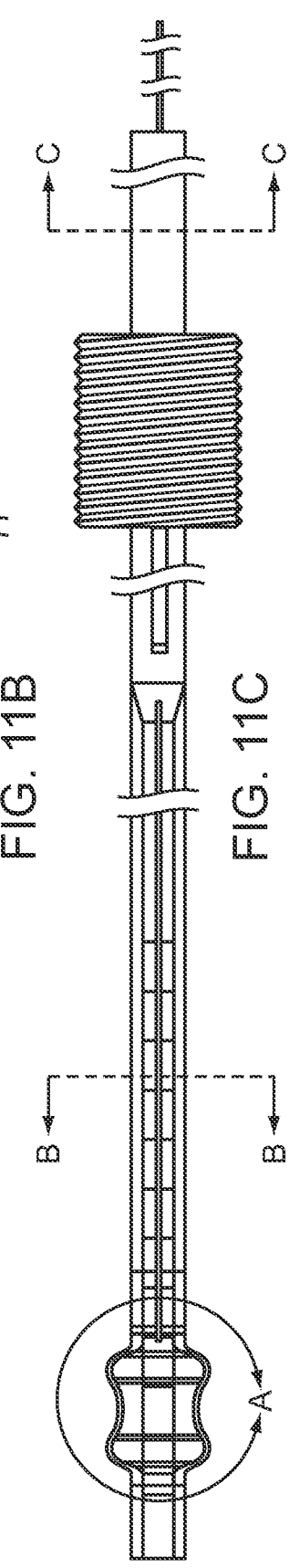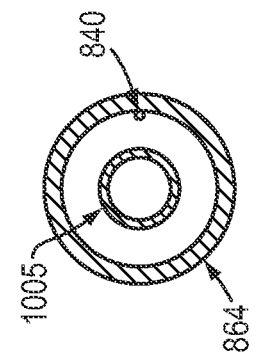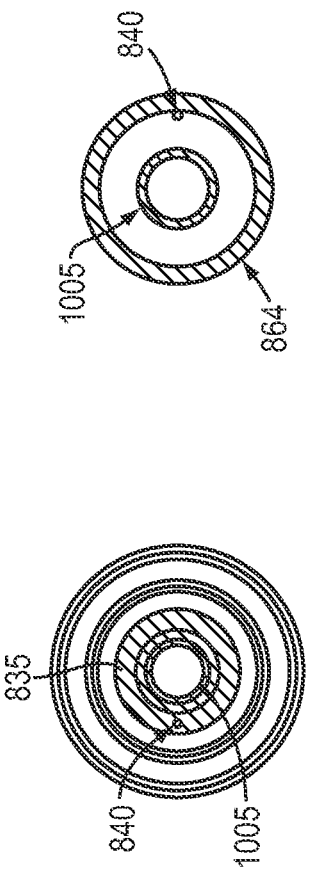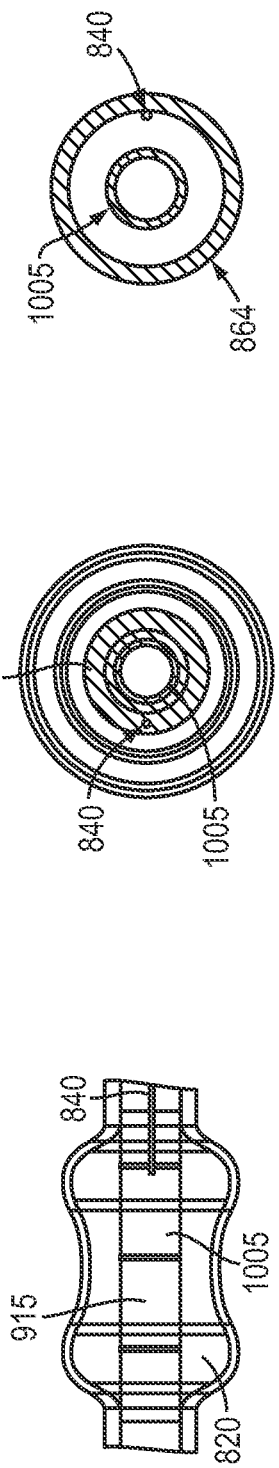
FIG. 11A
FIG. 11B
FIG. 11C
FIG. 11D
FIG. 11E
FIG. 11F

DEVICES AND METHODS FOR FRACTURE REDUCTION

CROSS-REFERENCE TO RELATED APPLICATIONS

The present application is a continuation patent application of U.S. patent application Ser. No. 14/881,252, filed on Oct. 13, 2015 (published as U.S. Patent Publication No. 2016-0074046), which is a divisional of U.S. patent application Ser. No. 12/486,439, filed on Jun. 17, 2009 (now issued as U.S. Pat. No. 9,192,397), which claims priority to and the benefit of U.S. provisional patent application Ser. No. 61/073,184 filed Jun. 17, 2008. The previous applications are hereby incorporated by reference in their entirety.

FIELD OF THE INVENTION

The present invention relates generally to the field of orthopedic devices to treat fractured bone in the spine, and more particularly to an orthopedic instrument and implant system that can be used to facilitate bone cement treatment of a vertebral compression fracture.

BACKGROUND OF THE INVENTION

There are many disease states that cause bone defects in the spinal column. For instance, osteoporosis and other metabolic bone conditions weaken the bone structure and predispose the bone to fracture. If not treated, certain fractures and bone defects of the vertebral body may produce intolerable pain, and may lead to the development of deformity and severe medical complications.

Bone weakening may also result from benign or malignant lesions of the spinal column. Tumors often compromise the structural integrity of the bone and thus require surgical stabilization and repair of defects with biocompatible materials such as bone grafts or cements. Bone tumors of the spine are relatively common, and many cause vertebral compression fracture More than 700,000 osteoporotic compression fractures of the vertebrae occur each year in the United States—primarily in the elderly female population. Until recently, treatment of such fractures was limited to conservative, non-operative therapies such as bed rest, bracing, and medications.

One surgical technique for treating vertebral compression fracture can include injecting or filling the fracture bone or bone defect with biocompatible bone cement. A relatively new procedure known as "vertebroplasty" was developed in the mid 1980's to address the inadequacy of conservative treatment for vertebral body fracture. This procedure involves injecting radio-opaque bone cement directly into a fracture void, through a minimally invasive cannula or needle, under fluoroscopic control. The cement is pressurized by a syringe or similar plunger mechanism, thus causing the cement to fill the void and penetrate the interstices of a broken trabecular bone. Once cured, the cement stabilizes the fracture and eliminates or reduces pain. Bone cements are generally formulations of non-resorbable biocompatible polymers such as PMMA (polymethylmethacrylate), or resorbable calcium phosphate cements which allow for the gradual replacement of the cement with living bone. Both types of bone cements have been used successfully in the treatment of bone defects secondary to compression fractures of the vertebral body.

One technique which has gained popularity in recent years is a modified vertebroplasty technique in which a "balloon tamp" is inserted into the vertebral body via a cannula approach to expand or distract the fractured bone and create a void within the cancellous structure. Balloon tamps are inflated using pressurized fluid such as saline solution. The inflation of a balloon membrane within the bone produces radial expansion forces on the surface of the membrane and forms a cavity in the bone. When deflated and removed, the membrane leaves a cavity that is subsequently filled with bone cement. The formation of a cavity within the bone allows for the injection of more viscous cement material, which may be relatively less prone to leakage.

In certain instances, such as the treatment of acute or mobile fractures, the balloon is also effective at "reducing" the fracture and restoring anatomic shape to a fractured body. In particular, balloon dilatation in bone is maximally effective if the balloon device is targeted inferior to, or below, the fracture plane. In this instance, the balloon dilatation may distract, or lift, a fracture bone fragment, such as the vertebral body endplate.

One limitation to the use of such balloon dilatation has been the difficulty in effectively targeting the location within the bone at which the cavity should be created prior to dilatation of the balloon. In the specific case of vertebral body fracture, there are anatomical challenges to targeting with minimally invasive instrumentation. Safe passage of instruments and balloon catheters from the posterior surgical approach is generally achieved through a straight cannula positioned within the pedicle of the vertebral body, or just lateral to the pedicle to avoid potentially dangerous penetration of the cannula in the spinal canal. This anatomically defined trajectory often does not align with, or target, the fracture within the vertebral body. This limits the effectiveness of such techniques in effectively targeting a fracture.

SUMMARY OF THE INVENTION

Devices and methods including curving drill devices and curving reamer devices have been developed to improve the targeting of a fracture and forming a cavity in a more anatomically desirable location. See, for example, U.S. patent application Ser. No. 11/957,022 to Crainich et al., the disclosure of which is being incorporated herein by reference in its entirety. The purpose of the present disclosure is to define improvements in vertebroplasty instrument systems to facilitate targeting of a fracture, including novel devices and methods for distracting broken bone fragments, create a cavity, and/or treating the fracture with bone cement injection.

The present invention is directed, in one embodiment, towards novel methods and devices for preparing a cavity in bone, and/or distracting broken bone fragments. In one embodiment, the methods and devices disclosed herein can allow a cavity to be created in a vertebral body along a curvilinear pathway which has been targeted, for example, to a location including broken bone fragments.

On aspect of the invention includes a method of forming a curvilinear void in a bony structure, such as, but not limited to, a vertebral body. The method may include the steps of accessing a bony structure with a cannula, inserting a distal end of a drill device through the cannula and into the bony structure, and manipulating the distal end of the drill device to create a curvilinear void in the bony structure. The method may further include enlarging the void by expanding a balloon element mounted to the drill device and thereafter deflating the balloon element and removing the drill device from the cannula. In one embodiment the balloon element is expanded by fluid pressure.

The step of manipulating of the distal end of the drill device may include a simultaneous rotation and curvilinear translation of the distal end of the drill device. The cannula may be substantially straight or at least partially curvilinear. The drilling device may include a flexible drill shaft assembly. In one embodiment, the flexible drill shaft assembly includes a sharp cutting tip, a flexible rotatable drive shaft coupled to the tip, and a flexible, moveable and non-rotatable housing.

The drilling device may also include a locking means. In one embodiment the method may also include the steps of locking the drill device into the cannula using the locking means prior to forming the void and unlocking the drill device from the cannula after forming the void and prior to removing the distal end of the drill device. The drill device may be manipulated in response to a rotation of an element at a proximal end of the drill device. One embodiment of the method may also include the step of reaming the void produced by at least one of drilling and balloon expansion.

Another aspect of the invention may include an apparatus for forming a curvilinear void in bony structure. The apparatus may include a curvilinear drilling device with an expandable balloon element located at a distal portion of the drilling device. In one embodiment, the balloon element is expanded by injection of a fluid into an interior portion thereof.

In one embodiment the apparatus may also include a lumen in fluid communication with the balloon element. The drilling device may include a handle and a flexible drill shaft assembly extending from a distal end of the handle. The drill shaft assembly may include a cutting tip located at a distal end of the flexible drill shaft assembly, a flexible rotatable drive shaft coupled to the tip, and a flexible, moveable and non-rotatable housing. The cutting tip may be adapted to form the curvilinear void by simultaneous rotation and curvilinear translation of the cutting tip.

In one embodiment, the balloon element is located substantially proximate to a distal end of the flexible, moveable and non-rotatable housing. In one embodiment, the balloon element may be mounted to a multi-lumen assembly mounted to the drilling device. The multi-lumen assembly may include a first lumen adapted to surround an elongate shaft of the drilling device and a second lumen in fluid communication with the balloon element. The multi-lumen assembly may be removably or fixedly mounted onto the drilling device. The drill device may include at least one pull wire for applying a curvature to a distal end thereof. The drill device may further include at least one stiffening wire.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 2A is schematic perspective view of a trocar, used in accordance with one embodiment of the invention;

FIG. 2B is schematic perspective view of a cannula, in accordance with one embodiment of the invention;

FIG. 2D is a schematic perspective view of a trocar inserted with the cannula of FIG. 2B, in accordance with one embodiment of the invention;

FIG. 3H is an enlarged sectional side view of the distal end of the drill assembly of FIG. 3E;

FIG. 3I is an enlarged sectional side view of the proximal end of the drill assembly of FIG. 3E inserted within a cannula;

FIG. 4A is a schematic perspective view of a reamer assembly, in accordance with one embodiment of the invention;

FIG. 4B is a schematic perspective view of the reamer assembly of FIG. 4A inserted within a cannula, in accordance with one embodiment of the invention;

FIG. 4C is a sectional side view of the reamer assembly of FIG. 4A inserted within a cannula;

FIG. 4D is an enlarged sectional side view of the distal end of the reamer assembly of FIG. 4A;

FIG. 5B is a schematic perspective view of a drill assembly being inserted through a cannula into a vertebral body, in accordance with one embodiment of the invention;

FIG. 8A is a schematic side view of a drill assembly with balloon element, in accordance with one embodiment of the invention;

FIG. 8B is a cross-sectional bottom view of the drill assembly and balloon element of FIG. 8A through section A-A;

FIG. 8C is a cross-sectional end view of the drill assembly and balloon element of FIG. 8A through section B-B;

FIG. 8D is a schematic side view of a drill tip and shaft for the drill assembly of FIG. 8A;

FIG. 8E is a cross-sectional bottom view of the drill tip and shaft of FIG. 8D through section C-C;

FIG. 8H is a schematic perspective view of a lead-screw and key for the drill assembly and balloon element of FIG. 8A;

FIG. 8I is a schematic side view of the lead-screw and key of FIG. 8H;

FIG. 8J is a cross-sectional bottom view of the lead-screw and key of FIG. 8H through section E-E;

FIG. 9A is a schematic side view of another drill assembly with balloon element, in accordance with one embodiment of the invention;

FIG. 9B is a cross-sectional bottom view of the drill assembly and balloon element of FIG. 9A through section A-A;

FIG. 9C is a cross-sectional end view of the drill assembly and balloon element of FIG. 9A through section B-B;

FIG. 9H is a schematic perspective view of a lead-screw and key for the drill assembly and balloon element of FIG. 9A;

FIG. 9I is a schematic side view of the lead-screw and key of FIG. 9H;

FIG. 9J is a cross-sectional bottom view of the lead-screw and key of FIG. 9H through section E-E;

FIG. 10A is a schematic side view of a drill assembly with balloon element and slotted deflection shaft, in accordance with one embodiment of the invention;

FIG. 10B is a schematic top view of the drill assembly of FIG. 10A;

FIG. 10C is a cross-sectional end view of the drill assembly of FIG. 10A through section C-C;

FIG. 10D is an enlarged schematic top view of the balloon element of FIG. 10A at section A;

FIG. 10E is a cross-sectional end view of the drill assembly of FIG. 10A through section B-B;

FIG. 10F is a schematic side view of a slotted deflection shaft for the drill assembly of FIG. 10A;

FIG. 10G is a schematic end view of the slotted deflection shaft of FIG. 10F;

FIG. 10H is an enlarged schematic side view of the slotted deflection shaft portion at section D;

FIG. 10I is a schematic top view of a puller element for the drill assembly of FIG. 10A;

FIG. 10J is a schematic side view of the puller element of FIG. 10I;

FIG. 10K is a schematic end view of the puller element of FIG. 10I;

FIG. 10N is a schematic side view of a lead-screw and key for the drill assembly of FIG. 10A;

FIG. 10O is a cross-sectional bottom view of the lead-screw and key of FIG. 10N through section G-G;

FIG. 11A is a schematic side view of another drill assembly with balloon element and slotted deflection shaft, in accordance with one embodiment of the invention;

FIG. 11B is a cross-sectional bottom view of the drill assembly of FIG. 11A through section F-F;

FIG. 11C is a schematic top view of the drill assembly of FIG. 11A;

FIG. 11D is an enlarged schematic top view of the balloon element of FIG. 11A at section A;

FIG. 11E is a cross-sectional end view of the drill assembly of FIG. 11A through section B-B;

FIG. 11F is a cross-sectional end view of the drill assembly of FIG. 11A through section C-C;

DETAILED DESCRIPTION OF THE PREFERRED EMBODIMENTS

To maximize the effectiveness of balloon dilation within a fractured bone to cause distraction of the bone fragments, it may be beneficial to more effectively target the location within the bone prior to dilatation of the balloon. In the specific case of vertebral body fracture, there are anatomical challenges to targeting with minimally invasive instrumentation. Safe passage of instruments and balloon catheters from the posterior surgical approach is generally achieved through a straight cannula positioned either within the pedicle of the vertebral body or just lateral to the pedicle to avoid potentially dangerous penetration of the cannula in the spinal canal. This anatomically defined trajectory often does not align with, or target, the fracture within the vertebral body. Therefore, prior techniques are limited in their ability to effectively target the fracture.

Limitations in current balloon expanding techniques may be overcome through use of a drill device that curves to the central portion of the vertebral body, where, for example, displaced fragments most often occur, and where the benefits of distraction can be clinically realized. In addition, the expansion of a balloon element at this targeted location may be used to form a beneficial bone cavity defined, for example, by compacted bone fragments along its margins. In one embodiment, the compacted bone may provide a beneficial barrier to contain liquid cement material injected within the cavity. The containment and/or restriction of cement flow is desired to avoid complication associated from cement leakage in its liquid state beyond the vertebral body.

A second benefit of cavity formation is the ability to deploy an implant that can provide beneficial containment or partial containment of liquid cement to prevent cement leakage. One novel device, an implantable cement-directing stent device, is disclosed in U.S. Patent Publication No. 2005/0261781 A1 to Sennett et al., the disclosure of which is incorporated herein by reference in its entirety. The implantable cement-directing stent device provides a means for temporarily stabilizing a fractured vertebral body after cavity creation and/or during cement injection, while also directing the flow of cement anteriorly within the vertebral body to prevent unwanted cement flow near the spinal canal.

Surgical techniques following initial percutaneous access, and devices used to achieve improved access and therapeutic treatment of vertebral compression fracture, are described below.

Needle

In one embodiment of the invention, access to the vertebral body can be achieved using a pointed needle or wire to pierce the skin and underlying tissue and entering into the pedicle, a depression of the vertebral body, until the needle is held fast. The needle can then be pressed into the vertebral body until it is held firmly in place by the wall of the vertebral body. The needle can then become a guide for the placement of subsequent devices.

Figure 1A:
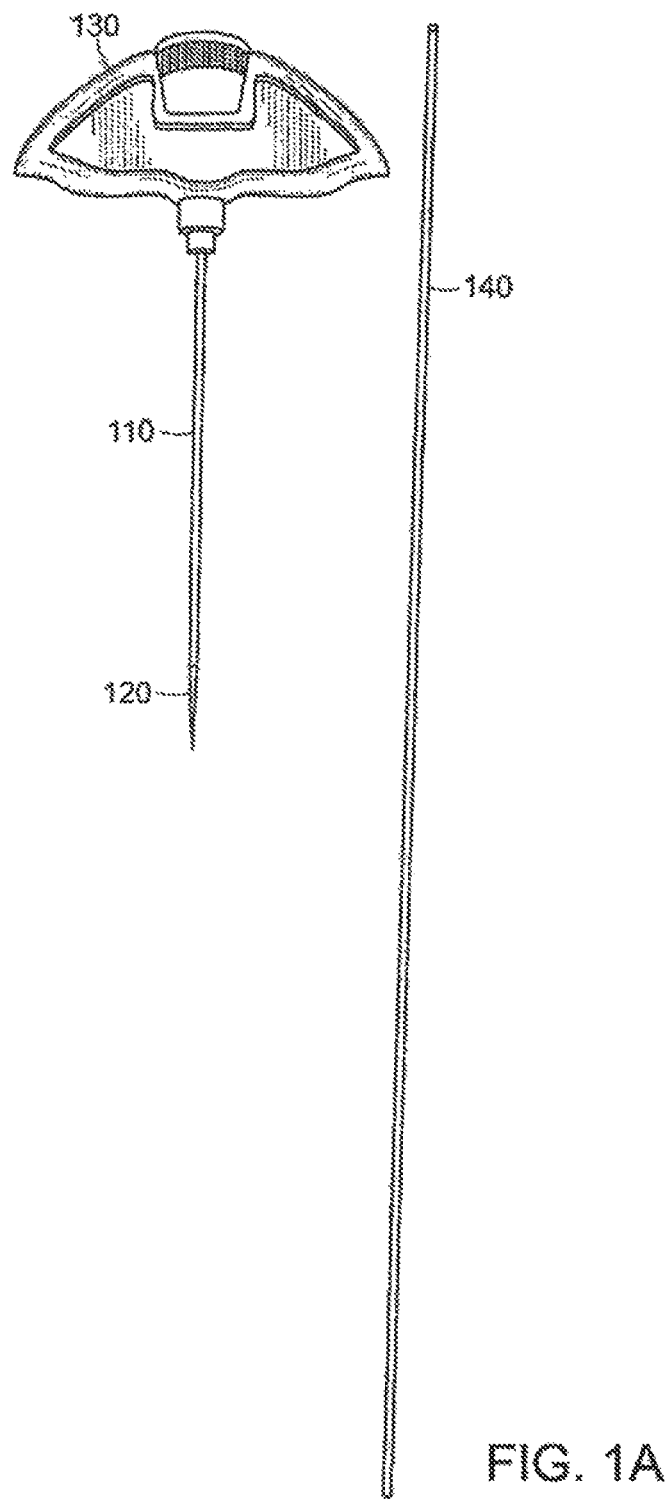
FIG. 1A is a schematic plan view of a Jamshidi needle and K-wire, used in accordance with one embodiment of the invention.

In an example embodiment of the invention, a Jamshidi needle and K-wire arrangement can be used to provide a guide for placement of subsequent devices into the vertebral body. A Jamshidi Needle is a long, tapered combination needle and drill that can be used for insertion into bone. An example Jamshidi needle and K-wire can be seen in FIG. 1A. Here, the Jamshidi needle 110 can include a tapered distal end 120 and a handle 130 at its proximal end. The elongate Jamshidi needle 110 can be hollow, to allow insertion of the K-wire 140 through the needle 140.

Figure 1B:
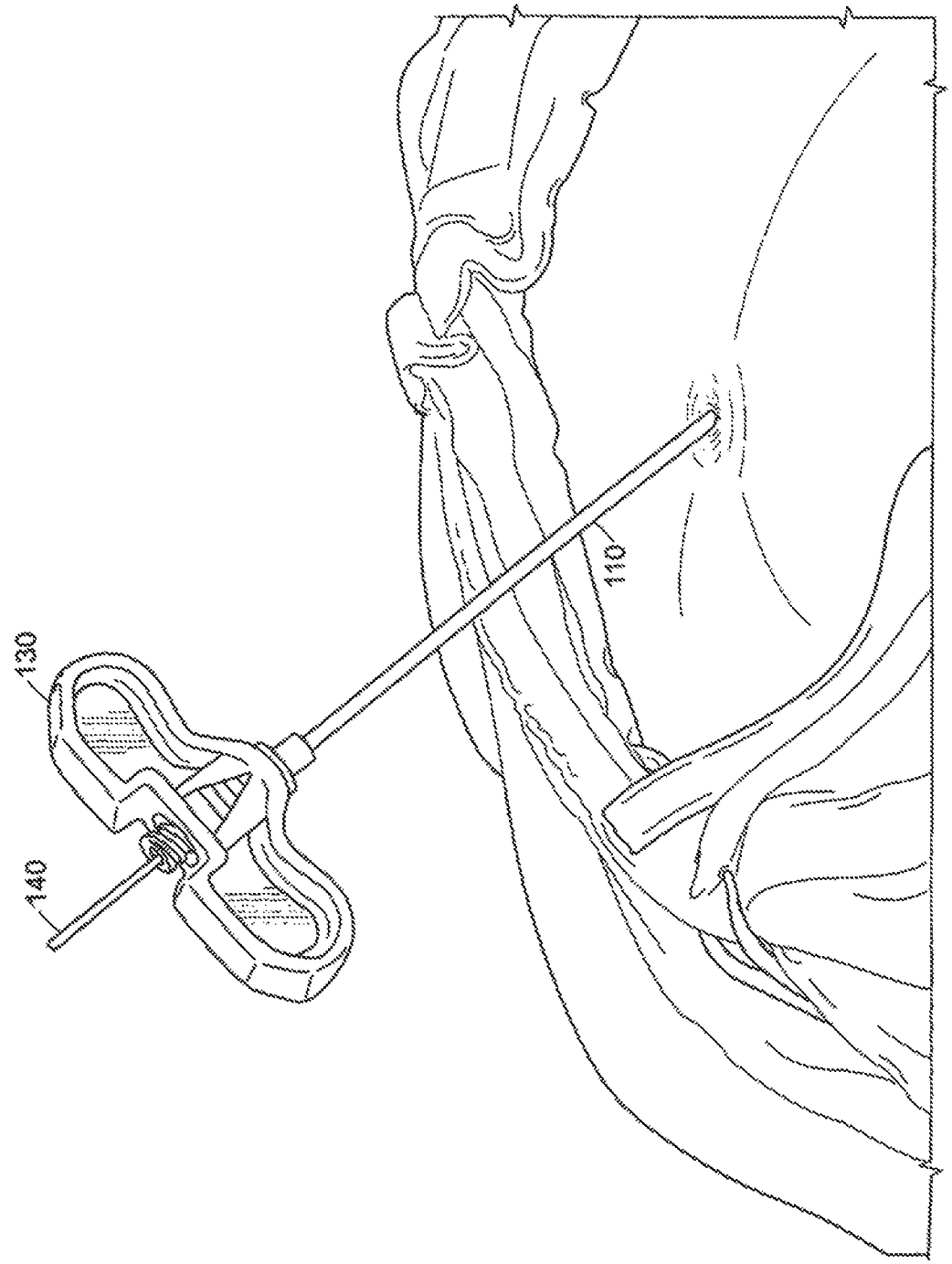
FIG. 1B is a picture of a Jamshidi needle being inserted into a patient, in accordance with one embodiment of the invention.

In operation, the tapered distal end 120 is inserted through the skin and underlying tissue and pressed against the outer wall of the vertebral body. The K-wire 140 can then be inserted through the hollow elongate needle 110 such that the distal end of the K-wire is forced against the wall of the vertebral body. The Jamshidi needle 110 and K-wire 140 can be forced into the wall of the vertebral body to any depth appropriate for the procedure. The Jamshidi needle 110 can then be removed, leaving the K-wire 140 in place to act as a guide needle for the placement of subsequent devices. An example of a Jamshidi needle 110 and K-wire 140 inserted through the skin and underlying tissue of a patient can be seen in FIG. 1B. In alternative embodiments, any appropriate needle type or other device may be used to provide initial access to the vertebral body.

Cannula & Trocar

In one embodiment of the invention, access to the vertebral body can be achieved through the use of a trocar and cannula assembly. This trocar and cannula assembly can be inserted over an already inserted guide wire or needle, such as the K-wire described above, or be inserted directly without the need for a guide wire.

Figure 2C:
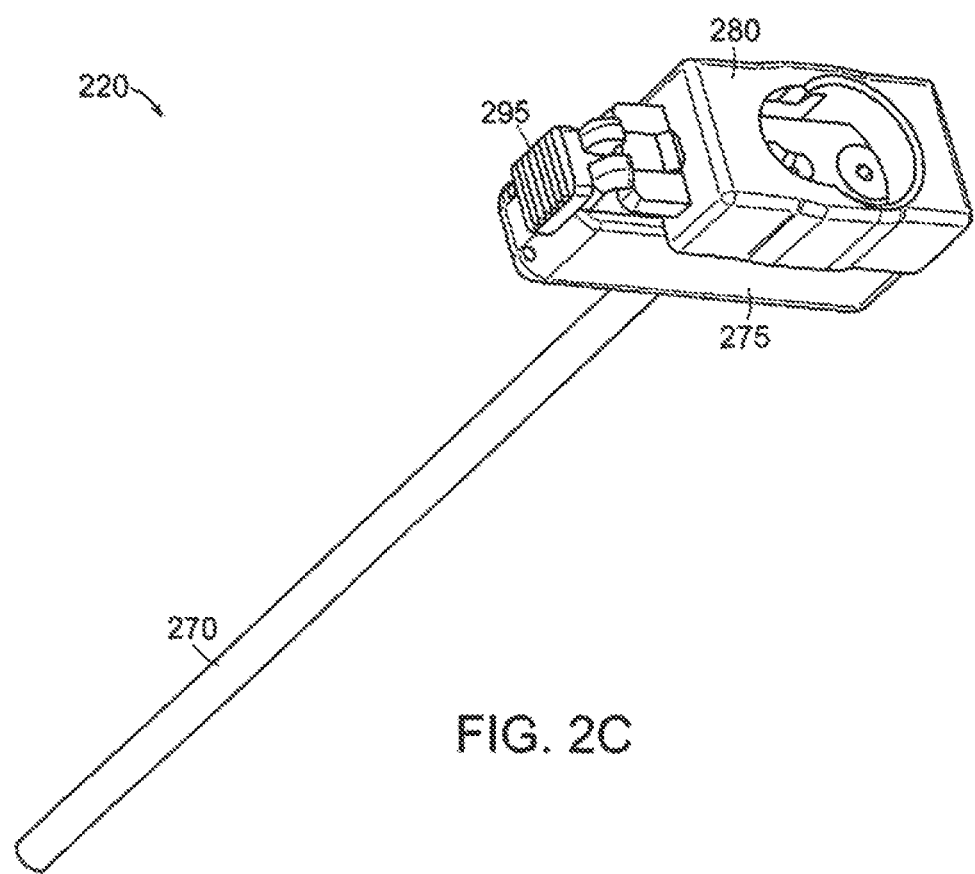
FIG. 2C is another schematic perspective view of the cannula of FIG. 2B.

One embodiment of a trocar and cannula assembly is shown in FIGS. 2A-2F. In this embodiment, the trocar and cannula assembly 200 can include a trocar 210 and a cannula 220. An example trocar 210 is shown in FIG. 2A. In this embodiment, the trocar 210 includes a hollow shaft 230 with a sharpened tip 240, and an impact handle 250 or knob coupled to the hollow shaft 230. The impact handle 250 also has a cylindrical locking flange 260, for releasable interlocking with the cannula 220. The trocar 210 can be configured to fit over a guide wire or needle.

An example cannula 220 is shown in FIGS. 2B and 2C. The hollow cannula 220 can include a thin walled straight tube 270 and a handle 275 with a locking feature 280 attached to the hollow tube 270. The locking feature can include a button, slide, latch, or other appropriate mechanism for releasable engagement with a flange. In the embodiment of FIGS. 2B and 2C, the locking feature 280 includes a locking slide 280 and a locking slide latch 295, wherein the locking slide latch 295 is configured to engage with the locking slide 280 and releasably hold the locking slide 280 in either a closed or open position. The thin walled tube 270 can also have a slot 285 along its axis on the proximal side that is continuous with a slot 290 in the handle 275. The tube slot 285 and the handle slot 290 can be used for instrument orientation or drills, reamers, etc. disposed in the cannula 220.

The handle 275 may be coupled to the thin walled straight tube 270 of the cannula 220 by any appropriate means, including, but not limited to, bonding, pressure fitting, threading, or any combination thereof. The handle 275 may be a plastic, metal, or any other suitable material. The handle 275 can include a locking feature for releasable retention of an instrument placed within the cannula 220. In one embodiment, the handle 275 can include a number of holes through its length, fitted with stainless steel rods, that may be used by the surgeon, under fluoroscopy, for circumferential orientation of the handle 275 and the cannula 220 to ensure the desired relationship between the cannula 220 and the vertebral body.

In one embodiment, the trocar 210 fits within the thin walled straight tube 270 of the cannula 220, and releasably locks to the locking feature 280 of the cannula 220 via the locking flange 260. When locked together, the sharp tip 240 of the trocar 210 can protrude beyond the end of the thin walled straight tube 270 of the cannula 220. In an alternative embodiment, the cannula may include a flexible hollow tube, or a curved hollow tube, allowing the cannula to be placed over a curved guide wire or other curved object.

In use, the trocar 210 and the cannula 220 may be deployed over a guide needle or wire and pressed into the vertebral body, with the trocar 210 providing the displacement and/or cutting means needed to force the cannula through the skin and underlying tissue of a patient and up against, and possibly through, the wall of a vertebral body. The guide wire may be a K-wire 140 as described above, or be any other appropriate needle, piercer, or guiding wire element. Once the cannula 220 is inserted through the outer wall of the vertebral body, the trocar 210 and guide needle can be removed, leaving the hollow cannula 220 in place as an access passageway for subsequent instruments and tools.

An example of a trocar 210 and guide wire 140 inserted through a cannula 220 can be seen in FIG. 2D. In FIG. 2D, the impact handle 250 of the trocar 210 is releasably coupled to the handle 275 of the cannula 220 by the locking feature 280. In one embodiment, the trocar tip 240 can protrude beyond the end of the thin walled straight tube 270 of the cannula 220 and can be rotated relative to the cannula tube 270, if desired. The entire trocar 210 and cannula 220 assembly is placed over the guidewire 140, that was previously inserted into the vertebral body. In one embodiment, a small mallet can be used to tap the trocar 210 to enlarge the hole until the cannula 220 is pressed into the vertebral body to a desired depth. The trocar 210 can then be unlatched from the handle 275 and withdrawn. At this point, the needle or guidewire 295 can also be removed, leaving the cannula 220 in place and held immovably by the wall of the vertebral body.

Figure 2E:
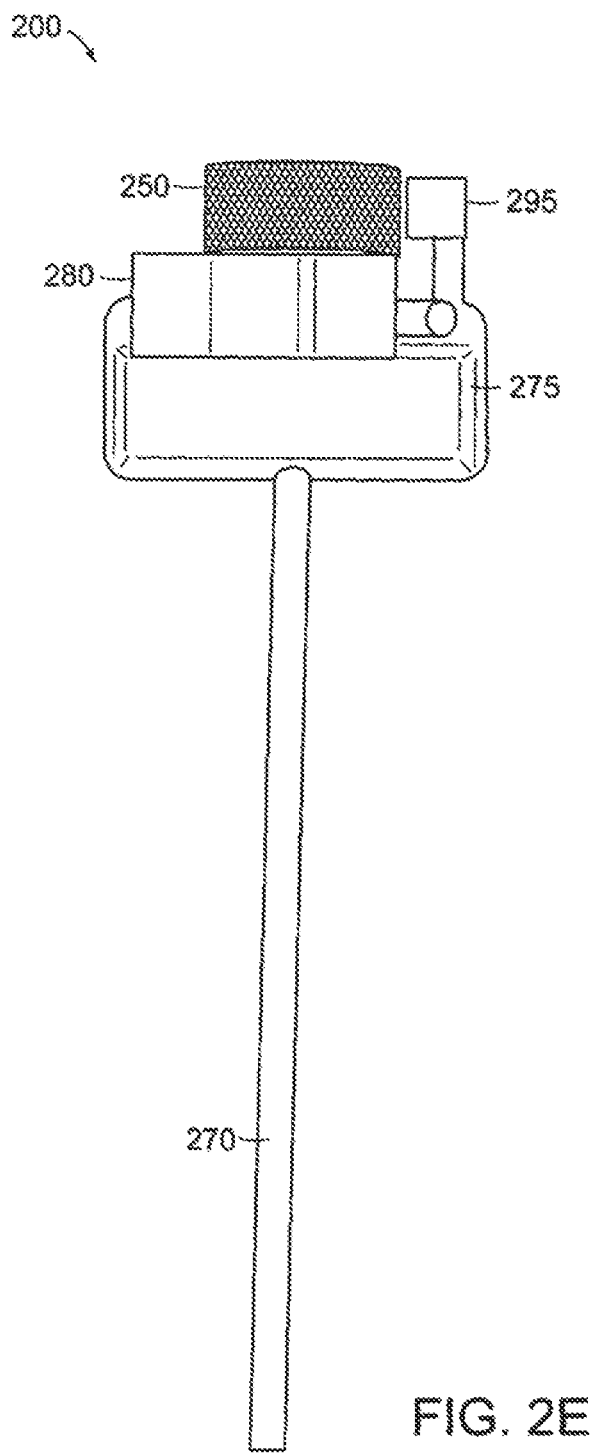
FIG. 2E is a schematic plan view of a cannula, in accordance with one embodiment of the invention.
Figure 2F:
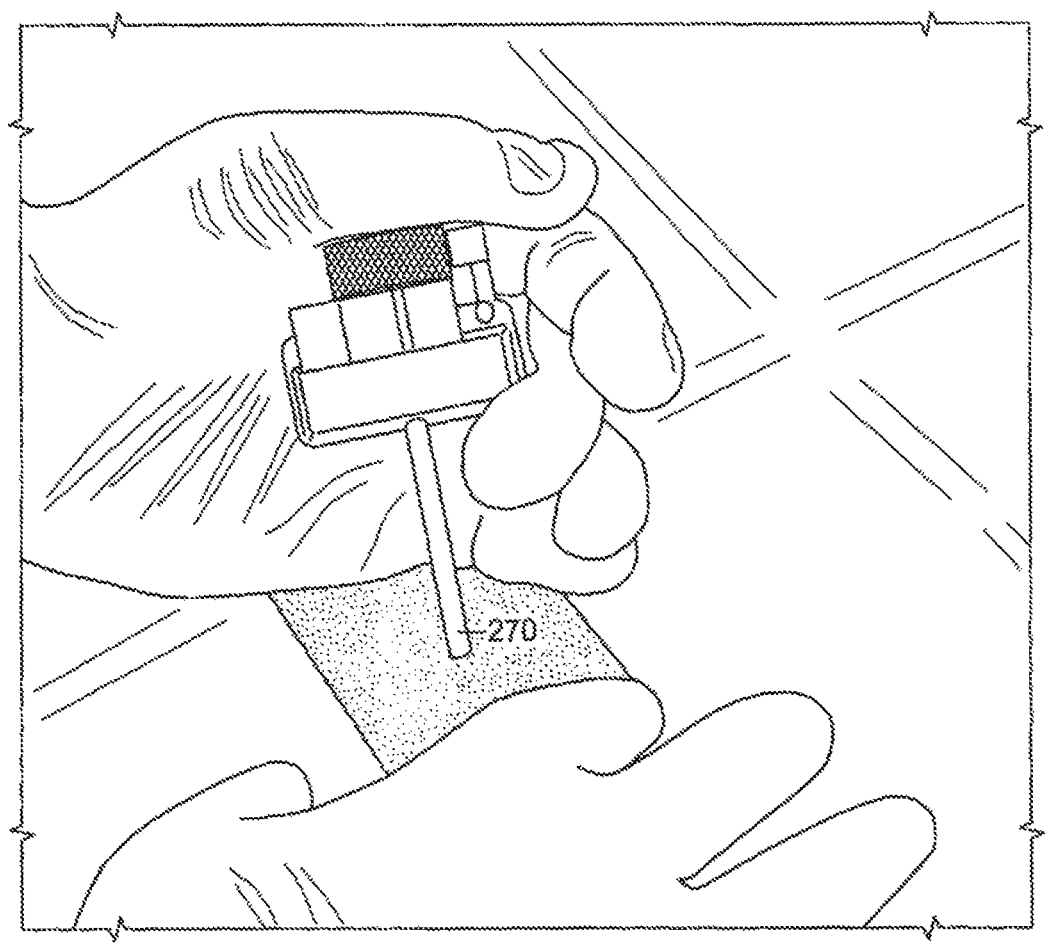
FIG. 2F is a picture of a trocar and cannula being inserted into a patient, in accordance with one embodiment of the invention.

An example embodiment of a cannula 220 and handle 275 can be seen in FIG. 2E. An example of this cannula 220 inserted into a patient can be seen in FIG. 2F.

Curved Drilling Device

In one embodiment of the invention, once the cannula is in place, the next step is to drill a curved hole in the vertebral body. The drilling function is achieved by the use of a curved drilling device. Example curved drilling devices are shown in FIGS. 3A-3I. In one embodiment, the curved drilling device may include a balloon element, as shown and discussed below for FIGS. 7A-7F.

Figure 3A:
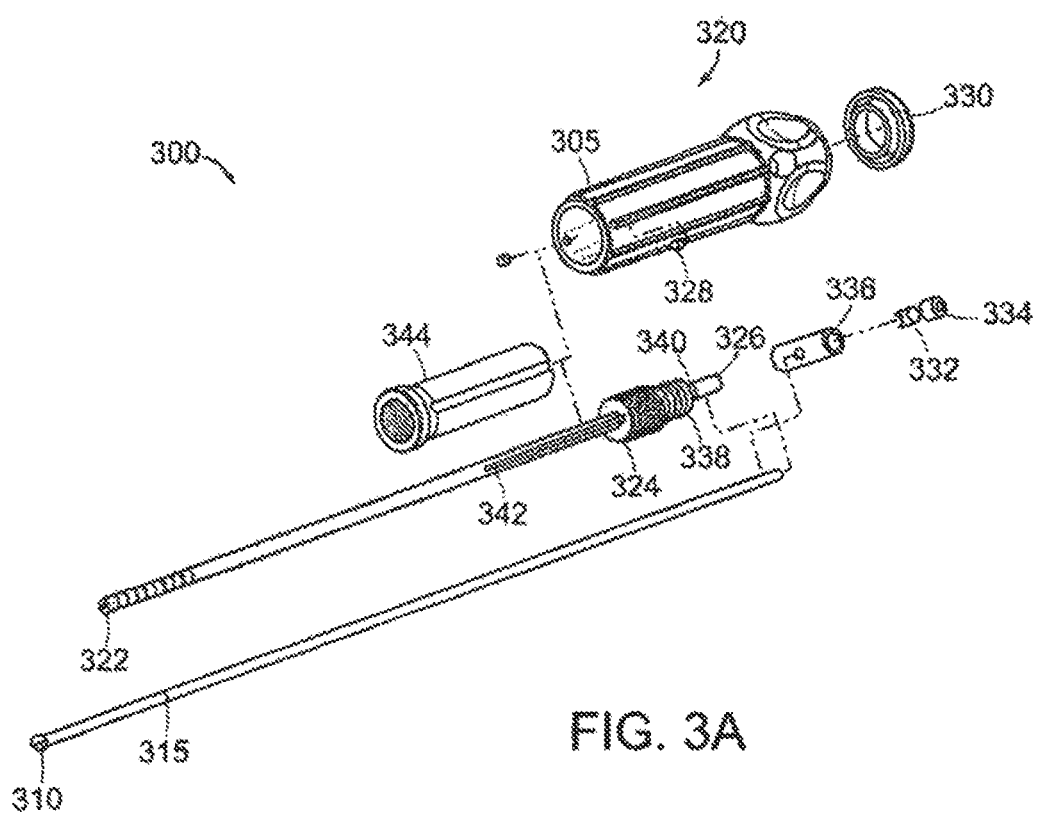
FIG. 3A is an exploded schematic perspective view of a drill assembly, in accordance with one embodiment of the invention.
Figures 3B, 3C, 3D:
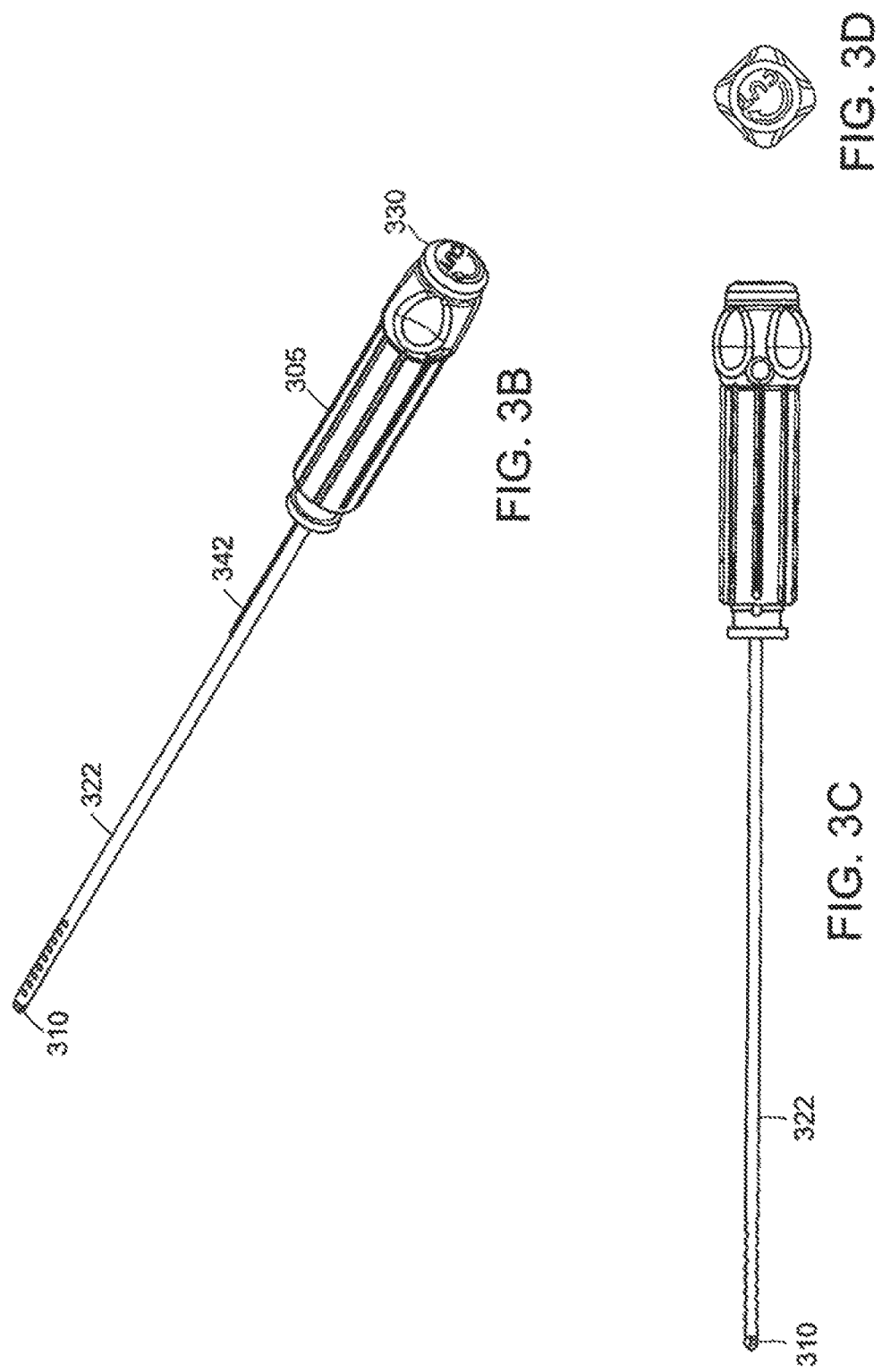
FIG. 3B is a schematic perspective view of the drill assembly of FIG. 3A.
FIG. 3C is a schematic side view of the drill assembly of FIG. 3A.
FIG. 3D is a schematic end view of the drill assembly of FIG. 3A.

In one embodiment of the invention, as shown in FIGS. 3A and 3B, the curved drill device 300 can include a drive handle 305, a sharp tip 310 attached to a flexible torque transmitting drive shaft 315, and a handle drive assembly 320. The flexible drive shaft 315 can be secured and contained by a spring loaded, flexible, slotted metal tube 322 having a feedscrew assembly 324 attached therewith. The proximal end of the drive shaft 315 can include a solid tube 326 bonded, or otherwise coupled, to the flexible shaft 315 component and having sufficient torque transmission capability to drive the shaft assembly. The rotating shaft/sharp tip 310 assembly can further be coupled to the handle assembly 320 by a cross pin 328, or other appropriate device, which can engage with a nut 344 located within the handle 305 and threaded onto the feedscrew assembly 324.

The handle drive assembly can include a number of components to actuate the curving drill, including, but not limited to, a cap 330 for the handle, a clamp 332 for the torque tube, a locking element 334 for the torque tube, and a retainer element 336 for the torque tube. The retainer element 338 can be coupled to a spring element 340 to provide a spring force to a band or other element configured to provide a force to the distal portion of the flexible drive shaft 315 and slotted metal tube 322 to produce the correct curvature at the distal end of the drill 300.

One embodiment of the invention can include an inner tube sized to slide within the outer slotted tube. This inner tube can have an extensive laser cut opening along its distal portion. When assembled, the reduced cross section of this section of the inner tube lies adjacent to the slotted portion of the outer tube along the inside or concave side of the slotted tube. A compression spring of optimized stiffness can be coupled to the inner tube and the outer slotted tube at the proximal end by a lock washer, or other appropriate mechanism, that can be secured to a slot in the proximal end of the inner tube. When the washer is engaged, a tensile force is induced on the inner tube which causes the outer tube assembly to bend at the distal end. Upon bending, the slots on the medial side, which have been designed with gradually decreasing depth to encourage sequential distal to proximal deflection, can close. Therefore, when fully assembled under load of the spring, the outer slotted metal tube can assume a curved orientation with a desired radius of curvature. Since the slotted metal tube is itself flexible being made from hard temper stainless steel, or other appropriate material, it can be straightened against the force of the spring to pass through a straight cannula.

In one embodiment, the drive handle of the drill 300 can be a two part assembly featuring a grip feature suitable to allow manual rotation, coupled to a rotator component having locking flange. The locking flange can be designed to mate with the locking feature of a cannula handle to prevent axial movement but allow rotation. The rotator component can have a female thread throughout its length which can mate with a feedscrew slotted tube assembly. The feedscrew and a key are welded, or otherwise coupled, to the proximal end of the slotted tube.

When assembled to the hollow cannula, the key component 342 can slideably mate with the hollow cannula axial slot, which can rotationally lock the drill's curved slotted tube 322 in a preferred circumferential orientation. Therefore, when the handle assembly is rotated, the slotted tube advances in a fixed rotational orientation relative to the handle assembly at a pace equal to the thread pitch of the feedscrew. The rotating flexible drive shaft assembly, which is axially constrained within the slotted metal tube 322, also advances with the pitch of the feedscrew. The sharp rotating tip 310, by the combined forces of the feedscrew advance and internal spring force curving the shaft, cuts and advances on a curved helical path when the handle is rotated. Conversely, when the handle is counter rotated, the sharp tip retracts along the same curved helical path. If the lock engaging the curved drill is disassembled from the cannula, the device may be slideably removed from the cannula.

In operation, the distal end of the curved tube 322 of the drill can be slotted, perforated, composed of a different and or thinner material, or otherwise adapted to promote bending of the distal end. Any appropriate material, such as stainless steel, aluminum, or other metal, or a plastic or composite material may be used for the drilling device, as long as the material can provide sufficient strength, flexibility, resiliency, and resistance to fatigue. In one embodiment, different components of the drilling device can be constructed from different materials, including any of the materials described herein.

Figure 3E:
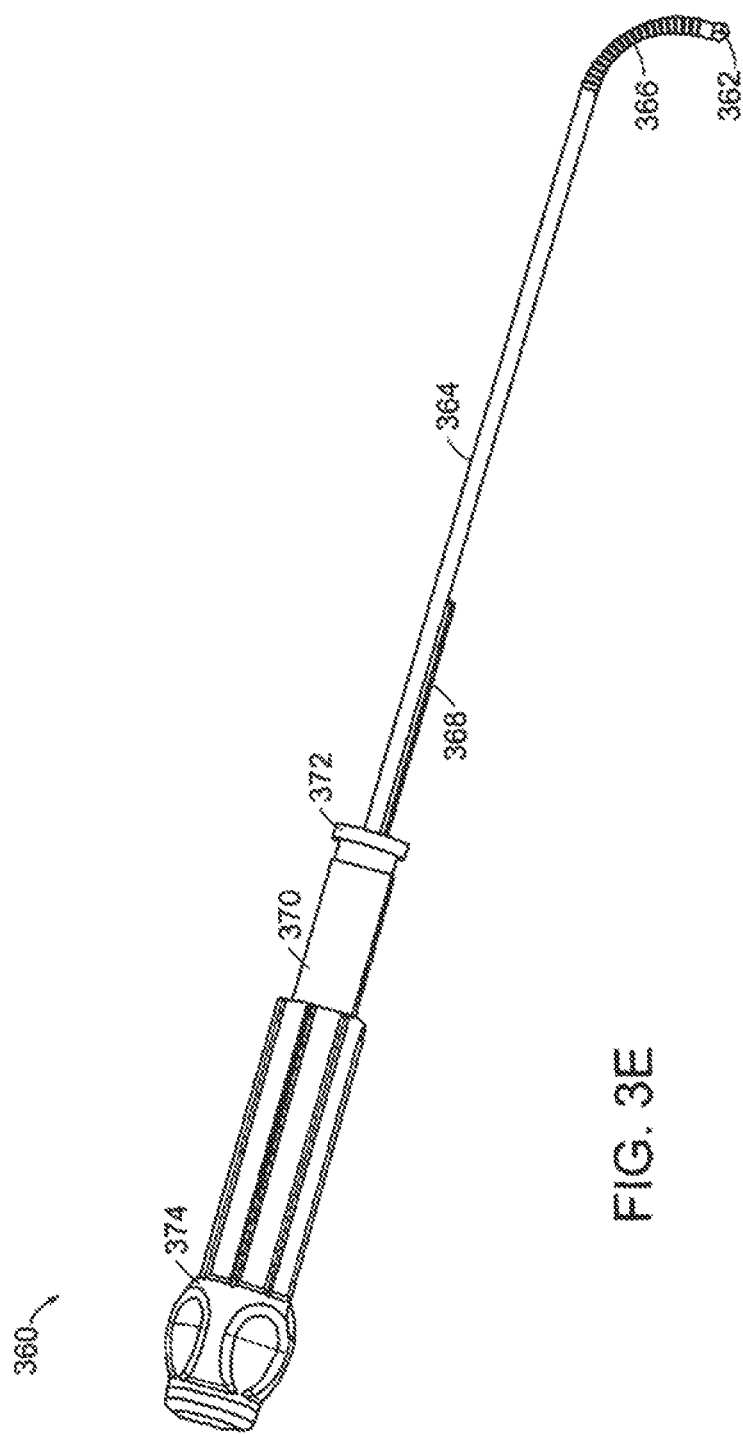
FIG. 3E is a schematic perspective view of another drill assembly, in accordance with one embodiment of the invention.

Another example of a curved drilling device is shown in FIGS. 3E-3I. As shown in FIG. 3E, the curved drilling device 360 can include a drill tip 362, a drill shaft 364 with a slotted portion 366 at the distal end for bending, an orientation key 368, a drill feed unit 370 complete with a locking flange 372 and a handle 374 for rotation.

Figure 3F:
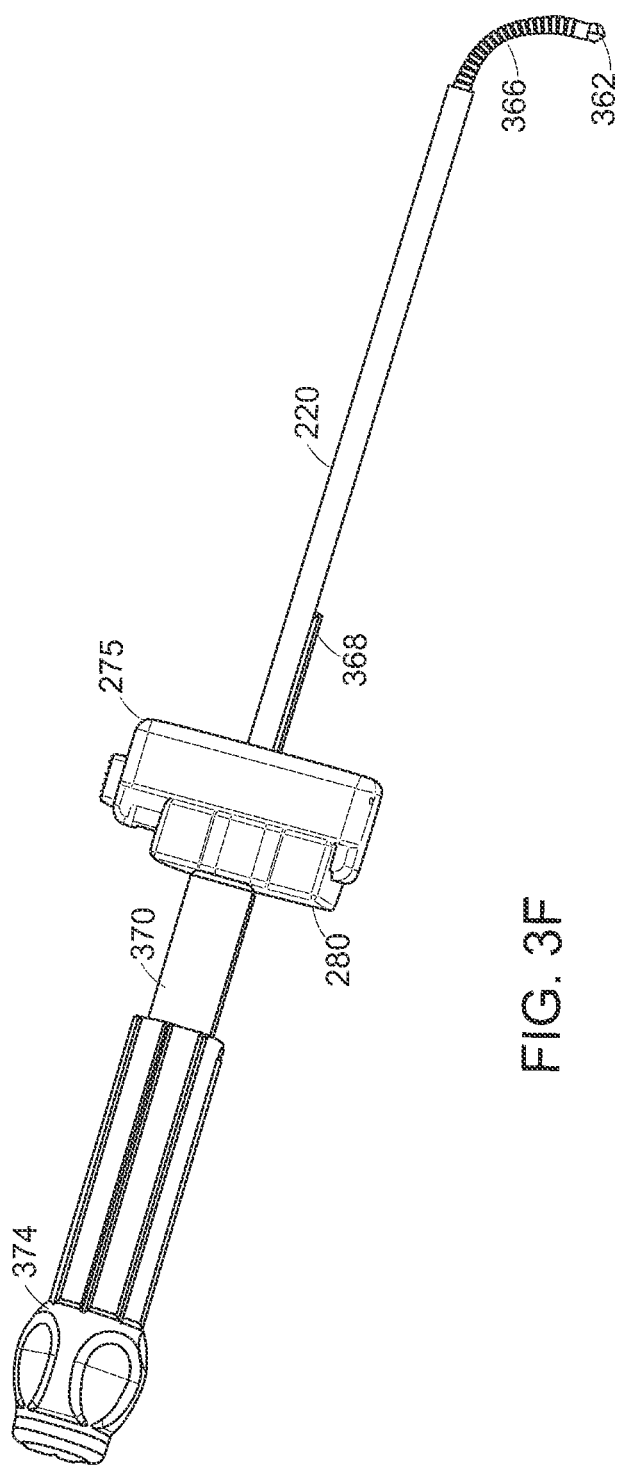
FIG. 3F is a schematic perspective view of the drill assembly of FIG. 3E inserted within a cannula, in accordance with one embodiment of the invention.

The curved drilling device 360 releasably attached to a cannula and handle assembly 220 is shown in FIG. 3F. In one embodiment of the invention, when the curved drilling device 360 is initially installed into the cannula 376, the protrusion is only that of the drill tip beyond the cannula and as such, the slotted portion of the drill shaft is contained in the cannula and is therefore straight and not curved. The distal end of the drilling device 360 is free to curve once it has been deployed beyond the distal end of the cannula.

Figure 3G:
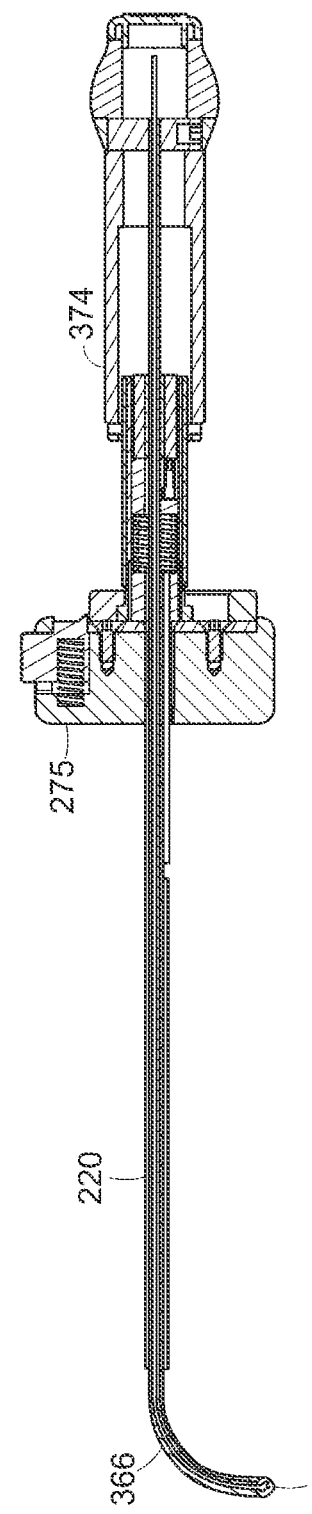
FIG. 3G is a sectional side view of the drill assembly of FIG. 3E inserted within a cannula.
Figure 3J:
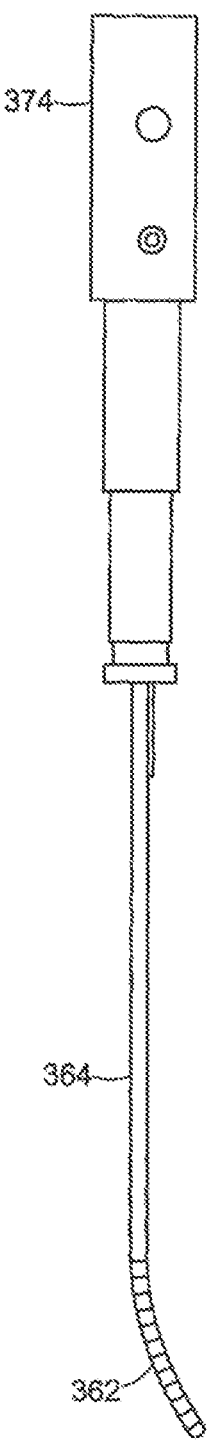
FIG. 3J is a schematic plan view of a drill assembly, in accordance with one embodiment of the invention.
Figure 3K:
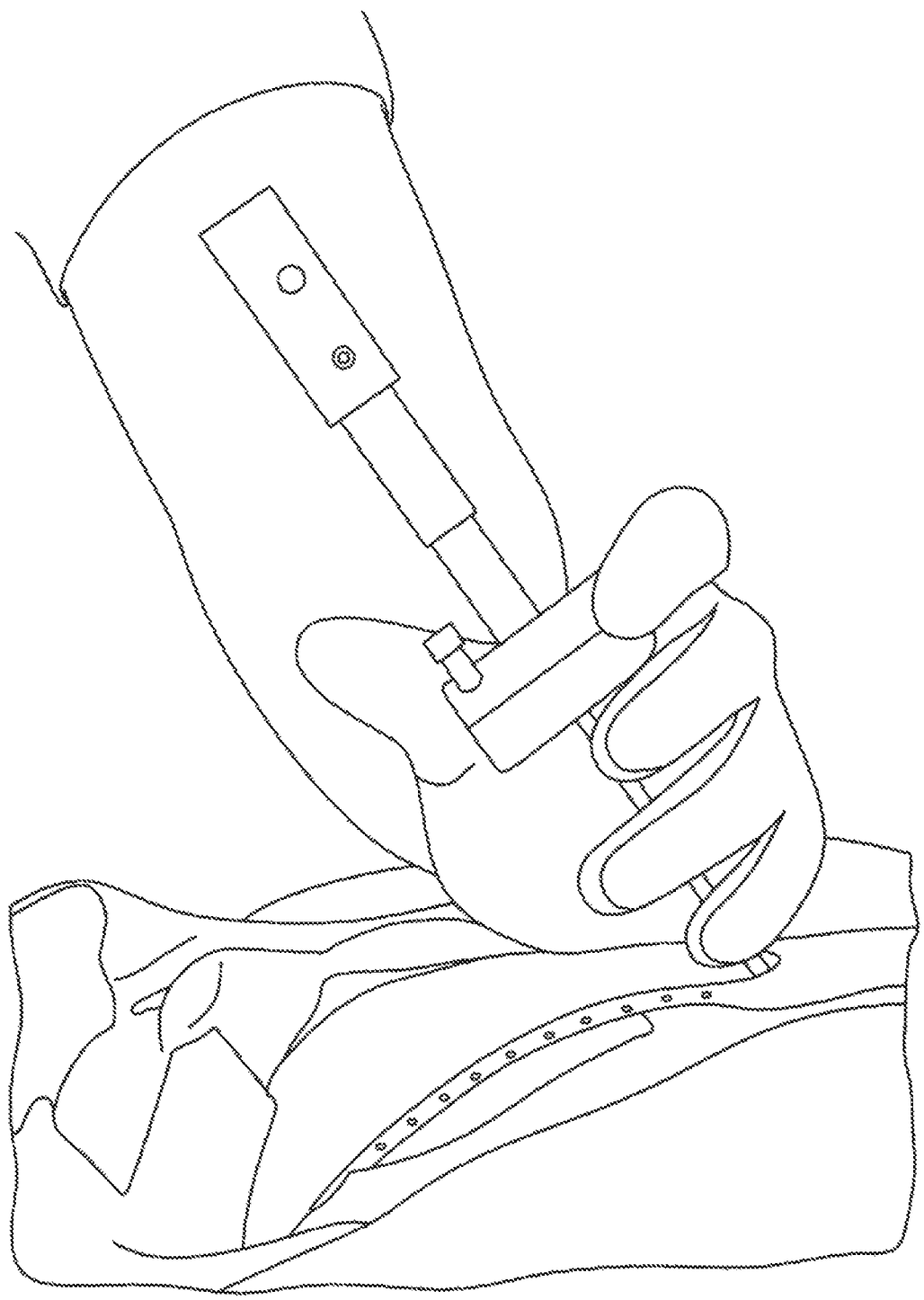
FIG. 3K is a picture of a drill assembly being inserted into a patient, in accordance with one embodiment of the invention.

A cross-section of the curved drilling device 360, depicting the internal mechanisms of the system, is shown in FIG. 3G. More detailed enlarged cross-sectional diagrams are provided in FIGS. 3H and 3I. In FIG. 3H the distal end of the drill unit is illustrated. In this embodiment, the drill tip 362 can be welded, bonded, threaded, or otherwise coupled, to a cabled torque tube 378 that provides rotation of the tip 362. The torque tube 378 may be an array of wires wound in a helical, circular manner that provides torque strength with the flexibility to "go around the corner" to deliver the necessary power to the drill tip 362 to cut bone. A drill safety cable 380 can be coupled to the drill tip 362 to promote drill tip retrieval in the unlikely event that it becomes detached from the cabled torque tube 378.

The slotted portion of the drill tube 366 is bent into a desired arc as it exits the cannula. This is achieved by means of the band 382, located on the inside of the bend and firmly attached to the drill shaft 364 at its distal end and attached to a compression spring assembly 384 at its proximal end. As a result, the band 382 can be held under spring tension, thus pulling on the inside of the drill shaft 364 to produce an arc, as desired.

FIG. 3I is a detailed cross section of the drill unit and handle, in accordance with one embodiment of the invention. In one embodiment, the locking flange on the drill unit can be retained by the locking flange of the handle. That, in turn, can be held in place by the locking slide 280 on the handle. The locking flange component can also have an internal thread or drill feed nut.

In one embodiment of the invention, a feed screw 386 includes a matching male thread. The proximal end of the drill shaft can be affixed to the feed screw 386 by welding, bonding, threading, or other means, and the feed screw 386 and drill shaft can have a key, also attached by welding or other means, to ensure the desired circumferential orientation of the drill shaft within the cannula 220. The key interface can align the handle plane to the plane of the curved drill shaft. One embodiment can also include a compression spring 388 for providing a pulling force on the band in order to bend the distal end of the drill shaft to the desired arc. A band retention device 390 can contain the compression spring 388. The compression can be preloaded to a desired force and the band retained to ensure that there is always tension on the band. In one embodiment of the invention, the spring 388 may be compressed as the band is pulled distally to allow for straightening of the drill shaft when passing through the cannula.

In one embodiment, the torque tube 392 can go through the drill shaft and feed screw, as well as through the band retention device, and be fastened to the handle 374 by the torque retention device 394 that is keyed to the rotation handle 374. The drill safety cable can go through the entire length of the torque tube and the excess can be tied into a knot. Alternatively, a ferrule can be staked to the drill safety cable so that it does not slide out of the torque tube inadvertently.

In operation, according to one embodiment of the invention, as the handle 374 is rotated the pins in the handle interact with the slots in the drill feed unit and cause it to rotate. This action causes the feed screw to move and advance the drill while rotating the drill tip 362 for cutting. This motion allows the drill tip 362 to cut a curvilinear path through the interior of the vertebral body. The progress of the pathway can be monitored by use of a medical imaging technique, or be measured by means of a distance scale associated with the drill and indicating the extension of the drill tip beyond the end of the cannula. An example embodiment of a drill assembly can be seen in FIG. 3H. An example of this drill assembly inserted into a patient can be seen in FIG. 3I.

Reamer

In one embodiment of the invention, the curved path can be created by a reamer device in the same manner as the drill device. Alternatively, the path created by the drill device can be enlarged by a reamer device used after the drill device has created the initial path. An example of a reamer device is shown in FIGS. 4A-4G.

In one embodiment, the distal end of the reamer is configured for insertion through a cannula into a vertebral body. The reamer can include an orientation key configured to mate with a corresponding slot in the cannula to ensure that the distal end of the reamer is deployed at the correct circumferential angular orientation. The reamer may be releasably lockable in the cannula.

In one embodiment, the reamer can include a circumferentially partially slotted outer tube, wherein the slots enable the distal end of the reamer to bend in a predetermined direction. The reamer may include a band inserted within the outer slotted tube and coupled to the distal and the proximal ends of the reamer to bend the slotted outer tube in a predetermined direction and at a set angle. The proximal end of the band may be coupled to a compression spring to provide a predetermined amount of flex to the distal end of the reamer, thus allowing the distal end to be straightened while being inserted through the cannula, and then return to its predetermined bent configuration upon being extended beyond the end of the cannula.

The reamer may include a reamer blade yoke configured to extend from the distal end of the outer slotted tube. A reamer blade may be pivotably coupled to the reamer blade yoke by a pivot pin. The reamer may include a cabled torque tube coupled to the reamer blade yoke to rotate the reamer blade yoke and coupled reamer blade while the outer slotted tube remains stationary. A cable may be extended through the cabled torque tube and coupled to the reamer blade to provide a force to pivot the blade about the pivot point from a neutral, centered configuration to a tilted/opened configuration. The cable may be attached, at the proximal end of the reamer, to a compression spring. The compression spring attached to the cable can eliminate slack in the cable and allow the angle of the reamer blade to elastically deflect from its set angle.

In one embodiment, the proximal end of the reamer may include a handle. The handle may include a blade opening sleeve. Rotation of the blade opening sleeve can open or close the reamer blade with or without rotating the blade. The handle may also include a rotation handle. Rotation of the rotation handle can rotate the reamer blade about the reamer blade yoke. Rotation of the rotation handle can also provide a proximal movement of the distal end of the reamer back towards the distal end of the cannula;

In operation, in one embodiment of the invention, rotation of the reamer blade, while opening the blade, results in a semi-spherical cavity being created. Once the blade is fully opened, rotation of the rotation handle provides a rotational movement and a proximal movement of the reamer blade, allowing the reamer blade to follow a generally helical path to create a curved, generally cylindrical cavity of a length determined by the amount of rotation of the rotation handle. The proximal end of the reamer may include markings to indicate the amount of proximal movement of the distal end of the reamer from an original, fully extended position. Rotation of the blade opening sleeve in the opposite direction can return the reamer blade to a neutral/centered orientation. Upon returning the reamer blade to the neutral/centered orientation, the reamer may be unlocked and removed from the cannula.

In one embodiment, the reamer device may be similar in construction to the drill devices described above. Both devices can have a slotted tube assembly and a flexible torque transmitting drive shaft contained therein. Both devices can have an internal tube welded, bonded, or otherwise coupled at the distal end, and joined by a washer and compression spring at the proximal end. However, the reamer device can have a moveable blade disposed at its tip. The moveable blade can be attached to a yoke by a pivot pin, and to a cable tether that is crimped, bonded, welded, or otherwise attached to the moveable blade at a location distal to the pivot pin.

More specifically, a reamer device 400 for enlarging the drilled cavity to a desired diameter and curvilinear length is shown in FIG. 4A. The reamer device 400 may have similarities to the drilling device described above in that it has a shaft 405 that is slotted at the distal end 410 for curving, and the curving is produced by a band that is spring loaded by a compression spring situated between the feed screw and the band retention device. In this embodiment, the reamer device 400 includes a reamer blade 415 that is pivotably coupled to a yoke 420 that is mounted on the distal end of the shaft 405. An orientation key 425 may be mounted to the shaft 405 to engage with a slot in a cannula and ensure the correct circumferential orientation of the reamer device upon insertion. At its proximal end, the reamer device 400 can include a dual function handle 428 including rotation handle 430 for rotating the blade 415, a blade opening sleeve 435 for deploying the blade, and a reamer feed nut 440 for moving the blade back and forward along the axis of the shaft as the blade is rotated. The proximal end of the handle 430 may be a tubular molded component with gripping features on its external surface. In an alternative embodiment, the handle 430 may be manufactured from any appropriate metal, plastic, ceramic, composite material, or combination thereof. Rubber or fabric elements may also be placed on the outer surface of the handle 430 to promote grip.

Figure 4E:
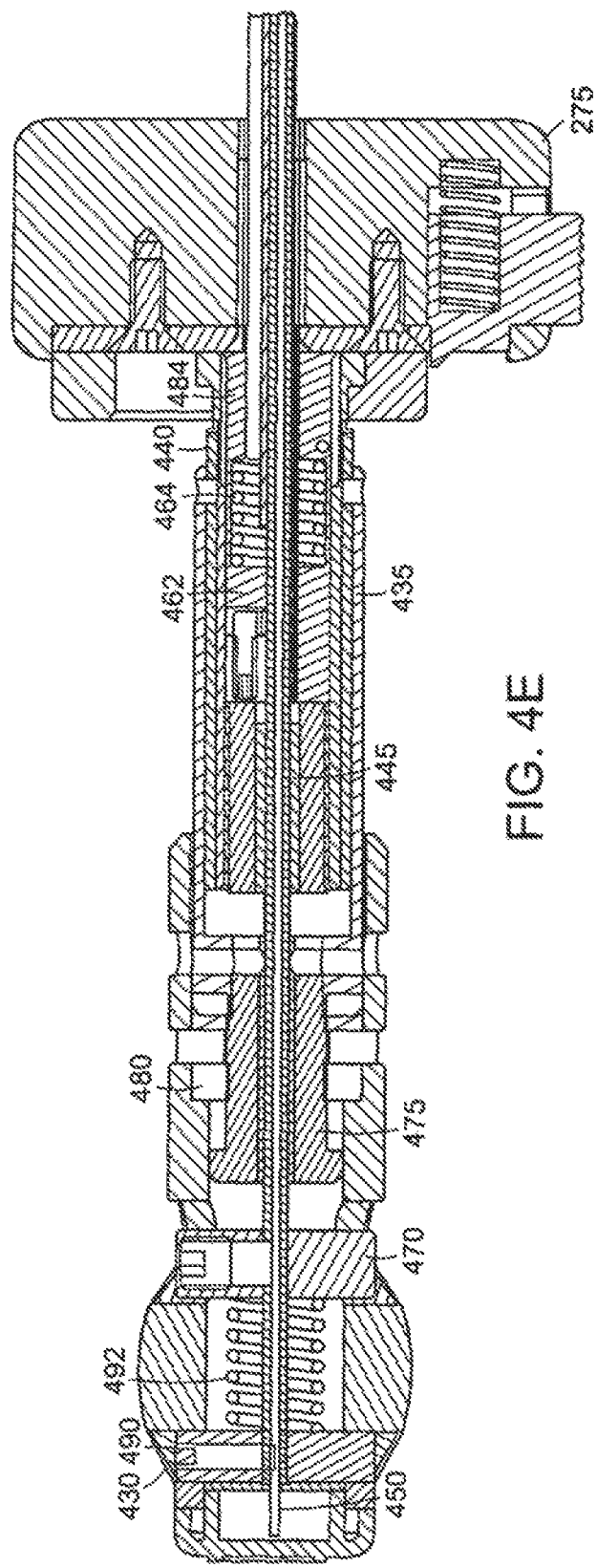
FIG. 4E is an enlarged sectional side view of the proximal end of the reamer assembly of FIG. 4A inserted within a cannula.
Figure 4F:
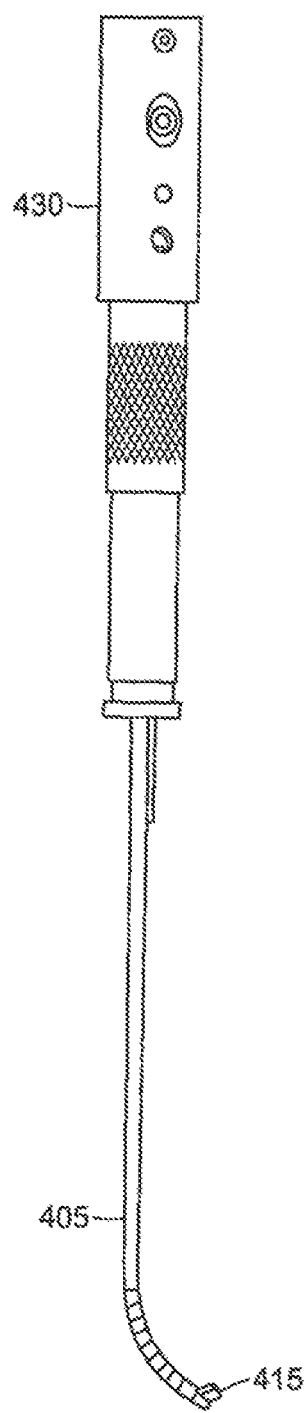
FIG. 4F is a schematic plan view of a reamer assembly, in accordance with one embodiment of the invention.
Figure 4G:
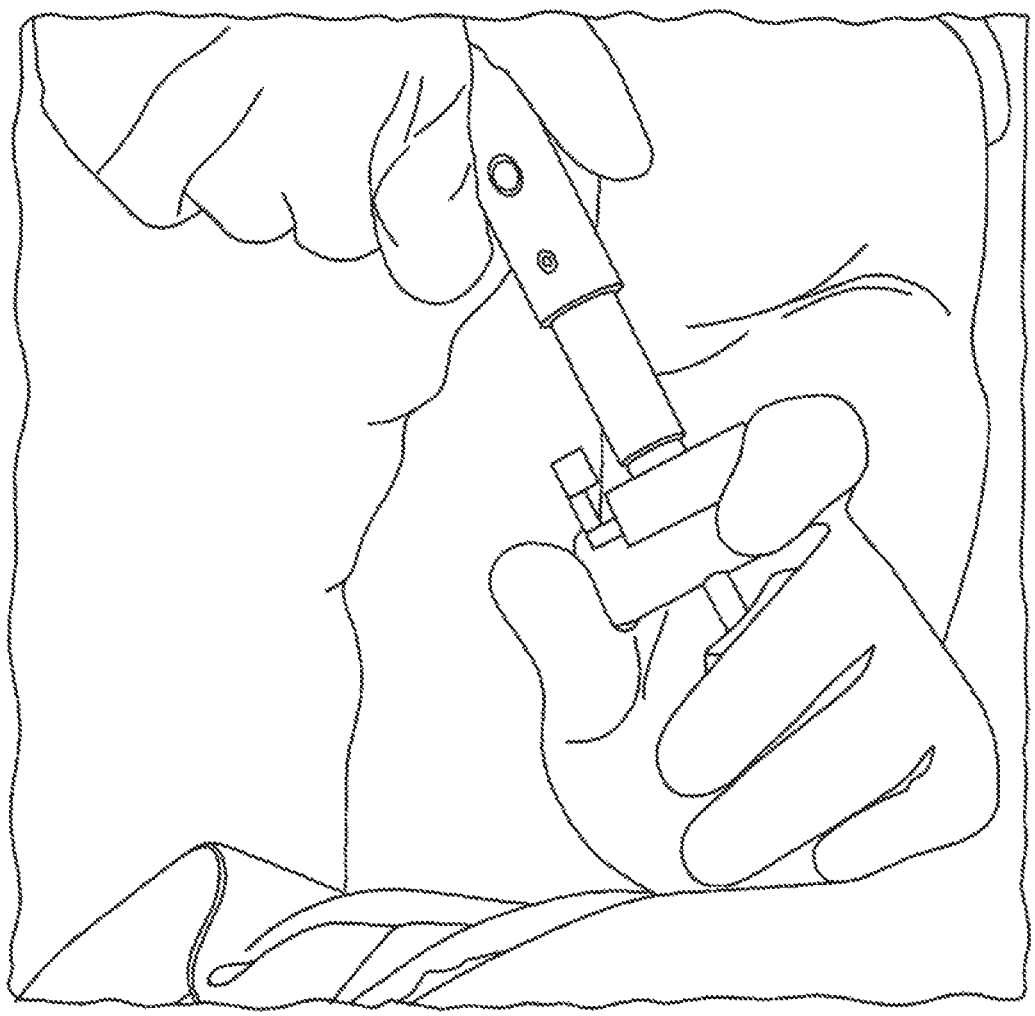
FIG. 4G is a picture of a reamer assembly being inserted into a patient, in accordance with one embodiment of the invention.

The reamer device 400 releasably attached to a cannula and handle assembly 220 is shown in FIG. 4B. A cross section of the reamer device 400, depicting the internal mechanisms of the system, is shown in FIG. 4C. More detailed cross-sectional diagrams are provided in FIGS. 4D and 4E.

In one embodiment, the reamer assembly may also be retained in the cannula and handle assembly 220 in the same manner as described above for the drilling device. The reamer feed nut 440 may work in the same way as described above for the drilling device feed nut. In one embodiment, a torque tube 445 can provide power for reaming (enlarging) the drilled hole, with the torque tube 445 driving the yoke 420 that houses the pivoting reamer blade 415. An inner cable 450 that goes through the center of the torque tube 445 can be used to tilt or open the blade 415 from the neutral position aligned with the axis of the shaft 405 to a deployed position at an angle to the axis of the shaft 405. The blade 415 can tilt or pivot about a pivot pin 455 coupled to the reamer blade yoke 420. As with the drilling device above, the curvature of the distal end of the reamer device 400 can be set by a band 460 placed within the slotted tube 410 and held in tension by a spring element at the proximal end of the reamer device 400. The fully deployed angle may be set at any appropriate angle. In one embodiment, the deployment angle may be set at any angle up to 90°. For example, the fully deployed angle may be in a range from 20° to 90°, or from 30° to 70°, or from 45° to 60°.

The curvature of the distal end may be set to any appropriate angle by correct selection of the band length. A band retention device 462 can hold the band 460 at the proximal end of the reamer device 400, with a compression spring 464 coupled to the band retention device 462 to allow the shaft 405 to flex from its preferred steady state curvature during deployment through the cannula 220 and upon contact with a "hard" element within the vertebral body.

The reamer device 400 can include a multi-component, dual function handle. A cross-section of an example handle is shown in FIG. 4E. In one embodiment of the invention, a lost feed motion may be needed to open the reamer blade, while rotating the reamer handle, with the feed system remaining still. This feature is provided by means of a blade opening sleeve 435. In one embodiment, this may be achieved by a rotation of the handle to initially "telescope" the handle from the blade opening sleeve 435 to pull on the center cable 450 to open the reamer blade 415 all while no feeding motion occurs. A torque tube retention device 470 travels in an elongated slot in the rotation handle 430 so no proximal movement results. The blade opening sleeve 435 retains a "T" screw 475 that provides the proximal movement of the handle for blade opening and when a blade opening nut 480 stops on the head of the T screw 475, rotation is now transferred to the reamer feed nut 440.

The reamer feed nut 440 rotation pulls the feed screw 484 proximally and at the distal end the reamer blade is rotating and feeding proximally resulting in cutting bone and creating a curved cavity to desired length with fluoroscopy, or other appropriate means, for visual reference. After the desired length of cavity has been achieved, the rotating handle 430 is rotated counter to the cutting direction and the reamer blade 415 will fold back inward to the center starting position. The reamer assembly can be unlatched from the handle and removed. The cannula and handle assembly 220 can remain in place, however, so that further devices, such as devices that permit the insertion of the stent and the medical cement, can be inserted into the enlarged cavity.

The cable 450 originating from the moveable blade may be fed through the entire assembled device and terminated and crimped, or otherwise coupled, to a cable retainer 490, such as a cross pin assembly, that is coupled to the wall of the rotation handle 430. A spring 492 may be located within the proximal inner border of the rotation handle 430 adjacent to the cable retainer 490. A thread may be used to couple the rotation handle 430 to the remainder of the reamer device 400.

In one embodiment, the dual function handle 428 may induce a tensile force on the cable tether 450 by rotating the proximal molded component relative to the distal handle component to effectively lengthen the handle. The cable tether thereby pulls the moveable blade 415 to cause a pivoting of the blade from a closed to an open position. The handle 428 can then cause the rotation of the flexible drive shaft assembly to rotate the blade 415 within the cavity.

The handle assembly, including the distal and proximal components, may be further secured to a rotator component having an internal thread mating the feedscrew component 484 of the slotted tube assembly. Thus, its function may be substantially identical to that of the drilling device described above. However, the feedscrew rotation may not be enabled until the reamer blade has been fully deployed via rotation of the proximal component of the handle 428. Therefore, in one embodiment, when the rotation handle 430 is rotated, the moveable blade assembly first rotates and deploys, then translates due to the action of the feedscrew mechanism 484. The deployed blade therefore enlarges the path to a required diameter by simultaneously rotating and translating the blade 415. The direction of translation, in one embodiment, is retrograde, which is achieved by the use of a left hand thread in the feedscrew 484.

In one embodiment, the blade deployment from a neutral to an open position may only occur when the blade is rotating. In an alternative embodiment, the blade deployment may be independent of the blade rotation. The rate of blade deployment from a closed to an open position is dependent on the pitch of the thread which joins the proximal and distal handle component.

In an alternative embodiment, the reamer device may be configured to drill into the vertebral body as it is advanced, before being deployed to extend the size of the cavity, as described above. In this embodiment, the reamer device can function as both a reamer and a drill, thus eliminating the need for a separate drilling device.

Figure 5A:
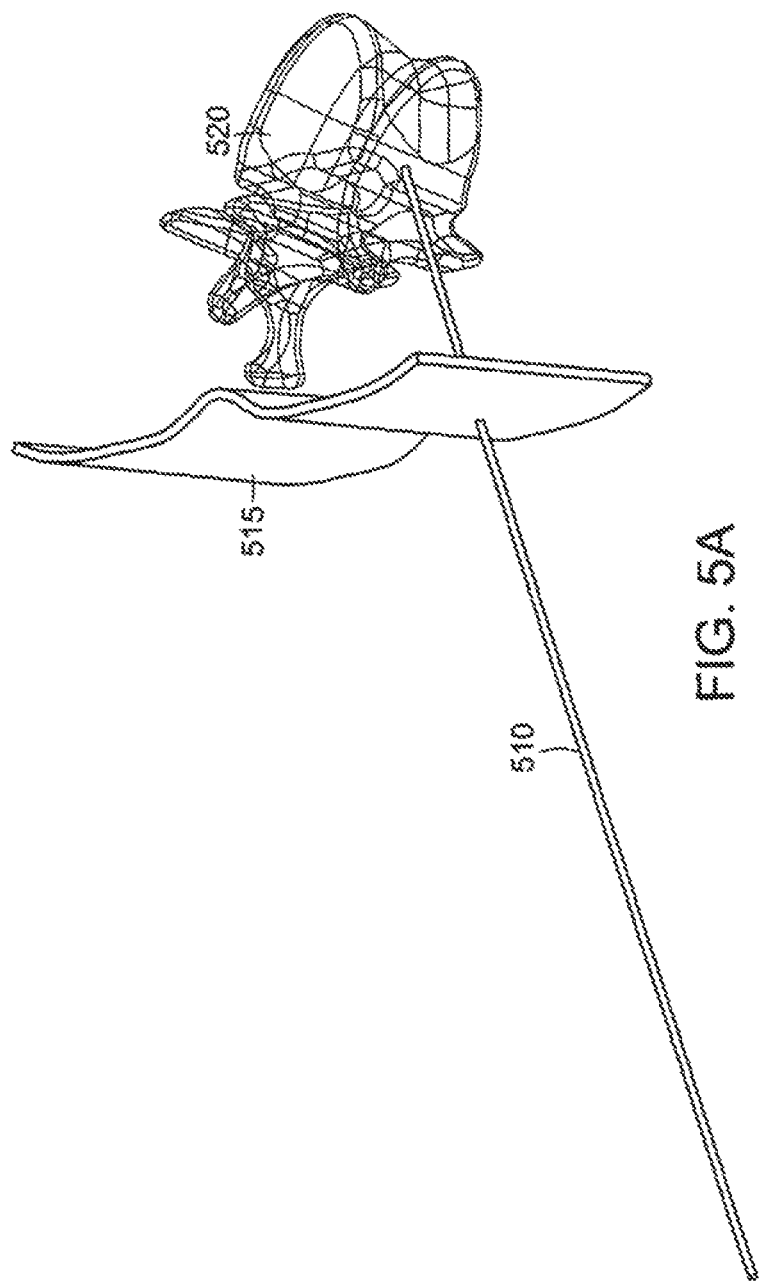
FIG. 5A is a schematic perspective view of a needle being inserted into a vertebral body, in accordance with one embodiment of the invention.
Figure 5C:
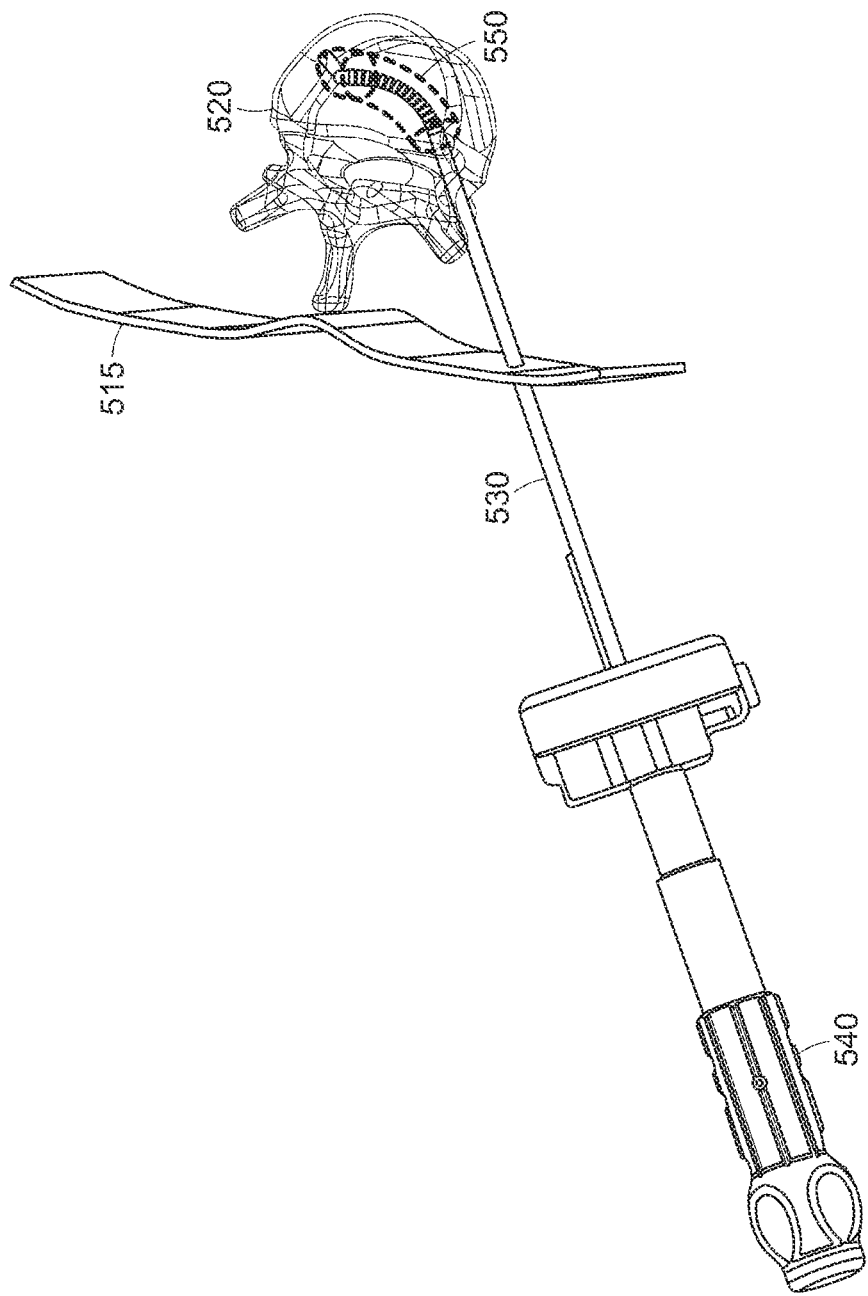
FIG. 5C is a schematic perspective view of a reamer assembly being inserted through a cannula into a vertebral body, in accordance with one embodiment of the invention.
Figure 6A:
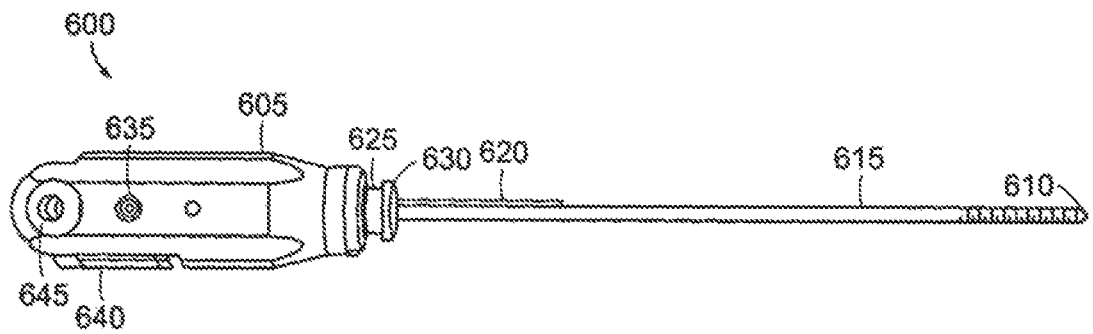
FIG. 6A is a schematic side view of a drill assembly with a lever and drill cam, in accordance with one embodiment of the invention.
Figure 6B:
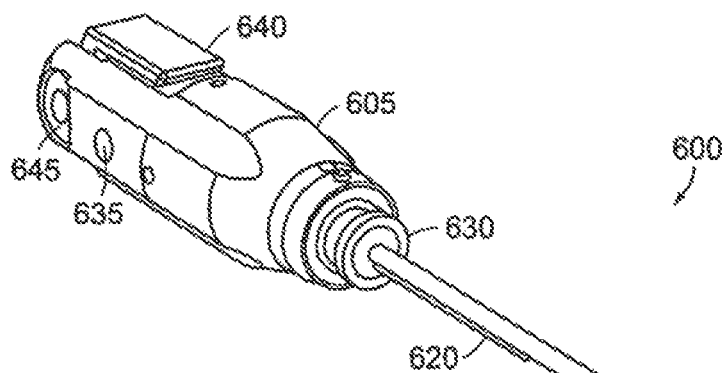
FIG. 6B is a schematic perspective view of the drill assembly of FIG. 6A.
Figure 6C:
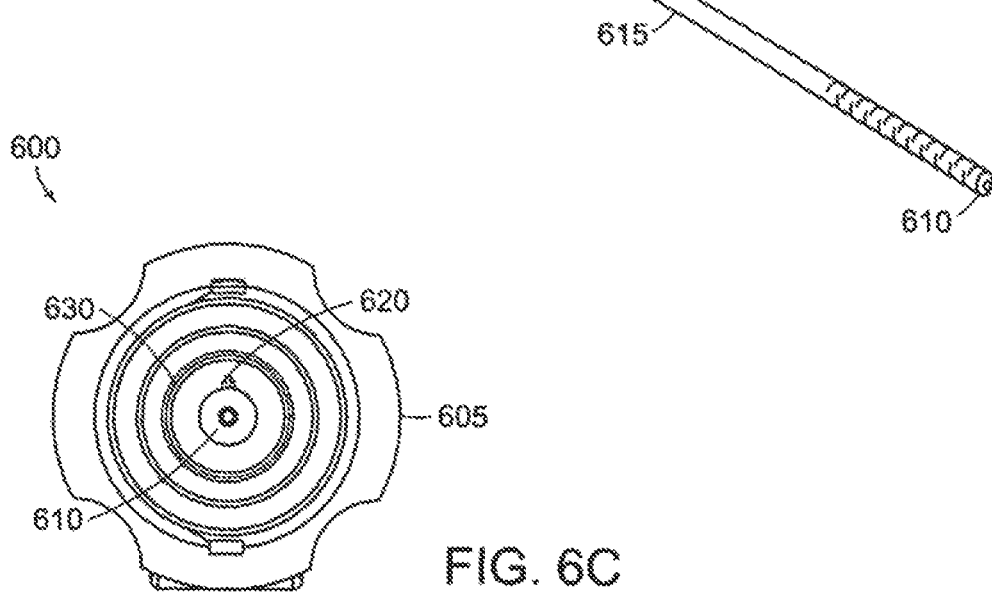
FIG. 6C is a schematic end view of the drill assembly of FIG. 6A.
Figure 6D:
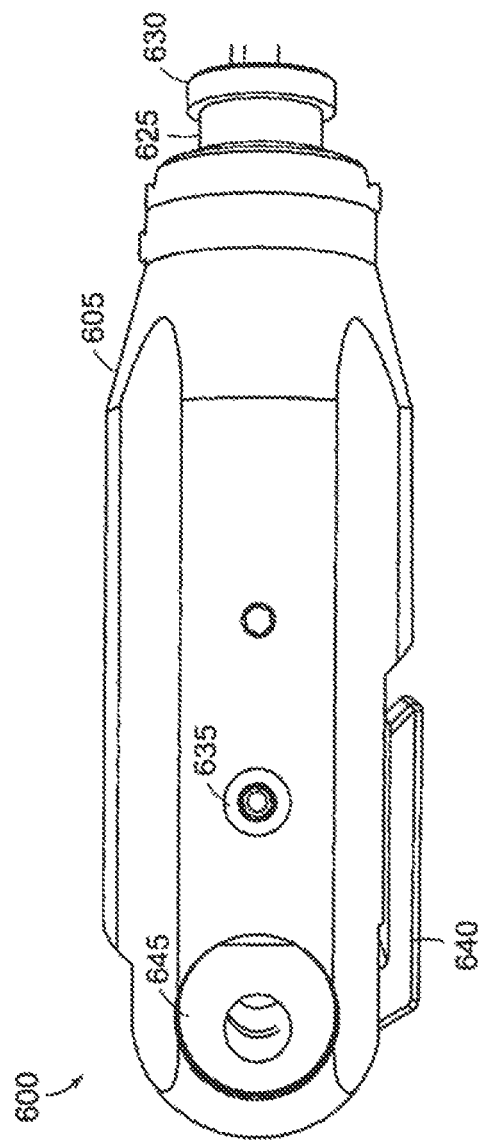
FIG. 6D is a schematic side view of the handle of the drill assembly of FIG. 6A.
Figure 6E:
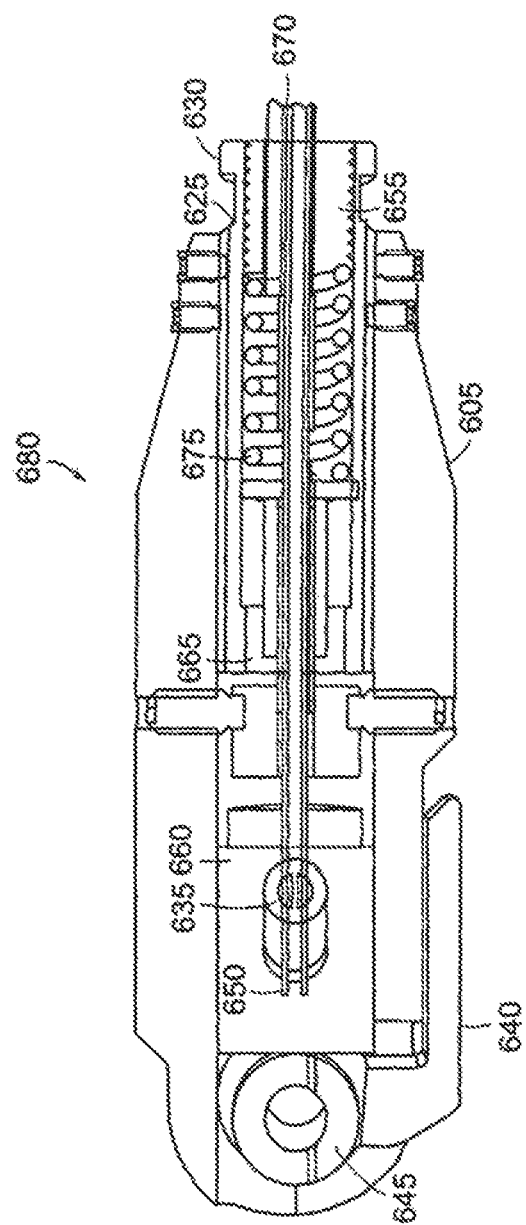
FIG. 6E is a schematic cross-sectional side view of the handle of the drill assembly of FIG. 6A through a central elongate axis of the drill assembly.

An example of a drill assembly inserted into a patient can be seen in FIG. 5B, with an example of a reamer assembly inserted into a patient shown in FIG. 5C. In one embodiment of the invention the drilling devices and/or reamer devices described herein may include a balloon element, such as a balloon catheter, at a distal portion thereof. This balloon catheter may be configured to expand and contract, upon actuation by a user, to increase the size of the cavity created within the bony structure. An example drill assembly including a multi-lumen balloon catheter assembly is shown in FIGS. 7A-7F.

Curved Drilling Device with Balloon Element

In one embodiment of the invention, a drilling device including a balloon element may be inserted through the cannula to drill a hole, such as, but not limited to, a curved hole, in the vertebral body. Upon drilling the hole, the drilling device can position a balloon element, located at a distal end of the drilling device, within the curved hole. This balloon element may then be expanded, or otherwise deployed, to expand the size of the hole inside the vertebral body. The balloon element may thereafter be retracted back to its original unexpanded state for removal of the drilling device, thereby leaving an expanded hole within the vertebral body. An example curved drilling device including a balloon element is shown in FIGS. 7A-7F.

In one embodiment, the drilling device may include a drilling element capable of forming a curvilinear pathway within a bony structure. This drilling element may, in one embodiment, be contained within one lumen of a multi-lumen balloon catheter. For example, in one embodiment, the flexible non rotating slotted metal tube 322 of the curved drill device 300 may be located within one lumen of a multi-lumen balloon catheter, with a balloon element located at a distal end of the catheter.

In the embodiment shown in FIGS. 7A-7F, a multi-lumen balloon catheter assembly 705 is coupled to a drilling device 710. The drilling device 710 may include a drill tip 715 located at a distal end of a hollow, non-rotating elongate slotted tube 720. The drill tip 715 may be connected to, and driven by, a torque tube 725 extending through the slotted tube 720 to a drive element located at a proximal end of the slotted tube 720. The drill tip 715 may be connected to the torque tube 725 at a connecting location 722 by any appropriate means, such as, but not limited to, bonding, crimping, tying, or any other appropriate mechanical, and/or adhesive means. As described above, the drilling device 710 may additionally include elements such as a handle (not shown), a key component 730, a feedscrew assembly 735, a spring element 740, and a retainer element 745.

In one embodiment, the multi-lumen balloon catheter assembly 705 may be placed over the torque tube 725 and extend along a length thereof. The multi-lumen balloon catheter assembly 705 may include a first hollow shaft, or drill lumen, 750 configured to extend around the torque tube 725, and a second hollow shaft, or balloon lumen, 755 extending along at least one side of the first hollow shaft 750. At a proximal end 757, the balloon lumen 755 is connected to a luer connection 760, such as, but not limited to, a luer lock portal, check valve, or other connecting portal, that may be configured to releasably mate with a fluid dispensing device 765, such as a syringe or other fluid dispensing device, for holding a fluid 767. The fluid may include, but is not limited to, a liquid, such as a saline solution, water, a radio-opaque contrast media, and/or any other appropriate solution, or a gas. The walls of the multi-lumen balloon catheter assembly 705 may, in one embodiment, be sufficiently thin to allow the multi-lumen balloon catheter assembly 705 to remain flexible and/or steerable, yet strong enough to contain a fluid under pressure. In general, the multi-lumen balloon catheter assembly 705 may be mounted onto, and used in conjunction with, any of the drilling devices and/or reaming devices described herein.

The luer connection 760 may, for example, be located within a handle sub-assembly and/or feedscrew assembly 735 of the drilling device 710. In one embodiment, the balloon lumen 755 may pass through one or more holes in the feedscrew assembly 735 and within the core of the handle of the apparatus so that the device may fit and lock to the access cannula. The luer connection 760 may be located proximate to the handle in a manner that allows the handle to rotate freely in order to drive the drill tip 715 and engage the feedscrew assembly 735. The balloon lumen 755 may provide a conduit for fluid under pressure to fill the distal balloon end of the catheter. The balloon lumen 755 may be of a small diameter relative to the first hollow shaft 750, which contains the drilling device 710. The balloon lumen 755 may be incorporated within the wall of the multi-lumen balloon catheter assembly 705, or extend along an outer or inner surface of the multi-lumen balloon catheter assembly 705.

The distal end 770 of the balloon lumen 755 includes an exit port 780 in fluid communication with the interior 772 of a balloon element 775 located at a distal end of the multi-lumen balloon catheter assembly 705 near the drill tip 715 of the drilling device 710. The balloon element 775 is sealably coupled to the first hollow shaft 750 at a distal end 782 and a proximate end 784, thereby providing a sealed balloon element 775 that may expand and contract in response to the injection and removal of a fluid through the balloon lumen 755 and into the interior 772 of the balloon element 775. The balloon element 775 may be sealably connected to the first hollow shaft 750 by any appropriate mechanical and/or adhesive means, such as, but not limited to, bonding, pressure fitting, or clamping. In an alternative embodiment, the balloon element 775 may be attached directly to the non-rotating slotted tube 720 of the drilling device 710, with a balloon lumen 755 extending along, and optionally attached directly to, the slotted tube 720.

In one embodiment the drilling device 710 may be slideably inserted through the first hollow shaft 750 of the multi-lumen balloon catheter assembly 705. The multi-lumen balloon catheter assembly 705 may, in one embodiment, be bonded, or otherwise fixedly connected, through adhesive and/or mechanical means, to the drilling device 710 at least one location, or be held in location through a pressure fitting. In an alternative embodiment, the multi-lumen balloon catheter assembly 705 may be molded, or otherwise formed, over the drilling device 710, or be mounted onto the drilling device 710 by any other appropriate means. The first hollow shaft 750 and/or balloon lumen 755 may be manufactured from materials including, but not limited to, polymers, metals, such as, but not limited to, nickel titanium (i.e. NiTi, or Nitinol), aluminum, or other appropriate metal, plastics, composite materials, or combinations thereof, and may possess any appropriate plastic and/or elastic properties, as appropriate. The multi-lumen balloon catheter assembly 705 may be extruded, molded, machined, or otherwise manufactured, as appropriate. In one embodiment, the multi-lumen balloon catheter assembly 705 may be removable, thereby allowing the drilling device 710 to operate with or without the multi-lumen balloon catheter assembly 705.

In one embodiment, the balloon element 775 may be constructed from an elastically deformable polymeric material such as, but not limited to, a natural or synthetic rubber material. For example, in one embodiment, the material for the balloon element is one that will resist puncture at inflation pressures as high as 25 atm, such as, but not limited to, polyurethane or mylar. In its undeformed configuration, the balloon element 775 may lie flush, or substantially flush, with the outer surface of the multi-lumen balloon catheter assembly 705, thereby minimizing the cross-section of the multi-lumen balloon catheter assembly 705 and drilling device 710 during insertion and removal of the distal end into the vertebral body, or other bony structure. The balloon element 775 may then be expanded out from the surface of the multi-lumen balloon catheter assembly 705 upon injection of a fluid through the balloon lumen 755 and into the interior 772 of the balloon element 775. An example of a balloon element 775 after expansion can be seen in FIGS. 7A, 7C, and 7F. Upon removal of the fluid from the interior 772 of the balloon element 775, the balloon element 775 may return to its original, undeformed, configuration prior to removal of the multi-lumen balloon catheter assembly 705 and drilling device 710 from the vertebral body.

In one embodiment, the distal end 782 of the balloon element 775 may fixed approximately 1 mm proximal to the drill tip 715 of the drilling device 710. In an alternative embodiment the balloon element may be placed closer to, or further away from, the drill tip 715 along the elongate length of the multi-lumen balloon catheter assembly 705 and drilling device 710. In one embodiment, the balloon element 775 may be configured to form a specific shape upon expansion, such as, but not limited to, a cylinder, sphere, oval shape, cube, or oblong shape. This may be achieved, for example, by manufacturing the balloon element 775 from multiple materials and/or multiple thicknesses of material, having different elastic properties, and/or by including restraining elements within the balloon element 775 to restrain the expansion of the balloon element 775 in certain directions.

In an alternative embodiment, the balloon element 775 may only extend over a portion of the circumference of the multi-lumen balloon catheter assembly 705, and thereby only expand out over a portion of the circumference of the multi-lumen balloon catheter assembly 705 upon injection of the fluid. For example, in one embodiment, the balloon element 775 may only extend over the inner curve of the curved distal end of the multi-lumen balloon catheter assembly 705 and drilling device 710, and therefore only expand inwards towards the central portion of the vertebral body upon expansion by the fluid. In a further alternative embodiment, the balloon element 775 may extend over the entire circumference of the multi-lumen balloon catheter assembly 705, but be restrained to only expand in one or more directions by a restraining element, such as, but not limited to, a non-deformable cover element attached over a portion of the balloon element 775.

In one embodiment, the multi-lumen balloon catheter assembly 705 may include a plurality of balloon elements 775 located at different circumferential positions on the multi-lumen balloon catheter assembly 705 and/or at different locations along the length of the multi-lumen balloon catheter assembly 705. Each of the plurality of balloon elements 775 may be in fluid communication with a different balloon lumen 755. Alternatively, a single balloon lumen 755 may be configured to be in fluid communication with some or all of the plurality of balloon elements 775. For example, in one embodiment, the multi-lumen balloon catheter assembly 705 may include a plurality of balloon elements 775 each located at the same distance from the drill tip 715 and spanning a portion of the circumference of the multi-lumen balloon catheter assembly 705. These balloon elements 775 may be expanded separately, thereby allowing the controlled expansion of a cavity within a bony structure by different amounts in different radial directions.

Figure 7A:
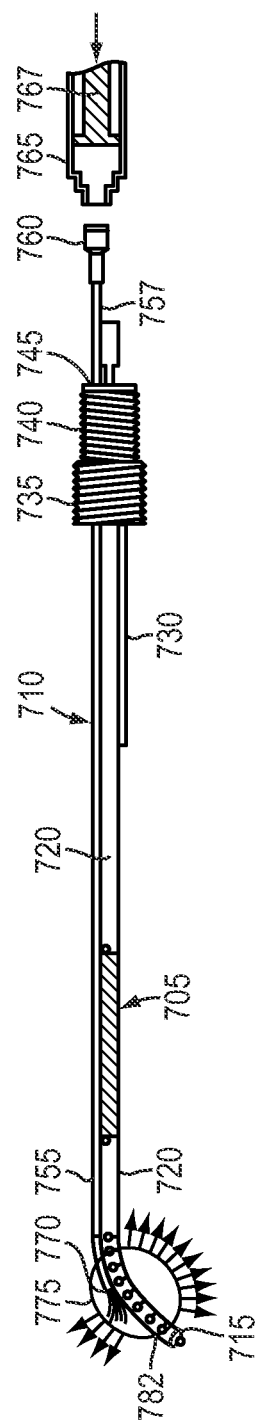
FIG. 7A is a schematic side view of a slotted tube sub-assembly for a drilling device with a balloon element mounted thereto, in accordance with one embodiment of the invention.
Figure 7B:
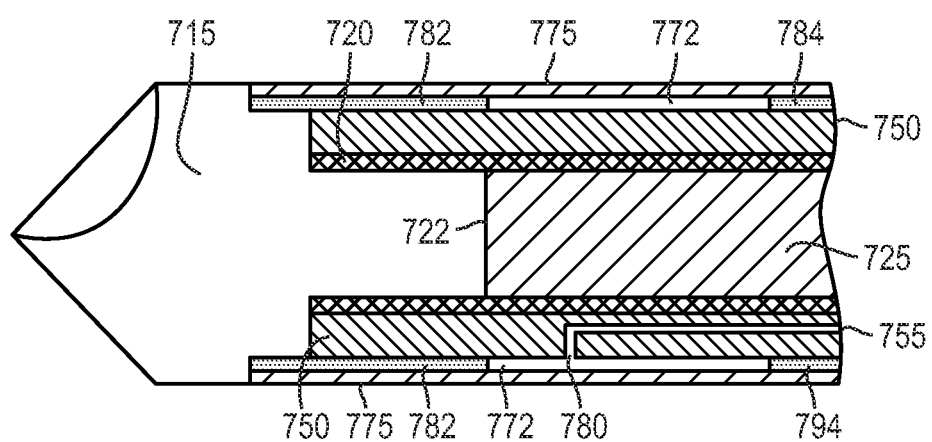
FIG. 7B is a cross-sectional side view of the distal end of the slotted tube sub-assembly of FIG. 7A with the balloon element in a deflated configuration.
Figure 7C:
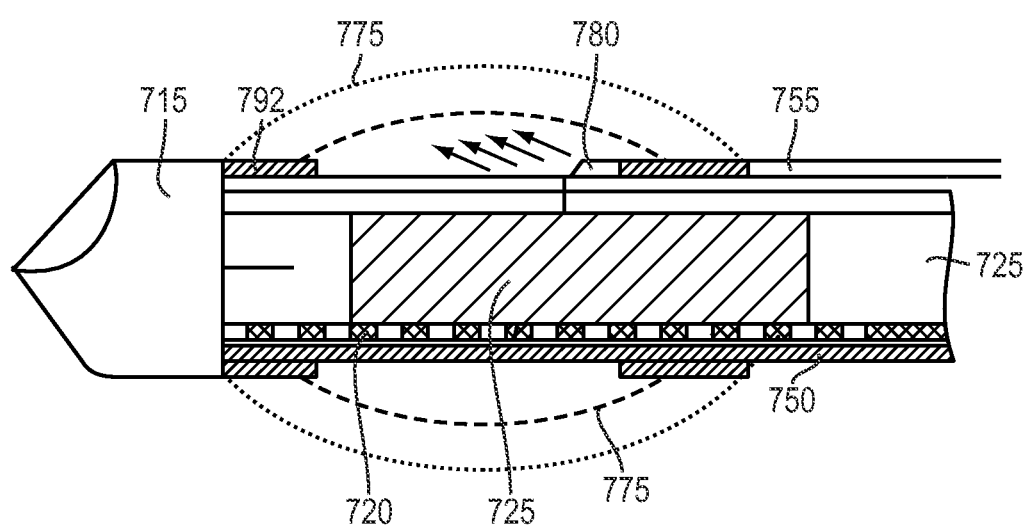
FIG. 7C is a cross-sectional side view of the distal end of the slotted tube sub-assembly of FIG. 7A with the balloon element in an inflated configuration.
Figure 7D:
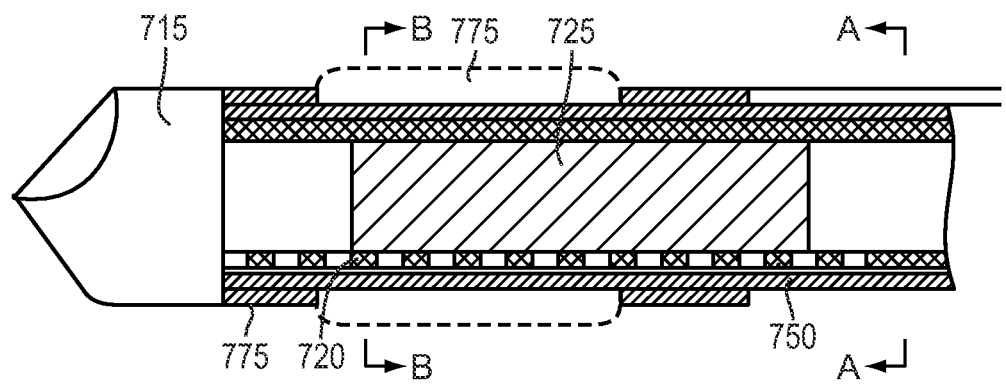
FIG. 7D is another cross-sectional side view of the distal end of the slotted tube sub-assembly of FIG. 7A with the balloon element in a deflated configuration, including the sections A-A and B-B.
Figure 7E:
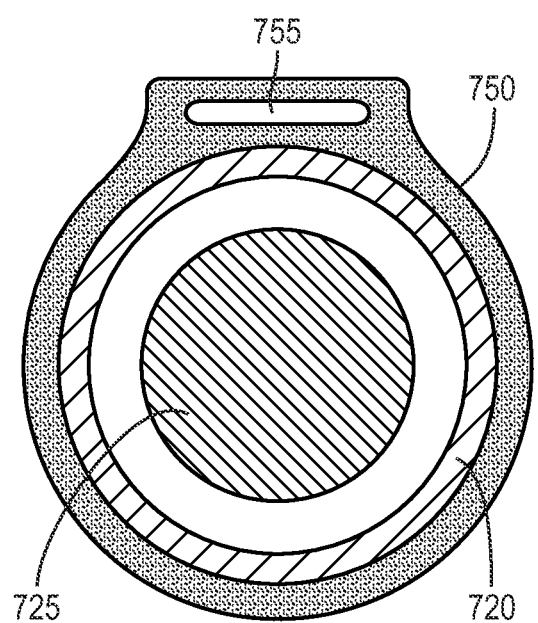
FIG. 7E is a cross-sectional end view of the slotted tube sub-assembly of FIG. 7A at section A-A.
Figure 7F:
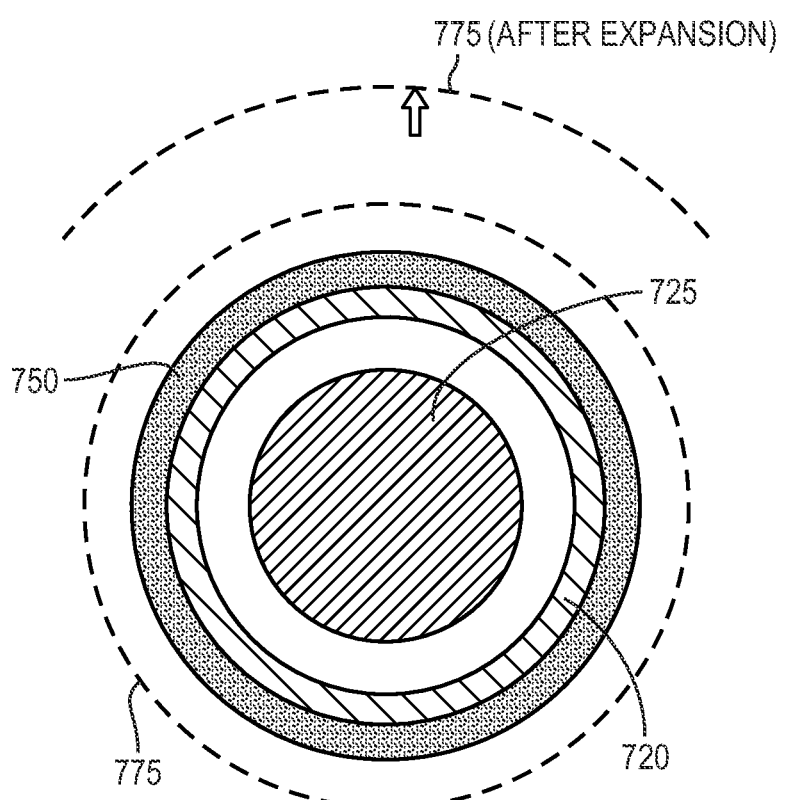
FIG. 7F is a cross-sectional end view of the slotted tube sub-assembly of FIG. 7A at section B-B showing the deflated balloon element and radial expansion of the balloon wall.

In operation, a cavity may be formed within a vertebral body or other bony structure, such as, but not limited to, a target location within a vertebral body containing broken bone fragments. In one embodiment, a method of creating a cavity, such as a curvilinear cavity, within a vertebral body may include the use of a multi-lumen balloon catheter assembly 705 and drilling device 710. As the distal end of the multi-lumen balloon catheter assembly 705 and drilling device 710 are advanced into the bone, the multi-lumen balloon catheter assembly 705 is translated to the desired target location within the bony structure. Once the position of the drill tip 705 and balloon element 775 have been established, the fluid dispensing device 765 may be attached to the luer connection 760 located proximal to the drill handle assembly. The balloon element 775 may then be filled with fluid media 767 under pressure to cause the expansion of the balloon element 775 radially from the flexible drill shaft housing, as shown in FIGS. 7A, 7C, and 7F. Depending on the shape and material of the balloon element 775, the wall of the expanding balloon element 775 pushes or compacts surrounding bone and contacts fractured bone fragments to cause the movement of the fragments, thereby expanding the cavity within the bony structure to the required shape and volume. After expansion of the balloon element 775, the fluid 767 may be removed from the balloon element 775, through suction or any other appropriate means, and the balloon element 775 may return to its initial, unexpanded configuration. The distal end of the multi-lumen balloon catheter assembly 705 and drilling device 710 may then be removed from the bony structure, leaving behind the expanded cavity. Methods for inserting a drilling device into a bony structure, and manipulating the drilling tip of the drilling device within the bony structure, are described above for FIGS. 3A-3K.

After creation of the expanded cavity by the balloon element 775, a reaming device, such as the reamer device 400 described above in FIGS. 4A-4G, may be inserted into the cavity to further ream the cavity to the required shape and size prior to injection of bone cement and/or the insertion of a stent device into the cavity. Alternatively, a reaming device may not be required, and stent placement and/or bone cement injection may be performed immediately after the removal of the distal end of the multi-lumen balloon catheter assembly 705 and drilling device 710 from the bony structure.

In one embodiment, a multi-lumen balloon catheter assembly 705 and drilling device 710 assembly may include a means of adjusting the curvature of at least a portion of the elongate shaft of the multi-lumen balloon catheter assembly 705 and/or drilling device 710. Such a means may include, for example, a wire tensioner connected to the distal end of the flexible shaft of the multi-lumen balloon catheter assembly 705 and/or drilling device 710. By applying a tension force to the wire tensioner, the shaft of the apparatus may flex to a preferred radius. This tension force may be applied, in one embodiment, by a manually operated lever, an integrated spring, and/or a combination in which a spring force may be modified by a dial-able knob or manually operated lever. By controlling the flexibility of the shaft of the multi-lumen balloon catheter assembly 705 and/or drilling device 710 at given locations, such as at the distal end of the shaft, the shaft can be configured to preferentially buckle at a given position, and in a given direction, upon application of a force to the wire tensioner. This may be beneficial, for example, in guiding the distal portion of the multi-lumen balloon catheter assembly 705 and/or drilling device 710 to a target location within a bony structure. The flexibility of sections the shaft may be controlled through careful material selection for the shaft, or portions thereof, through changes in thickness of portions of the shaft, and/or through slots or other elements within the shaft configured to allow preferential buckling in one or more set directions.

In one embodiment, a straight or curved guide wire may be removably inserted into a hollow portion of a shaft of the multi-lumen balloon catheter assembly 705 and/or drilling device 710 to support and/or change the curvature of at least a portion of the shaft. This guide wire may be beneficial, for example, in assisting the apparatus in entering the bony structure along a substantially straight or curvilinear path, and/or in holding the apparatus in a desired curved or straight configuration prior to, during, and/or after use.

In an alternative embodiment, a multi-lumen balloon catheter assembly 705 may be coupled to a reamer device, such as, for example, the reamer device 400 described above for FIGS. 4A-4G. For example, regardless of surgical sequence selected, a multi-lumen balloon catheter assembly 705 including a balloon element 775 may be mounted to the flexible shaft housing of a reamer device in the same way as for the drilling device 710 described above, as both the reamer devices and drilling devices described herein may incorporate a flexible shaft housing and handle assembly.

In one embodiment, a reamer device incorporating a multi-lumen balloon catheter assembly 705 may provide a means for creating a hole that is significantly larger in diameter than the flexible shaft housing. In operation, one or more balloon elements may be expanded within the bony structure after reaming of a cavity by the reaming element. As a result, by creating a larger cavity prior to expanding the balloon element, the initial force to expand the balloon element may be decreased, resulting in the probability of fully inflating the balloon increasing. In an alternative embodiment, one or more balloon elements may be expanded, and thereafter collapsed, prior to reaming, thereby forcing material away from the shaft and reducing the material that must be reamed in order to form the cavity.

In one embodiment of the invention, the balloon element 775 may be able to expand with sufficient force to provide a distraction force to the end plates of a compressed vertebral body. In an alternative embodiment, the balloon element 775 may be specifically configured to expand without providing any distractive force sufficient to move the end plates of the vertebral body. In this case, the balloon element may, upon expansion, merely create a cavity within the vertebral body without changing the shape or location of the outer walls of vertebral body.

In an alternative embodiment, the balloon element 775 may be detachably mounted at the distal end of the multi-lumen balloon catheter assembly 705 and/or drilling device 710. In this embodiment, a release mechanism may be included to allow the balloon element 775 to be detached and left in the vertebral body when the drilling device 710 is removed. As a result, the balloon element 775 may be filed with a bone cement, or other sufficiently viscous material, to allow the balloon element 775 to be left within the vertebral body and act as a structural support element for the vertebral body. In this embodiment, the balloon element may be a permeable or impermeable stent type structure.

In a further embodiment, the balloon element 775 may be formed, in an expanded configuration, from a shape memory material, such as Nitinol. The balloon element 775 may then be collapsed down to a contracted configuration for insertion into the vertebral body, or other bony structure, and held in a contracted configuration by, for example, a mechanical and/or magnetic locking mechanism. Upon release of this locking mechanism the balloon element 775 may thereafter self-expand without the need for injection of a fluid. The balloon element 775 may thereafter be re-collapsed and removed, leaving the expanded cavity within the vertebral body.

Another example drilling device with balloon element is shown in FIGS. 8A-8J. In this embodiment, the device 800 includes a drill tip 805 mounted at a distal end of a rotating torque tube or drive shaft coil 810 which is in turn mounted to a rotating drive shaft 815. The drive shaft coil 810 includes a multi-filar coil including a plurality of flexible wire elements, thereby allowing the drive shaft coil 810 to exert a torque on the drill tip 805 while allowing the drive shaft coil 810 to bend and rotate about a curvilinear central axis of the device 800. The drill tip 805 may be formed from a material such as, but not limited to, a metal (e.g. stainless steel or tungsten). The drive shaft coil 810 may include, for example, a single, dual, or three layer multi-filar coil. The drive shaft 815 is a rotating, non-flexible section connected to the drive shaft coil 810 and extending back to a rotating drive mechanism within a handle of the device 800 (not shown). In one embodiment, the drive shaft 815 is formed from a metal (e.g. stainless steel) wire or a thick walled hypotube. In operation, the drive shaft 815 provides torque to the drive shaft coil 810, which in turn rotates the drill tip 805. In an alternative embodiment, the non-flexible drive shaft 815 is not required, with the flexible drive shaft coil 810 extending along the full length of the device to the handle. In a further alternative embodiment, the non-flexible drive shaft 815 extends out to the drill tip 805, with no drive shaft coil 810 required.

An expandable and collapsible balloon element 820 is placed at a distal end of the device 800 behind the drill tip 805. In one embodiment, the drill tip 805 extends a set distance beyond the balloon element 820. In an alternative embodiment, the drill tip 805 is placed directly beyond, and abutting, a pull wire band 855 at a distal end of the balloon element 820. The pull wire band 825 provides an anchor for a distal end of the balloon element 820, and further provides an anchor for one or more pull wires 855 which extend from the pull wire band 825 through a hollow tube or shaft 835, e.g. a hollow polymer shaft, and provide a means for imposing a preset and adjustable curvature to the flexible distal end of the device 800. In operation, by pulling on the pull wire 855, a user can curve the distal end of the device 800 by a set amount, thereby allowing the drill tip 805 to drill a curvilinear cavity within a vertebral body or other target site. In one embodiment, the pull wire 855 is placed within a pull wire lumen which extends through and/or between one or more layers of the hollow shaft. In one embodiment, the pull wire lumen is a thin walled polyimide shaft with tetrafluoroethylene (TFE) filler. The pull wire 855 may be formed from a material such as, but not limited to, a metal such as stainless steel, tungsten, or Nitinol, a synthetic fiber, or combinations thereof. The pull wire 855 may be welded, glued, threaded through, or otherwise attached to the pull wire band 825.

An inflation lumen 840 extends through the outer hollow shaft 835 and provides a fluid channel through which a fluid can be flowed to expand the balloon element 820. In an alternative embodiment, the inflation lumen 840 may extend between the outer hollow shaft 835 and an inner hollow shaft 845, e.g. a high pressure polymer inner shaft. The inflation lumen 840 may include a thin walled polyimide shaft configured to handle a high pressure flow therethrough. The inner hollow shaft 845 may, in one embodiment, be a coiled polyimide shaft. The polyimide shaft may, in one embodiment, have an outer layer that is thermally compatible with the balloon element 820. The thermal compatibility allows thermal bonding of the shaft outer layer with the balloon element rather than a glue bond.

The balloon element 820 may, in one embodiment, be constructed from polyurethane. In an alternative embodiment, the balloon element 820 may be constructed from a material including, but not limited to, a plastic, a metal (e.g., Nitinol), and/or a polymer. The balloon element 820 is collapsible to a minimal diameter, i.e. substantially the outer diameter of the shaft 835, to allow the distal end of the device 800 to be deployed through a cannula and into a target location within a body. In one embodiment, the balloon element 800 may be expanded by forcing a fluid (e.g., a saline solution, water, or a gas such as, but not limited to, air) into the interior of the balloon element 820 through the inflation lumen 840.

The balloon element 820 may expand to form any appropriate expanded shape including, but not limited to, a sphere, a cylinder, or a curvilinear cylinder. In one embodiment, different portions or the wall of the balloon element 820 have different wall thicknesses, thereby forcing the balloon element 820 to expand preferentially in a predetermined direction corresponding to the sections having a thinner wall. As a result, the balloon element 820 may be designed to inflate in any set direction by any set amount, thereby allowing the device 800 to form cavities of any appropriate size and shape, as required for a particular vertebral body and/or treatment. In one embodiment, the balloon may have a multi-layered structure. For example, the balloon may be formed with a compliant outer layer and a substantially non-compliant inner layer. The outer layer may, for example, be polyurethane, while the inner layer may, for example, be nylon. The compliant outer layer adds strength and puncture resistance while the inner non-compliant layer provides the desired inflated shape or volume.

The device 800 may, in one embodiment, include one or more axial stiffening wires 850. The stiffening wire(s) 850 may extend along a length of the shaft 835, or a portion thereof, and provide structural support to the shaft 835 to prevent the shaft 835 from bending or buckling when not pulled by the pull wire 855, and/or to prevent the shaft 835 from bending in directions other than that required to form the required curvilinear cavity. The stiffening wire(s) 850 may extend in a helical pattern, as shown for example in FIG. 8F, or may extend generally straight longitudinally along the shaft 835. The stiffening wire 850 may be formed from a material such as, but not limited to, a metal such as stainless steel, tungsten, or Nitinol, a synthetic fiber, or combinations thereof.

Figure 8F:
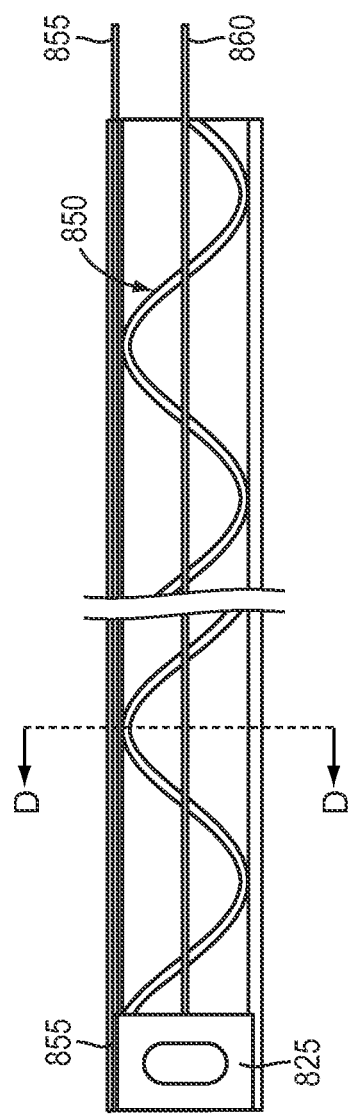
FIG. 8F is a cross-sectional side view of a pull-wire and band for the drill assembly and balloon element of FIG. 8A.
Figure 8G:
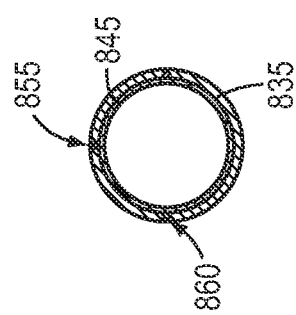
FIG. 8G is a cross-sectional end view of the pull-wire and band of FIG. 8F through section D-D.
Figure 9D:
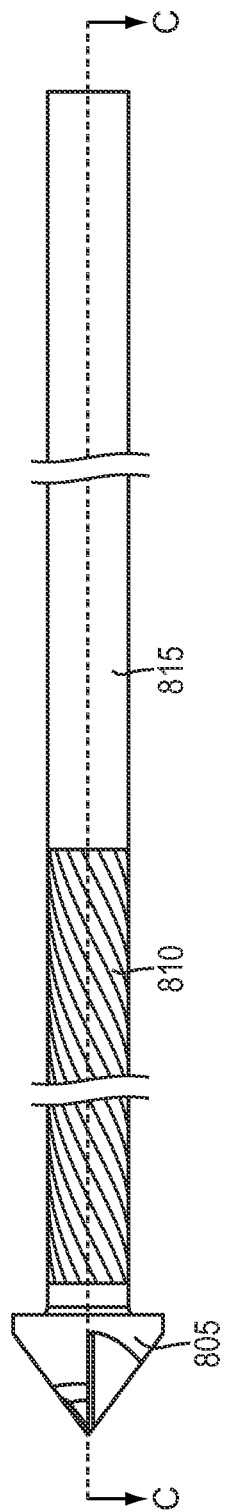
FIG. 9D is a schematic side view of a drill tip and shaft for the drill assembly of FIG. 9A.
Figure 9E:
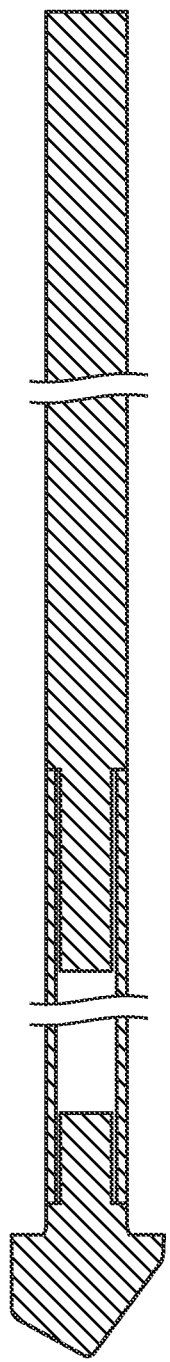
FIG. 9E is a cross-sectional bottom view of the drill tip and shaft of FIG. 9D through section C-C.
Figure 9G:
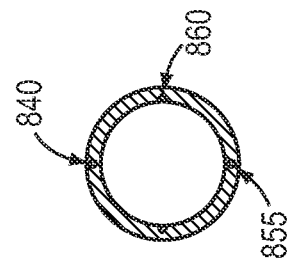
FIG. 9G is a cross-sectional end view of the pull-wire and band of FIG. 9F through section D-D.
Figure 9F:
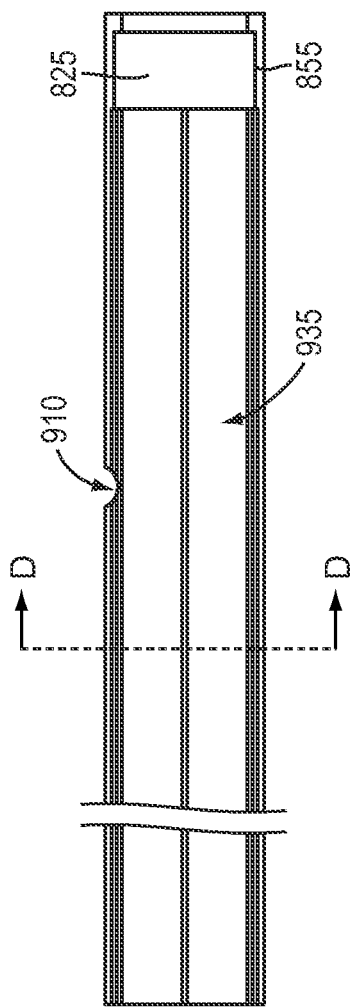
FIG. 9F is a cross-sectional side view of a pull-wire and band for the drill assembly and balloon element of FIG. 9A.

In one embodiment, the device 800 may include a plurality of pull wires. For example, a first pull wire 855 may be used to produce a first curvature in the distal end of the device 800, while secondary axial pull wires 860 may be used to produce further curvatures in the distal end of the device 800 in different directions to that imposed by the first pull wire 855. As a result the direction of the drill tip 805 may be steered through a body by manipulation of the plurality of pull wires 855, 860. An example multi-pull wire configuration for the device 800 is shown in FIGS. 8F and 8G. In one embodiment, one or more pull wires 855, 860 is connected to a cam assembly, as described hereinabove, to allow a user to pull on the one or more pull wires 855, 860. In an alternative embodiment, the pull wires 855, 860 may be controlled by control elements including, but not limited to, a sliding element, a threaded element, a levered element, a motorized element, and/or a magnetic element. In one embodiment, the pull wire 855, 860 may be spring loaded to produce a pre-load on the pull wire 855, 860 to induce a pre-loaded, but flexible, curvature in the distal end of the device 800. Use of a spring element to induce a pre-loaded curvature in the distal end of the device 800 allows the distal end or the device to be straightened during insertion through a straight cannula, and thereafter return to its curved configuration after insertion through the cannula.

The device 800 may include a feed screw 862, (e.g., an injection molded lead screw), with an integrated key component 865. The key component 865 is adapted to mate with a slot in a cannula to ensure correct orientation of the device 800 within the cannula, as described hereinabove. In an alternative embodiment, no key component 865 is required. The feed screw 862 provides a threaded mating with a handle assembly (not shown) to provide a rotational and axial driving motion to the drill tip 805 upon rotation of the handle assembly, as described hereinabove.

In one embodiment, the outer shaft 835 extends from a proximal end of the device 800 to the proximal end of the balloon element 820, with the pull wire band 825 and the distal end of the outer shaft 835 providing sealed mating surfaces onto which the balloon element is attached. In this embodiment, the inflation lumen 840 extends from the distal end of the outer shaft 835 into an interior of the balloon element 820. In an alternative embodiment, as shown in FIGS. 9A-9J, an outer shaft 935 extends out to a distal end of the pull wire band 825. In this embodiment, the balloon element 820 is sealing mounted over the outer shaft 835, with a hole 910 providing a portal through which fluid from the inflation lumen 840 may be flowed into the interior of the balloon element 820. In various embodiments of the invention, the outer shafts 835, 935, and/or inner shaft 845 may be constructed from braided material such as, but not limited to, a braided multi-lumen polymer material. In one embodiment, the braid includes tri-axial wires. In an alternative embodiment, any multi-lumen or single lumen structures may be used for the shafts. In one embodiment, the inner shaft 845 and/or outer shafts 835, 935 may have a lower durometer (hardness) at a distal end portion, with a higher durometer (hardness) at a proximal end portion thereof.

In one embodiment the inflation lumen 840 is coupled at a proximal end to a portal element. The portal element allows a syringe or other fluid injecting and removing device to be releasably coupled to the inflation lumen 840 to controllably inject fluid into the balloon element 820 to expand a cavity within a body, and to controllably remove the fluid from the balloon element 820 prior to removing the device 800 from the body. The portal element may include, but is not limited to, a rotatable fitting on a side of the handle assembly and/or a centrally located, non-rotatable fitting at a center of the proximal end of the handle assembly. The portal element may include a luer lock or other appropriate fitting. The portal element may be covered, when not in use, by a cap, sleeve, or other suitable imperforate closure.

In operation, as described hereinabove, the distal end of the device 800 may be inserted through a cannula and into a bony structure such as, but not limited to, a vertebral body. The distal end of the drill device may be manipulated by rotating and axially extending the drill tip 805 to create a curvilinear void in the bony structure. This void can then be enlarged by expansion of the balloon element 820 mounted to the drill device, after which the balloon element 820 is deflated and the distal end of the device 800 is removed from the cannula.

In one embodiment of the invention, the drill tip 805 may include a reaming element, as described herein above, with the reaming element being used to ream out a curvilinear cavity of a first diameter, with the balloon thereafter being used to further expand the curvilinear cavity. Alternatively, the balloon may be used to further expand a cavity after reaming.

Figure 10L:
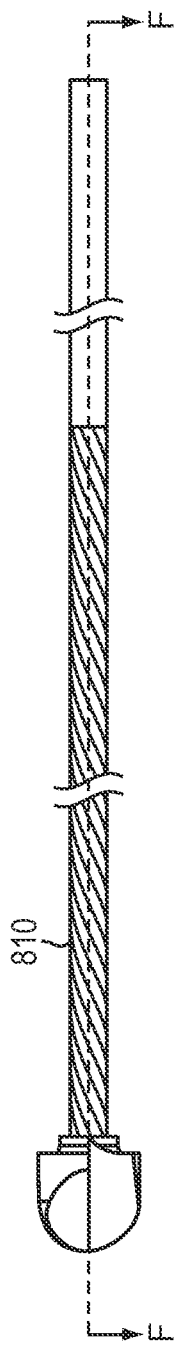
FIG. 10L is a schematic side view of a drill tip and shaft for the drill assembly of FIG. 10A.
Figure 10M:
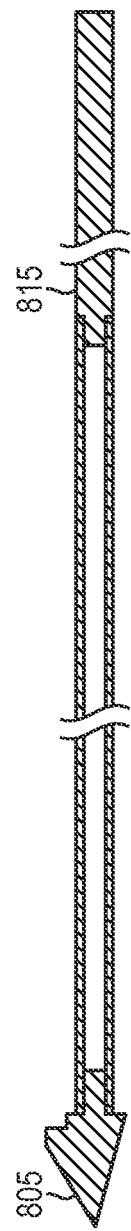
FIG. 10M is a cross-sectional bottom view of the drill tip and shaft of FIG. 10L through section F-F.
Figure 11G:
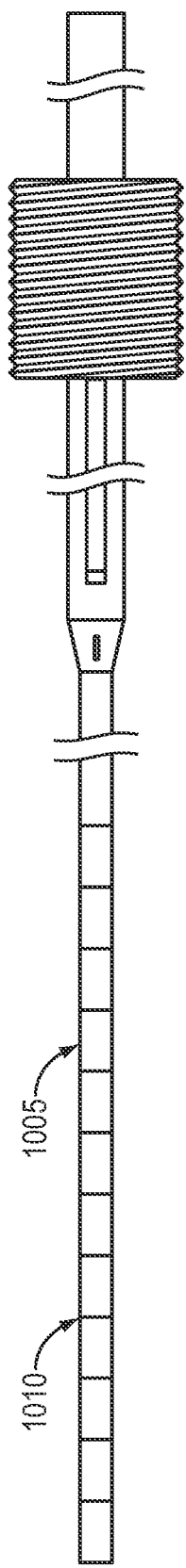
FIG. 11G is a schematic top view of a slotted deflection shaft for the drill assembly of FIG. 11A.
Figure 11H:
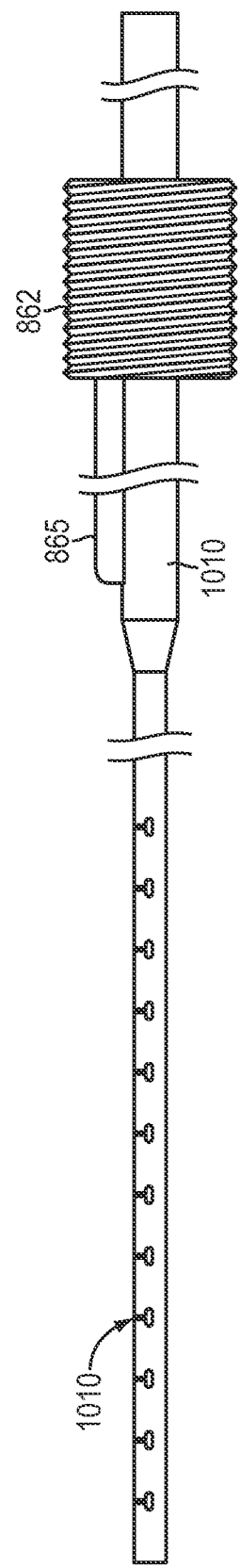
FIG. 11H is a side view of the slotted deflection shaft of FIG. 11G.

In one embodiment of the invention, a curvature at a distal end of a drilling device with balloon element may be provided by means other than a pull wire. For example, a curved distal portion for a drill assembly with balloon element may be formed using elements such as, but not limited to, a shaft with one or more slots cut therein, a shaft comprising a portion that bends in response to an electromagnetic signal, or a pre-molded curved shaft. An example drilling device 900 with a collapsible balloon element 820 and a slotted shaft 905 is shown in FIGS. 10A-10O. In this embodiment, the device 900 includes a deflection shaft 905 having a plurality of slots 910 along a distal portion of one side of the deflection shaft 905. In an alternative embodiment, slots 910 may be centered around more than one radial position on the distal end of the deflection shaft 905, thereby allowing for bending of the distal end of the deflection shaft 905 in more than one plane.

The deflection shaft 905 is positioned within a hollow tube or shaft 835, with an expandable and collapsible balloon element 820 placed over the deflection shaft 905 at a distal end of the device 900 behind the drill tip 805. The deflection shaft 905 may be formed from a material including, but not limited to, a metal (e.g. stainless steel, Nitinol, aluminum), a polymer, and/or combinations thereof. In one example embodiment, the deflection shaft 905 is formed from a stainless steel hypotube with slots 910 laser cut into the distal end of the deflection shaft 905. In various embodiments, the slots 910 may be laser cut, molded, etched, or otherwise formed in the shaft 905.

The deflection shaft 905 may be placed inside an outer shaft 835 that extends from a proximal end of the device 900 to the proximal end of the balloon element 820. An additional outer shaft section 935 may extend from a distal end of the balloon element 820 to a distal end of the deflection shaft 905, with the drill tip 805 extending from the distal end of the deflection shaft 905. In one embodiment, the deflection shaft 905 may be covered by a sleeve 915. The sleeve 915 may, for example, be a high pressure sleeve formed from a material such as, but not limited to, a thin wall polyimide shaft.

The device 900 may include a feed screw assembly 864, including a feed screw 862 and key component 865, for movably coupling the assemble 900 to a handle portion (not shown). One or more inflation lumens 840 may extend from the proximal end of the device 900 into the interior of the inflatable balloon element 820 to provide a fluid passageway for injecting and removing fluid from the balloon element 820 to inflate and deflate the balloon element 820 as required.

A puller element 920 may be placed within the deflection shaft 905 to provide a means of adjustably controlling the curvature of the distal end of the deflection shaft 905. An anchoring portion 925 of the puller element 920 may be welded, or otherwise bonded, to the distal end of the deflection shaft 905, with the remainder of the puller element 820 free to slide axially with respect to the deflection shaft 905. One or more alignment holes 930 may be incorporated into the anchoring portion 925 to assist in the aligning of the puller element 820 with the deflection shaft 905 prior to welding the anchoring portion 925 to the deflection shaft 905.

In operation, the puller element 920 is anchored at a proximal end 940 to a handle portion (not shown). This connection between the puller element 920 and the handle portion may be spring loaded and/or adjustable or non-adjustable, as required. By applying a pulling force to the proximal end 940 the anchoring portion 925 pulls the distal end of the deflection shaft 905, thereby providing a bending force to the deflection shaft 905. The curvature of the distal end of the deflection shaft 905 is controlled by the force applied by the puller element 920, the deflection shaft 905 material, and the position of the slots 910 on the distal end portion of the deflection shaft 905.

One embodiment of the invention includes a drilling device 1000 having a deflection shaft 1005 which is integrally formed with a feed screw assembly 1015. As before, the feed screw assembly 1015 may include a feed screw 862 and key component 865. The drilling device 1000 may, for example, include a plastic feed screw assembly 1015 that is overmolded with or onto a deflection shaft 1005 having a plurality of slots 1010. An outer shaft 835 may then be positioned over the deflection shaft 1005. In one embodiment, a sleeve 915 may be placed over the deflection shaft 1005. An example drilling device 1000 including a deflection shaft 1005 with integrally formed feed screw assembly 1015 is shown in FIGS. 11A through 11H.

Method of Use

The devices discussed herein may be used in conjunction to provide a method of creating a curvilinear cavity within a vertebral body, or other bony structure. As disclosed herein, the creation of a curvilinear pathway and cavity within a vertebral body allows the cavity to extend over a potentially larger region of the interior of a vertebral body, and bisect an axis of the vertebral body using only a single point of access. After creation of a cavity in a damaged or diseased vertebral body, the cavity can be filled with a medical cement or other treatment element to stabilize the vertebral body and alleviate pain. As a result, the creation of a curvilinear pathway and cavity using these devices can enable the complete stabilization of a vertebral body from a single access incision, thus reducing the time needed for a surgical procedure and the damage caused to surrounding tissue and bone during a procedure. This can greatly improve the efficiency and safety of such a procedure.

In one embodiment of the invention, a procedure for using the devices disclosed herein can be used to produce a curvilinear cavity within a vertebral body. After location of the pedicle of the vertebral body, a needle assembly may then inserted percutaneously from the posterior approach through the outer tissue and anchored into the bone of the vertebral body to a suitable depth. This needle or wire will provide a guide for subsequent instruments. In one embodiment, the needle is a 1.5 mm diameter stainless steel pointed wire, although in other embodiments any appropriate diameter and material of needle may be used. The needle may be solid or hollow, depending upon the specific requirements of the procedure. An example of a guide wire or piercer 510 being inserted through the outer tissue 515 of a patient and into a vertebral body 520 by a posterior approach can be seen in FIG. 5A.

Once the guide wire 510 is in place, a trocar can be inserted into, and releasably coupled to a cannula, and the resulting trocar and cannula assembly slid over the guide wire 510. The trocar impact knob can be tapped with a hammer or other instrument to force the trocar forward to enlarge the hole in the vertebral body and thereby force the tip of the trocar and cannula into the bone. Once the trocar and cannula assembly have been correctly positioned, the trocar and the guide wire can be removed, thus leaving the cannula in place on its own. This cannula can then serve as a delivery path into the vertebral body for subsequent instruments.

A curved drilling device can then be inserted through the cannula to create a curvilinear pathway through the vertebral body. An example of a drilling device 525 being inserted through a cannula 530 and into a vertebral body 520 can be seen in FIG. 5B.

The drilling device 525 can be slideably placed within the cannula by aligning the key on the drill 535 with the slot on the cannula. The drilling device 525 can then be fully inserted and releasably locked to the cannula 530 by sliding a locking tab to the lock position, or otherwise securing the drilling device 525 to the cannula 530. In this position, the curved slotted tube of the drilling device 525 is constrained in the straight tube of the cannula 530 and the sharp drill tip is positioned at the end of the cannula 530. After the drilling device 525 is secured to the cannula 530, for example by the locking the flange to the cannula handle, the drive handle of the curved drill can be rotated to cause the rotation of the flexible drive shaft assembly and sharp tip.

Rotation of the flexible drive shaft assembly and sharp tip can also cause the simultaneous translation of the slotted tube and feedscrew assembly relative to the drive handle and cannula 530, thus translating the tip of the drilling device 525 into the vertebral body along a curvilinear path, provided the handle is locked to the cannula. For example, as it is being fed forward, the distal end of the drill shaft will begin to protrude from the cannula and starts to curve in the desired direction as it is cutting. The farther the drill shaft exits from the cannula, the greater the curved protrusion. As the drill tip rotates and travels in an arc, the resultant hole that it creates is also in an arc until the desired depth is achieved.

The sharp tip advances within the bone according to the pitch of the feedscrew. The advance of the tip of the drilling device 525 may be monitored fluoroscopically by the user, and/or the depth of drilling may be indicated by a scale printed or etched on the drilling device 525. When the path has been fully formed, the lock may be disengaged and the drilling device 525 removed from the cannula 530. The drilling device 525 can be removed by a counter rotation of the drill handle to withdraw the drill back into the cannula 530 and straighten the drill shaft in the process, after which the locking flange can be released and the drill assembly removed from the cannula 530. In an alternate embodiment, the drilling device 525 can be removed by simply unlatching it from the cannula 530 and pulling it out. This will, in turn, leave a hollow, curvilinear path through the vertebral body extending from the end of the cannula.

In embodiments of the invention including the use of a multi-lumen balloon catheter assembly in combination with the drilling device 525 (such as the balloon catheter assembly of FIGS. 7A-7G), forward advancement of the distal end of the drilling device may position the one or more balloon elements of the multi-lumen balloon catheter assembly within the bony structure. Once satisfactory drill tip and balloon element position has been achieved, the balloon element may be inflated by first attaching a fluid injector device to the fluid filling portal of the catheter, then injecting fluid under pressure into the balloon element, as described above. Upon pressurization, the balloon element will inflate radially from the flexible drill shaft housing. The size and shape of the expanded balloon element will depend on many factors, such as material selection, inflation pressure, bone anatomy, and bone strength. In one embodiment, the material for the balloon element is one that will resist puncture at inflation pressures as high as 10 atm, such as, but not limited to, polyurethane or polyester.

In one embodiment, a curved reamer device may then be inserted through the cannula to create the desired shape and size of curvilinear pathway through the vertebral body using the same basic surgical technique as for the drill device described above. An example of a reamer device 540 being inserted through a cannula 530 and into a vertebral body 520 can be seen in FIG. 5C. As discussed above, this reamer device 540 may include a multi-lumen balloon catheter assembly in addition to, or instead of, a multi-lumen balloon catheter assembly on the drilling device 525. In an alternative embodiment, the curved reamer device 540 is not required, with the cavity formed only by the drilling device 525 and attached multi-lumen balloon catheter assembly. In a further alternative embodiment, the drilling device 525 is not required, with the reaming device 540 configured to provide a drilling function upon entering the bony structure prior to reaming. Such a reaming/drilling device may, in one embodiment, also include a multi-lumen balloon catheter assembly mounted thereon.

The reamer device 540 can be inserted through the cannula 530. The reamer device 540 can then be releasably locked or latched to the cannula 530. During insertion of the reamer device 540, the moveable blade of the reamer is set in an undeployed position, located substantially along the axis of the shaft, so it may easily pass through the cannula 530. In one embodiment, the position of the reamer tip can be fluoroscopically confirmed.

The handle of the reamer device 540 can then be rotated to deploy and rotate the blade, with the reamer blade pivoting outward from the shaft and cutting a semi-sphere to a desired cavity diameter, without forward movement. This therefore forms a substantially semi-spherical proximal end of a cavity in the bone at the proximal end of the curvilinear path.

Once fully deployed, the blade can rotate and translate forward toward the anterior portion of the vertebral body 530 along a generally helical path in response to further rotation of the handle of the reamer device 540. The blade rotating action forms a generally curvilinear elongated hole. The speed of translation and cutting is dependent on the pitch of the feedscrew mechanism in the handle. The cavity created by the reamer device 540 may be monitored fluoroscopically to determine the length of the cavity, or the length may alternatively be monitored by a printed scale on the device. In an alternative embodiment, the blade may be initially placed at a distal end of the drilled hole and may be translated backwards towards the rear of the vertebral body to create the reamed cavity.

When cavity cutting is complete, the proximal end of the handle may be counter rotated to relax tension on the tether cable and allow the movement of the blade back to the closed or undeployed position. In one embodiment, at this point in the procedure, a balloon element mounted to the reamer device 540 may optionally be inflated, as described above. In this instance, the relatively larger cavity in the bone allows initial expansion the balloon element to occur at the minimum necessary pressure, thereby increasing the radial force of the balloon element wall when contacting the bone. The balloon element may then be deflated and the reamer device unlocked from the cannula 530 and removed. The resulting curvilinear cavity 550 is then free to have a treatment device, such as a stent and/or treatment material, such as bone cement, inserted into it.

The cannula 530 can then remain in place for insertion of other devices that will fill the cavity with medical cement. In one embodiment, these devices may include a stent and stent deployment apparatus, wherein the stent is filled with cement through the stent deployment apparatus to fill the curvilinear cavity and stabilize the vertebral body. After the cement injection procedure has been completed, the cannula 530 can be removed and the surgical incision closed.

Another embodiment of the invention can include a drill and/or reamer device including a lever and cam sub assembly or other mechanism to allow tension to be reduced in the spring assembly.

This can allow the spring force providing the curvature to the drill or reamer to be reduced during insertion and/or removal of the elongated tube assembly and drill tip, thus easing the insertion and removal of the drill or reamer from the working channel during use. An example curved drill device 600 including a lever and cam sub assembly, with the distal end of the drill straightened, can be seen in FIGS. 6A through 6E.

In the embodiment shown in FIGS. 6A-6E, the curved drill device 600 can include a drive handle 605, a sharp drill tip 610 attached to a flexible torque transmitting drive shaft 650 positioned within a slotted tube assembly 615, and a handle drive assembly positioned within the handle 605. The slotted tube assembly 615 can be a spring loaded, flexible, slotted metal tube. A key component 620 can be located on the slotted tube assembly 615 to ensure that, during operation, the drill 600 is inserted and locked into the working channel, such as a hollow cannula, in the desired circumferential orientation. A drill feed nut 625 including a locking flange 630 can be threaded onto the handle drive assembly 680 located within the handle 605. with the locking flange 630 providing a locking element for releasably locking the drill 600 to a cannula. A cable retaining pin 635 can be inserted within, and keyed to, the handle 605 to provide a torque retention device to anchor the proximal end of the flexible torque transmitting drive shaft 650. The cable retaining pin 635 can then drive the shaft 650 as the handle 605 is rotated.

The handle drive assembly 680 within the handle 605 includes a feed screw 655 onto which the feed nut 625 can be threaded. The cable retaining pin 635 is located within a cam pusher assembly 660 located within the central portion of the handle 605. A band retention element 665 is used to anchor a band 670 located within the slotted tube assembly 615, and anchored at its distal end to a distal portion of the slotted tube assembly 615, to provide the force necessary to produce a curvature at the distal end of the drill 600. A compression spring 675 is positioned between the feed screw 655 and the band retention element 665 to provide a spring force to the band retention element, thereby allowing the curvature of the distal end of the drill 600 to flex.

In addition, the curved drilling device 600 includes a lever 640 attached to a drill cam 645 mounted on the proximal end of the handle 605, wherein the lever 640 pivots the drill cam 645 about a central axis upon actuation by a user. The drill cam 645 includes an eccentric inner portion that abuts against a cam pusher assembly 660 located within the central portion of the handle 605. The cam pusher assembly 660 abuts against the band retention element 665, or other intermediate element. The band retention element 665 provides a stop for the compression spring element 675 located within the central axis of the handle 605 and configured to provide a spring force to the band retention element 665, thus providing the required force to the band 650 in order to maintain the distal end of the slotted tube assembly 615 in a curved configuration.

In operation, when the lever 640 is closed against the handle 605 of the drill 600, the compression spring 675 pushes the band retention element 665 and cam pusher assembly 660 against the drill cam 645, and provides the force necessary to produce a curvature at the distal end of the drill 600. However, when the lever is pulled away from the handle 605, it pivots the drill cam 645 about its axis and, due to the eccentric configuration of the drill cam 645, forces the cam pusher assembly 660 and band retention element 665 against the spring element 675. This has the effect of compressing and foreshortening the spring element 675, thus reducing the force provided to the distal end of the slotted tube assembly 615 and therefore allowing the distal end of the slotted tube assembly 615 to be straightened with less or minimal effort.

In another embodiment of the invention, a reamer, such as any of the reaming devices described herein, could include a lever and cam sub assembly or other mechanism to compress and foreshorten a compression spring within the handle of the reamer, thus allowing the distal end of the slotted tube assembly of the reamer to be straightened with less or minimal effort. In one embodiment, the lever and cam sub-assemblies may be incorporated into drilling devices and/or reaming devices including one or more balloon elements. Drilling and/or reamer devices including a lever and cam sub assembly may, in one embodiment, also include a multi-lumen balloon catheter assembly mounted thereon.

In alternative embodiments of the invention, any appropriate material, or combination of materials, may be used for the components described herein. Appropriate materials include, but are not limited to, stainless steel, aluminum, plastics, textiles, composite materials, or any combination thereof. The method of creating a cavity may include all, or only some of, the components described herein, depending upon the specific requirements of the system.

In further alternative embodiments of the invention, different drill and/or reamer devices can be used to create the cavity. These may include one or more blades or drill bits, looped or otherwise configured wires, or other drilling, boring, or reaming devices. The blades may be of any appropriate shape and configuration.

In one embodiment of the invention, a fiber optic camera device may be inserted into the cannula to provide images of the curvilinear pathway and cavity to a physician at any point during the procedure. The camera may also provide diagnostic information that may be used when determining the required size and shape of the cavity being created.

In alternative embodiments of the invention, the arc of the drilling device and/or reamer device may be selected to provide any shape of curvilinear cavity. Different arcs may be provided by selection of different tools, with each tool being set to provide one specific arc. Alternatively an individual device may be adaptably configured to provide an arc of any required curvature by the use of the spring tension mechanism described, or may be constrained preferentially to a substantially straight configuration, as needed, to achieve proper treatment in a bone fracture.

It should be understood that alternative embodiments, and/or materials used in the construction of embodiments, or alternative embodiments, are applicable to all other embodiments described herein.

The invention may be embodied in other specific forms without departing from the spirit or essential characteristics thereof. The foregoing embodiments, therefore, are to be considered in all respects illustrative rather than limiting the invention described herein. Scope of the invention is thus indicated by the appended claims, rather than by the foregoing description, and all changes that come within the meaning and range of equivalency of the claims are intended to be embraced therein.

What is claimed is:

1. An apparatus for forming a curvilinear void in bony structure, comprising:
    a curvilinear drilling device, comprising a handle and a flexible drill shaft assembly extending from a distal end of the handle, wherein the flexible drill shaft assembly includes a cutting tip located at a distal end of the flexible drill shaft assembly, a flexible rotatable drive shaft coupled to the tip, and a flexible, moveable and non-rotatable housing, wherein the distal end of the flexible drill shaft assembly includes a plurality of slots configured to allow the distal end to bend; and
    a multi-lumen balloon assembly having a hollow shaft and an expandable balloon element mounted on a distal portion of the hollow shaft,
    wherein the curvilinear drilling device is configured to be slidably inserted through the hollow shaft of the multi-lumen balloon assembly, and
    wherein the curvilinear drilling device and the multi-lumen balloon assembly are configured to be positioned within a vertebral body.

2. The apparatus of claim 1, wherein the balloon element is expanded by injection of a fluid into an interior portion thereof.

3. The apparatus of claim 1, further comprising a lumen in fluid communication with the balloon element.

4. The apparatus of claim 1, further comprising a pull wire band, wherein the pull wire band provides an anchor for a distal end of the expandable balloon element.

5. The apparatus of claim 1, wherein the cutting tip is adapted to form the curvilinear void by simultaneous rotation and curvilinear translation of the cutting tip.

6. The apparatus of claim 1, wherein the balloon element is located substantially proximate to a distal end of the flexible, moveable and non-rotatable housing.

7. The apparatus of claim 1, wherein the balloon element is mounted to a multi-lumen assembly mounted to the drilling device.

8. The apparatus of claim 7, wherein the multi-lumen assembly comprises: a first lumen adapted to surround an elongate shaft of the drilling device; and a second lumen in fluid communication with the balloon element.

9. The apparatus of claim 7, wherein the multi-lumen assembly is removably mounted onto the drilling device.

10. The apparatus of claim 7, wherein the multi-lumen assembly is fixedly mounted onto the drilling device.

11. The apparatus of claim 1, wherein the drilling device further comprises a slotted tube.

12. The apparatus of claim 11, wherein the slotted tube is non-rotatable.

13. The apparatus of claim 1, wherein walls of the shaft of the multi-lumen balloon assembly is thin to allow the assembly to remain flexible and/or steerable.

14. The apparatus of claim 1, further comprising a wire tensioner connected to a distal end of the multi-lumen balloon catheter assembly.

15. The apparatus of claim 1, further comprising a feedscrew integrated with a key component and the key component is adapted to mate with a slot in a cannula to ensure correct orientation of the drilling device.

16. The apparatus of claim 15, wherein at least a portion of the multi-lumen balloon assembly passes through the feedscrew.

17. The apparatus of claim 16, wherein a balloon lumen of the multi-lumen balloon assembly passes through the feedscrew.

18. The apparatus of claim 1, wherein the drilling device includes a curved distal end that is induced to curve by a spring loaded pull wire.

19. The apparatus of claim 18, wherein the drilling device includes an axial stiffening wire independent from the pull wire, wherein the stiffening wire extends in a helical pattern axially along the drilling device.

20. An apparatus for forming a curvilinear void in bony structure, comprising:
    a handle assembly;
    a curvilinear drilling device, wherein the drilling device comprises a feedscrew assembly including a feedscrew having a threaded mating with the handle assembly configured to provide rotational and axial driving motion and a key component configured to movably couple the drilling device to the handle assembly to ensure a desired circumferential orientation between the drilling device and the handle assembly, wherein a distal end of the drilling device includes a plurality of slots configured to allow the distal end to bend; and
    a multi-lumen balloon assembly having a hollow shaft and an expandable balloon element mounted on a distal portion of the hollow shaft, wherein the curvilinear drilling device is configured to be slidably inserted through the hollow shaft of the multi-lumen balloon assembly, wherein the drilling device further comprises a flexible drill shaft assembly extending from a distal end of the handle, wherein the flexible drill shaft assembly includes a cutting tip located at a distal end of the flexible drill shaft assembly, a flexible rotatable drive shaft coupled to the tip, and a flexible, moveable and non-rotatable housing, and wherein the curvilinear drilling device and the multi-lumen balloon assembly are configured to be positioned within a vertebral body.

* * * * *